US012567481B2

(12) United States Patent
Bikard et al.

(10) Patent No.: US 12,567,481 B2
(45) Date of Patent: Mar. 3, 2026

(54) METHOD, DEVICE, AND COMPUTER PROGRAM FOR GENERATING PROTEIN SEQUENCES WITH AUTOREGRESSIVE NEURAL NETWORKS

(71) Applicant: INSTITUT PASTEUR, Paris (FR)

(72) Inventors: David Bikard, Paris (FR); Sébastien Baur, Valdurenque (FR); Alexander Hawkins-Hooker, London (GB)

(73) Assignee: INSTITUT PASTEUR, Paris (FR)

( * ) Notice: Subject to any disclaimer, the term of this patent is extended or adjusted under 35 U.S.C. 154(b) by 1668 days.

(21) Appl. No.: 16/757,230

(22) PCT Filed: Nov. 16, 2018

(86) PCT No.: PCT/EP2018/081614
§ 371 (c)(1),
(2) Date: Apr. 17, 2020

(87) PCT Pub. No.: WO2019/097014
PCT Pub. Date: May 23, 2019

(65) Prior Publication Data
US 2021/0193259 A1 Jun. 24, 2021

(30) Foreign Application Priority Data

Nov. 16, 2017 (EP) ..................................... 17306591

(51) Int. Cl.
| | |
|---|---|
| *G16B 30/00* | (2019.01) |
| *G16B 20/00* | (2019.01) |
| *G16B 20/20* | (2019.01) |
| *G16B 40/30* | (2019.01) |

(52) U.S. Cl.
CPC ............. *G16B 30/00* (2019.02); *G16B 20/00* (2019.02); *G16B 20/20* (2019.02); *G16B 40/30* (2019.02)

(58) Field of Classification Search
None
See application file for complete search history.

(56) References Cited

PUBLICATIONS

De Campos, Lídio Mauro Lima, Roberto Célio Limão de Oliveira, and Mauro Roisenberg. "A hybrid neuro-evolutive algorithm for neural network optimization." 2016 International Joint Conference on Neural Networks (IJCNN). IEEE, 2016.*
Packer MS et al., "Methods for the directed evolution of proteins:", Nat. Rev. Genet., 2015, 16, pp. 379-394.
Huang PS et al., "the coming of age of de novo protein design", Nature, 2016, 537, pp. 320-327.
Gainza P et al., "Algorithms for protein design", Curr. Opin. Struct. Biol., 2016, 39, pp. 16-26.

Xueliang Liu, "Deep Recurrent Neural Network for Protein Function Prediction from Sequence", XP055472357, Retrieved from the Internet: URL:https://arxiv.org/ftp/arxiv/papers/1701/1701.08318.pdf [retrieved May 3, 2018] , Jan. 28, 2017, pp. 23.
Anonymous: "Autoencoder—Wikipedia", XP055472587, Retrieved from the Internet: URL:https://en.wikipedia.org/w/index.php?title=Autoencoder&oldid=809530971 [retrieved on May 4, 2018], Nov. 9, 2017.
Yo Joong Choe et al., "Probabilistic Interpretations of Recurrent Neural Networks", XP055472541, Retrieved from Internet:URL:https://www.cs.cmu.edu/~epxing/Class/10708-17/project-reports/project10.pdf [retrieved May 4, 2018], May 29, 2017.
Aaron van den Oord et al., "Conditional Image Generation with FixelCNN Decoders", arxiv.org, Cornell University Library, 201 Olin Library Cornell University Ithaca, NY 14853, XP080709038, Jun. 16, 2016.
Aaron van den Oord et al., "Pixel Recurrent Neural Networks", XP055404359, Retrieved from the Internet: URL:https://arxiv.org/pdf/1601.06759.pdf [retrieved on Sep. 2017, Jan. 25, 2016.
Ilya Sutskever et al., "Generating Text with Recurrent Neural Networks", XP055472805, retrieved from the Internet: URL:http://www.icml-2011.org/papers/524_icmlpaper.pdf [retrieved on May 4, 2018], Jul. 1, 2011.
Rafael Gomez-Bombarelli et al., "Automatic Chemical Design Using a Data-Driven Continuous Representation of Molecules", arXiv.org, XP055471667, Retrieved from the Internet: URL:https://arviv.org/pdf/1610.02415v2.pdf [retrieved on May 2, 2018], Jan. 6, 2017.
Stanislau Semeniuta et al., "A Hybrid Convolutional Variational Autoencoder for Text Generation", arxiv.org, Cornell University Library, 201 Olin Library Cornell University Ithaca, NY 14853, XP080747075, Feb. 8, 2017.
Ishaan Gulrajani et al., "PixelVAE: A Latent Variable Model for Natural Images", arxiv.org, Cornell University Library, 201 Olin Library Cornell University Ithaca, NY 14853, XP080731998, Nov. 15, 2016.

(Continued)

*Primary Examiner* — G. Steven Vanni
(74) *Attorney, Agent, or Firm* — NIXON & VANDERHYE

(57) ABSTRACT

The invention relates to a method for generating protein sequences in an autoregressive neural network comprising an encoder and a decoder, the decoder comprising an autoregressive module, the method comprising:
obtaining a latent code and inputting the latent code into the autoregressive module;
obtaining probabilities from the autoregressive module, the obtained probabilities representing probabilities for amino acids to be selected at locations of the sequence; and
generating an ordered sequence of amino acids from the obtained probabilities,
wherein the autoregressive module is such that, for a location of the sequence, the probabilities associated with amino acids to be selected for the location in the sequence are determined as a function of probabilities of amino acids to be selected for previous locations in the sequence and
wherein the autoregressive neural network has been trained end-to-end with the encoder, the encoder making it possible to encode protein sequences in a latent space as latent codes.

20 Claims, 19 Drawing Sheets
(14 of 19 Drawing Sheet(s) Filed in Color)

Specification includes a Sequence Listing.

(56)                  References Cited

PUBLICATIONS

International Search Report issued in International Patent Application No. PCT/EP2018/081614, dated Feb. 13, 2019.

* cited by examiner

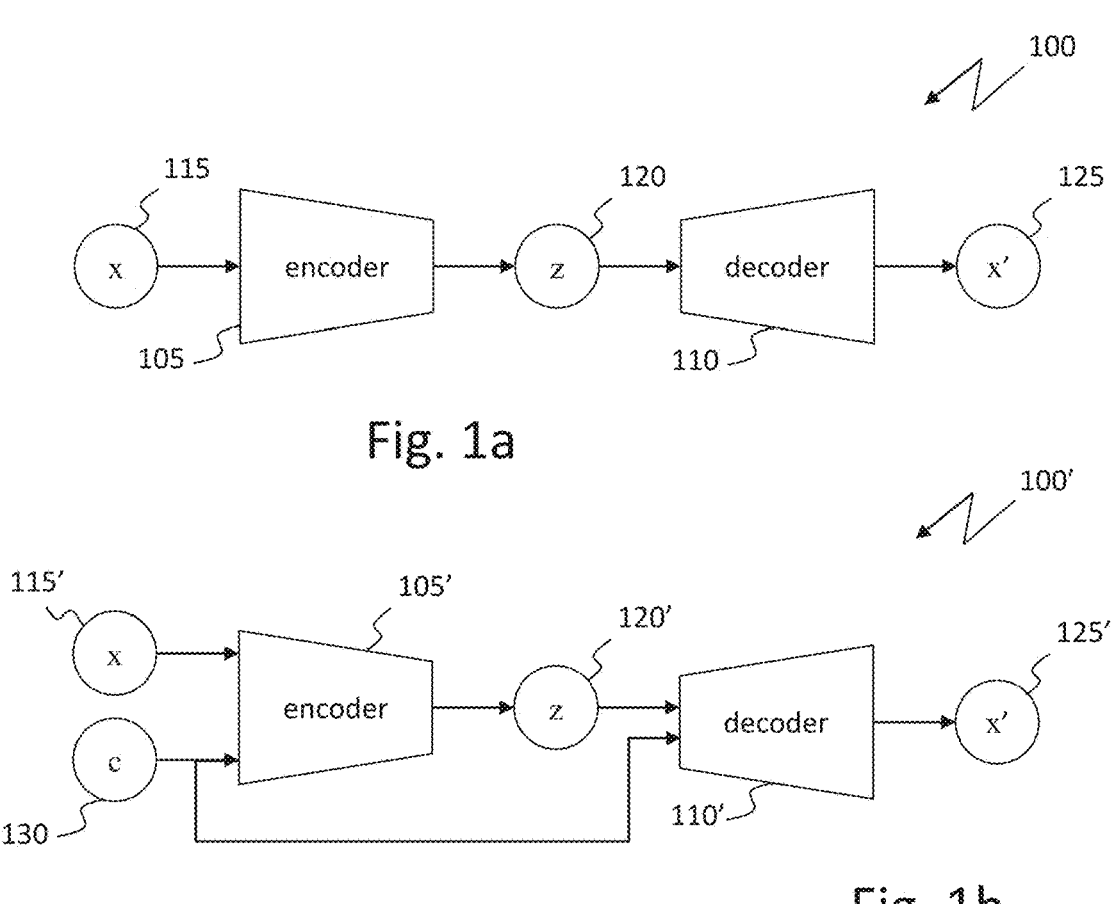
Fig. 1a
Fig. 1b
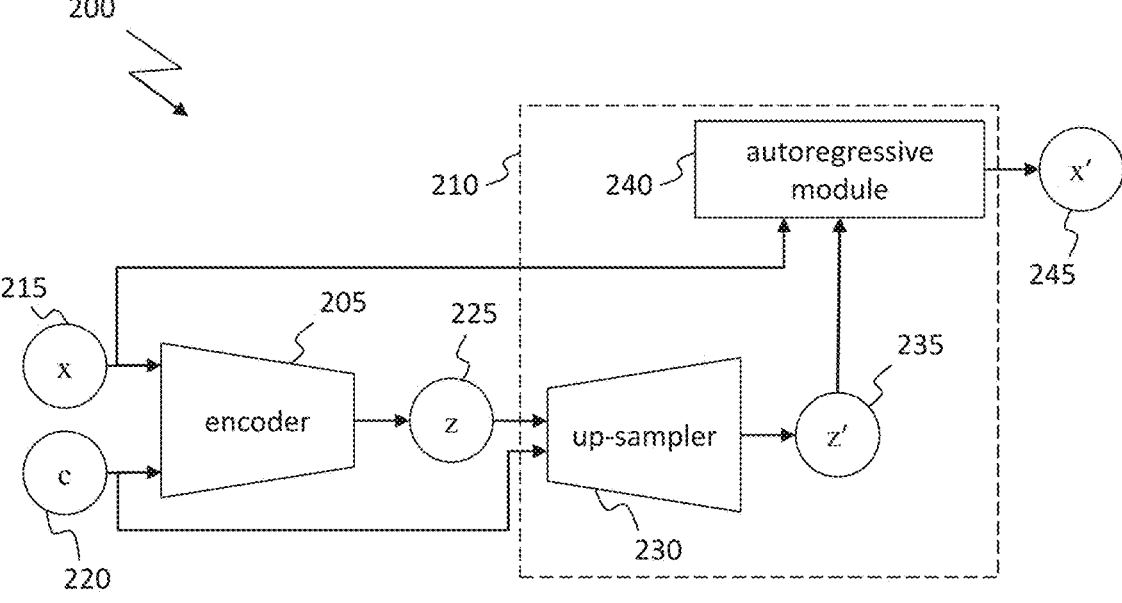
Fig. 2a

2100

METHOD, DEVICE, AND COMPUTER PROGRAM FOR GENERATING PROTEIN SEQUENCES WITH AUTOREGRESSIVE NEURAL NETWORKS

FIELD OF THE INVENTION

The invention generally relates to the field of protein sequences and of generating protein sequences. More particularly, the invention concerns a method, a device, and a computer program for generating protein sequences with autoregressive neural networks.

BACKGROUND OF THE INVENTION

Proteins are versatile molecules consisting of chains of amino acids which fold in 3D space to form molecular machines able to bind specific substrates, self-organize in larger structures, catalyze chemical reactions, and convert various sources of energy such as light and chemical gradients into chemical bonds or work, and more.

Thanks to their biological activity, recombinant proteins have found uses in medical applications including vaccines, antibodies, and growth factors. Their catalytic potential is also used in diverse industries ranging from paper, biofuel, food and detergent to chemical synthesis.

In many cases, it is desirable to modify the properties of the natural proteins used in these applications to improve stability, increase catalytic activity, modify substrate preferences etc.

As described in the article entitled "*Methods for the directed evolution of proteins*", Packer M S et al., Nat. Rev. Genet., 2015, 16, 379-394, this can be achieved through the generation of more or less random mutations in the protein sequence and selection for the best performing variants. According to other solutions, when knowledge of the protein structure is available, computer aided rational design can help identify interesting modifications as described in the paper entitled "*Algorithms for protein design*", Gainza P et al., Curr. Opin. Struct. Biol., 2016, 39, 16-26. Still according to other solutions, proteins can be designed from scratch as illustrated in the paper entitled "*The coming of age of de novo protein design*", Huang P S et al., Nature, 2016, 537, 320-327.

However the systematic exploration of protein variants is made extremely challenging by the enormous space of possible sequences and the difficulty of accurately predicting protein fold and function. Indeed, proteins are composed of 20 different amino acids forming chains ranging from just a few, to thousands of amino acids. Accordingly, there are $20^{300}$ possible proteins of length 300 (which corresponds to an average sized protein), i.e. vastly more than the number of atoms in the universe and what has been explored by the natural evolutionary process.

Accordingly, there is a need to explore the protein sequence space in a smart way to obtain interesting functional variants.

SUMMARY OF THE INVENTION

Faced with these constraints and limitations, the inventors provide a method, a device, and a computer program for generating protein sequences, i.e. ordered sequences of amino acids, with autoregressive neural networks.

It is a broad object of the invention to remedy the shortcomings of the prior art as described above.

According to a first aspect of the invention there is provided a computer method for generating a protein sequence in an autoregressive neural network comprising an encoder and a decoder, the decoder comprising an autoregressive module, the method comprising the steps of:

obtaining a latent code and inputting the latent code into the autoregressive module;

obtaining probabilities from the autoregressive module, the obtained probabilities representing probabilities for amino acids to be selected at given locations of the sequence; and generating an ordered sequence of amino acids from the obtained probabilities, wherein the autoregressive module is such that, for a location of the sequence, the probabilities associated with amino acids to be selected for the location in the sequence are determined as a function of probabilities of amino acids to be selected for previous locations in the sequence and wherein the autoregressive neural network has been trained end-to-end with the encoder, the encoder making it possible to encode protein sequences in a latent space as latent codes.

In particular, the claimed method makes it possible to sample new proteins, in particular proteins having specific physical or functional properties, to obtain variants of a sequence while conserving structural and functional properties of the initial protein, and to obtain sequence variants with desired modified physical or functional properties.

The autoregressive neural network learns transformations preserving similarities in structures and relatedness between amino acids. It is able to modify physical properties of existing proteins and to generate new ones having chosen properties with relative accuracy.

According to embodiments, the method further comprises a step of obtaining additional information representative of at least one characteristic of a protein sequence to be generated, the additional information being input along with the latent code into the autoregressive module, additional information representative of characteristics of protein sequences used for training the autoregressive neural network being input along with protein sequences into the encoder during training.

According to embodiments, the additional information is directed to physical characteristics of the protein sequences to be generated and of the protein sequences used for training the autoregressive neural network.

According to embodiments, the decoder further comprises an up-sampling module for increasing a number of dimensions of a latent code, the obtained latent code being input into the up-sampling module and the up-sampled latent code being input into the autoregressive module.

According to embodiments, the step of generating an ordered sequence of amino acids comprises a step of selecting sequentially each amino acid of the ordered sequence and, after an amino acid is selected to belong to the ordered sequence, a step of checking the likelihood of usefulness of the ordered sequence at least partially generated.

According to embodiments, the step of checking the likelihood of usefulness of the ordered sequence at least partially generated comprises a step of comparing the length of the ordered sequence at least partially generated with a threshold.

According to embodiments, the step of generating an ordered sequence of amino acids comprises a step of selecting sequentially each amino acid of the ordered sequence and the step of generating an ordered sequence of amino acids is stopped if a specific symbol is selected as an amino acid for a given position of the ordered sequence.

According to embodiments, the step of generating an ordered sequence of amino acids comprises a step of selecting one amino acid, for a given position of the ordered sequence, among a plurality of amino acids, the one amino acid being selected as a function of the probabilities associated with amino acids of the plurality of amino acids for the given position.

According to embodiments, the method further comprises a step of modifying probabilities obtained from the autoregressive neural network, denoted the first autoregressive neural network, as a function of probabilities obtained from a second autoregressive neural network different from the first autoregressive neural network.

According to embodiments, the method further comprises a learning phase for determining parameters of the autoregressive module.

According to embodiments, the learning phase is unsupervised.

According to embodiments, the autoregressive neural network is of the variational auto-encoder type or of the adversarial auto-encoder type.

According to embodiments, the autoregressive neural network is a recurrent neural network.

According to a second aspect of the invention there is provided an apparatus comprising means configured for carrying out each step of the method described above. The advantages provided by the second aspect of the present invention are similar to the ones provided by the first above-mentioned aspect.

Since parts of the present invention can be implemented in software, parts of the present invention can be embodied as computer readable code for provision to a programmable apparatus on any suitable carrier medium. A tangible carrier medium may comprise a storage medium such as a floppy disk, a CD-ROM, a hard disk drive, a magnetic tape device or a solid state memory device and the like. A transient carrier medium may include a signal such as an electrical signal, an electronic signal, an optical signal, an acoustic signal, a magnetic signal or an electromagnetic signal, e.g. a microwave or RF signal.

In an embodiment, the computer code exploits graphic processing units (GPUs) that allow parallel processing of large matrix data.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Further advantages of the present invention will become apparent upon examination of the drawings and detailed description. It is intended that any additional advantages be incorporated herein.

Figure 2B:
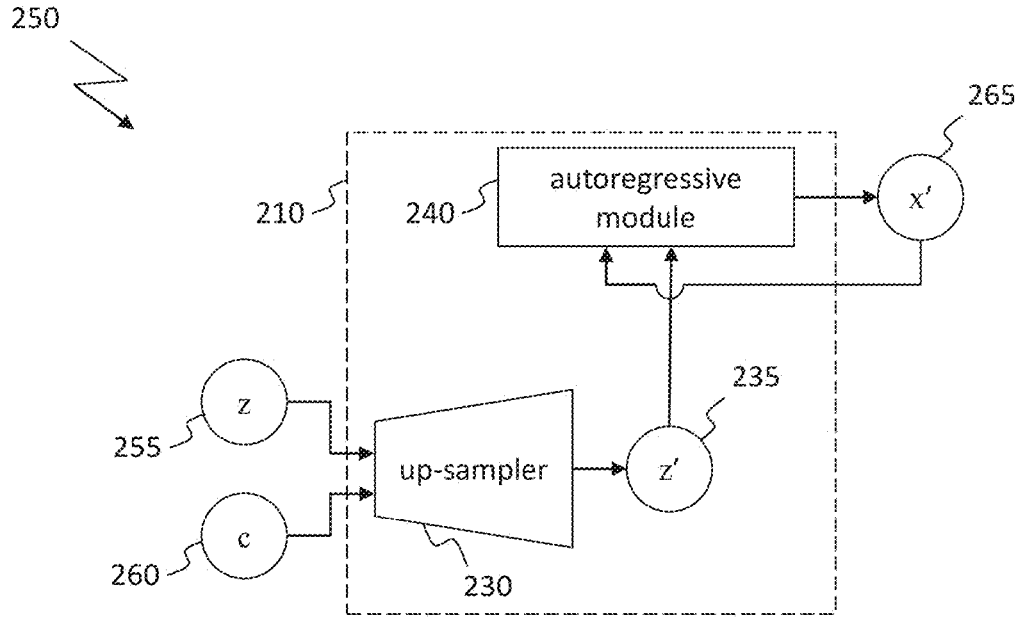
Figure 3:
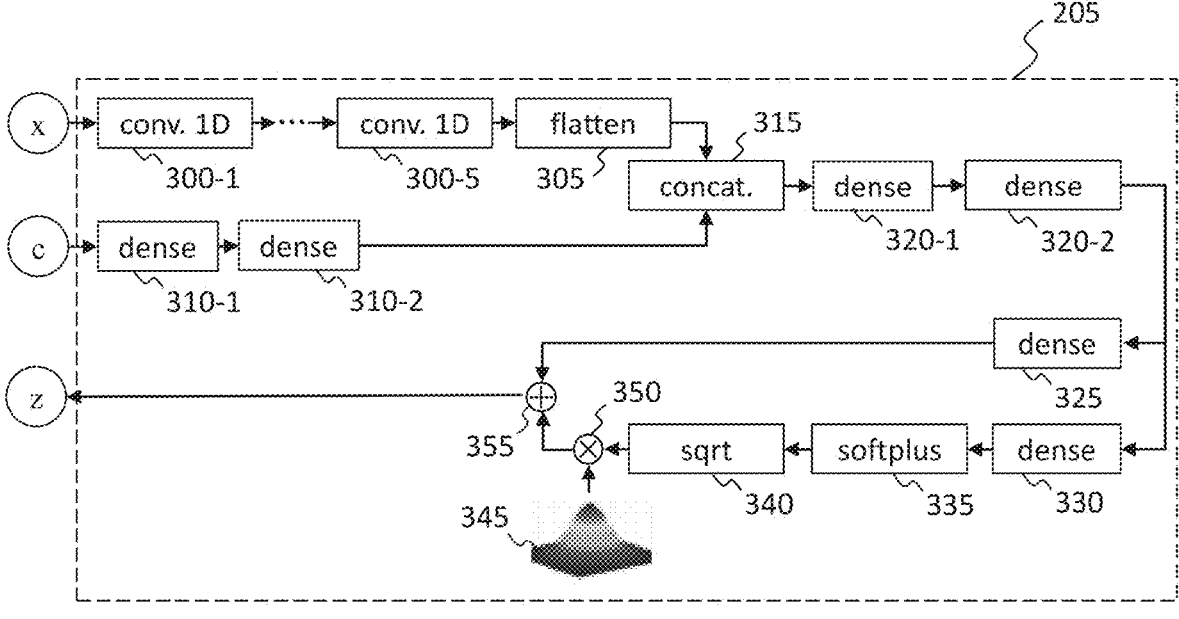
Figure 4A:
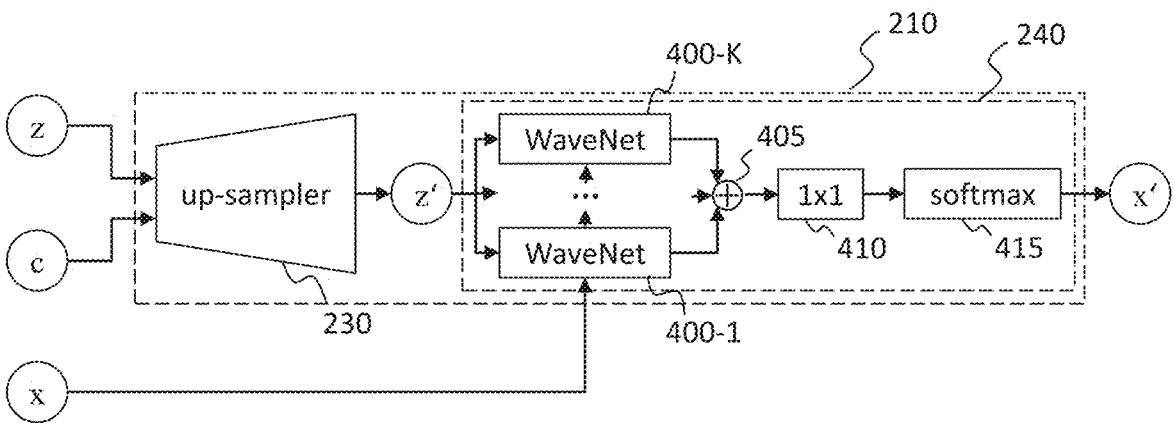
Figure 4B:
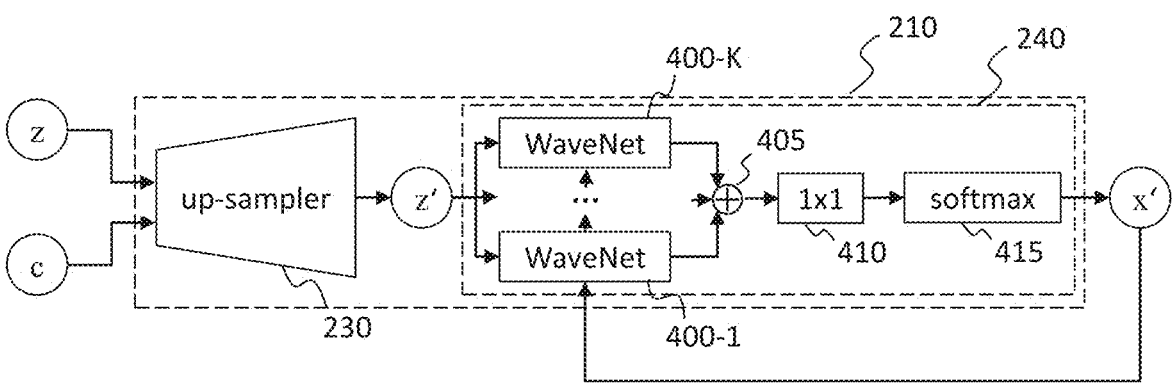
Figure 5A:
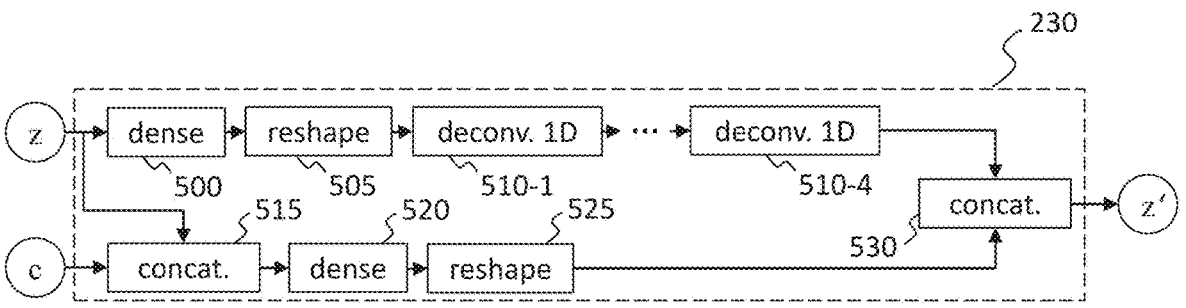
Figure 5B:
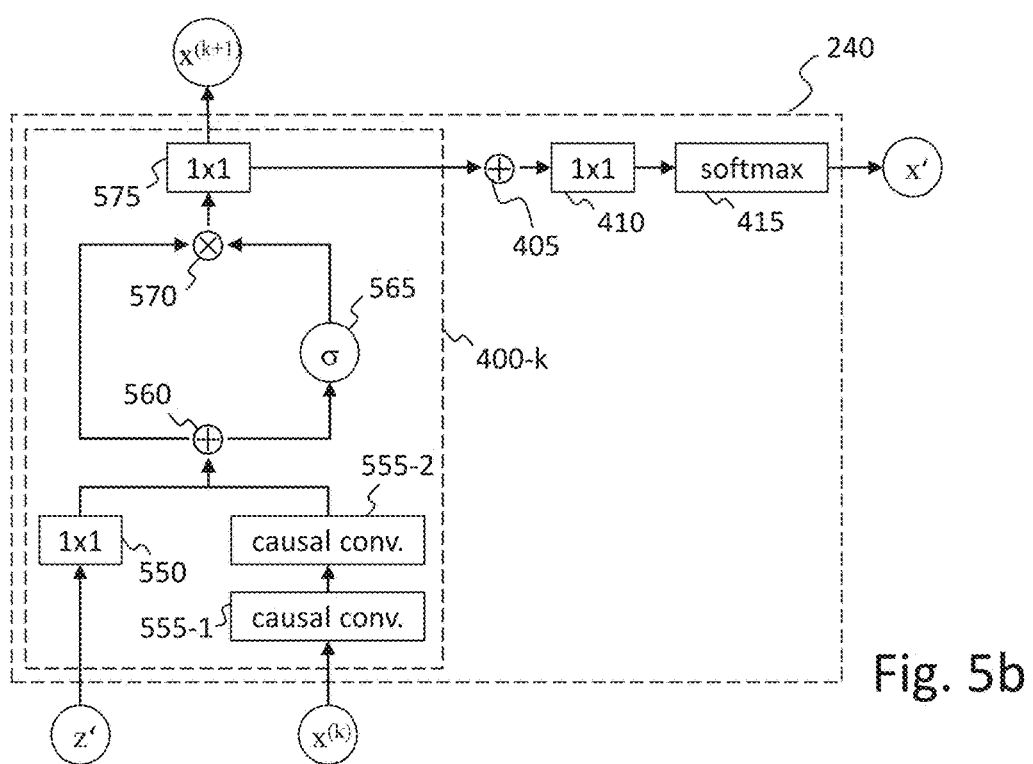
Figure 6:
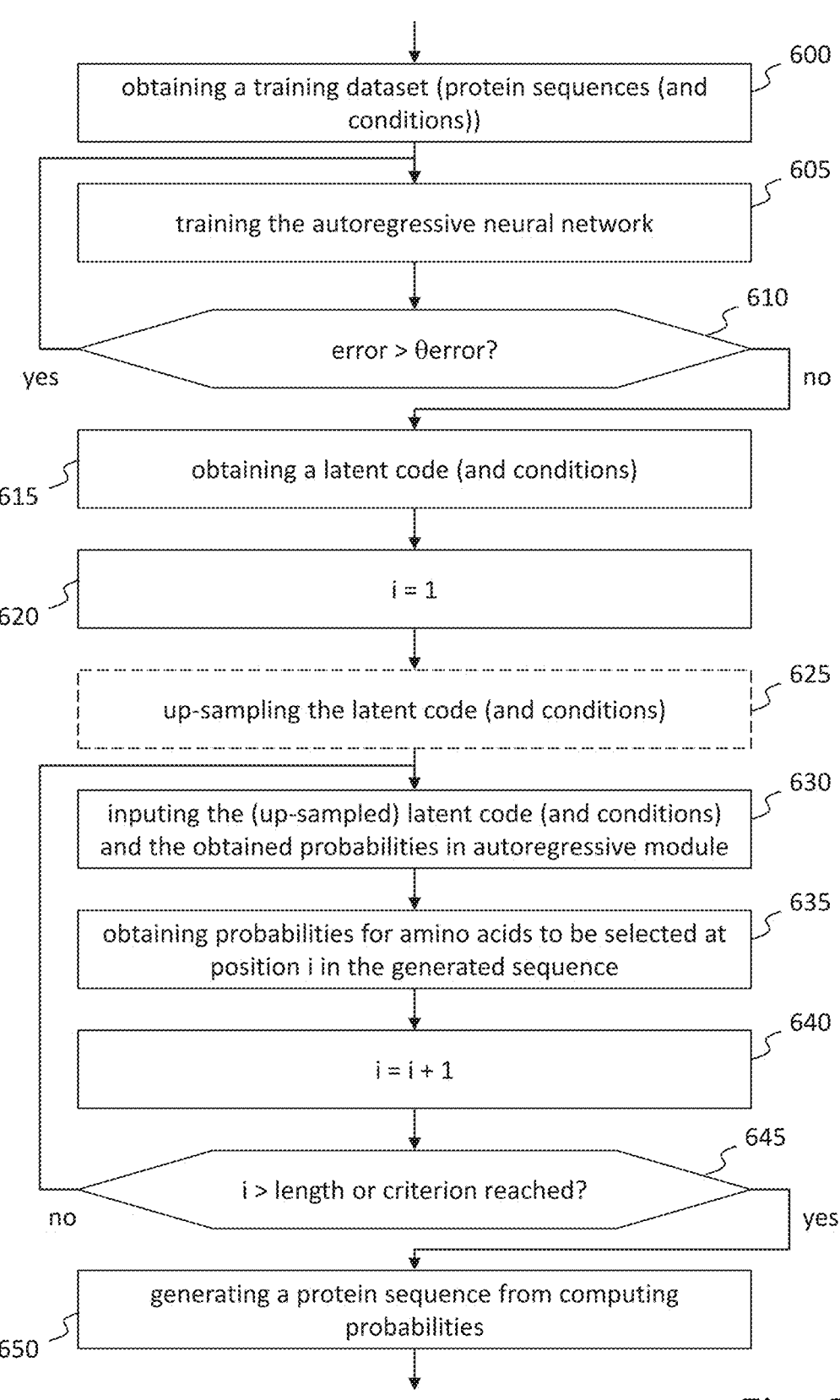
Figure 7:
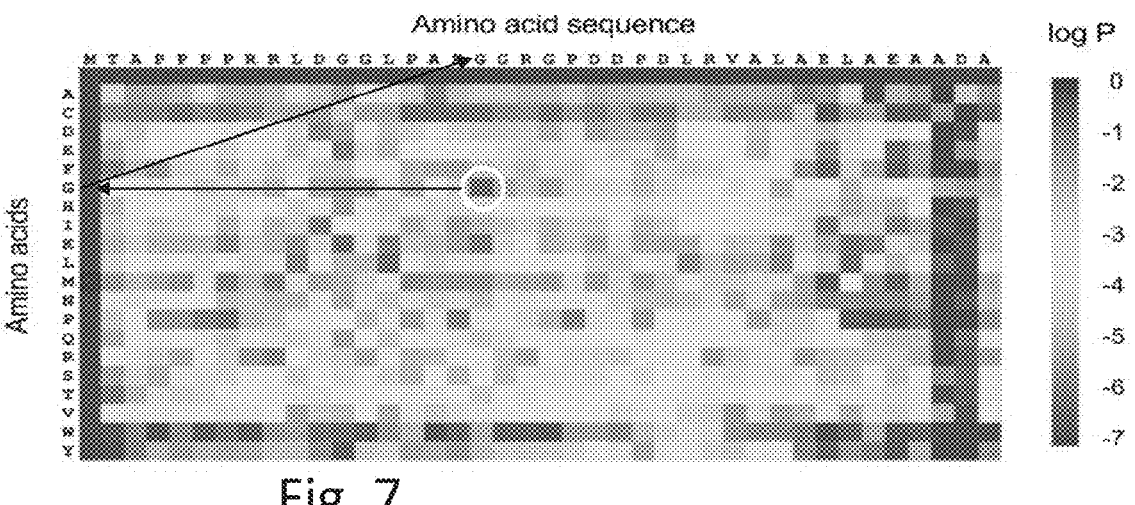
Figure 8:
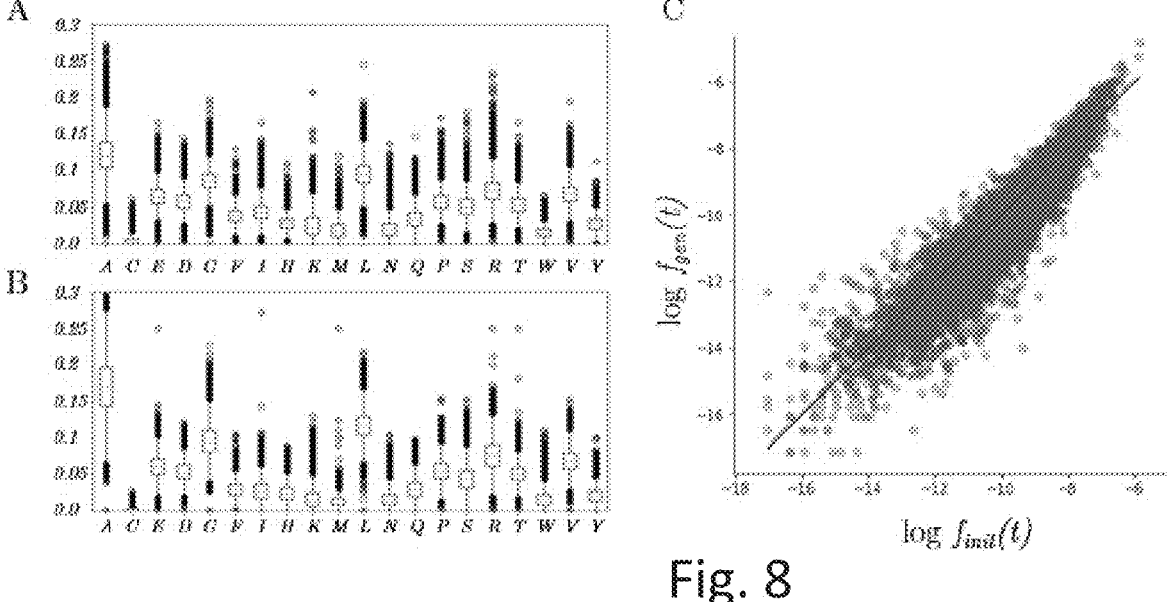
Figure 10:
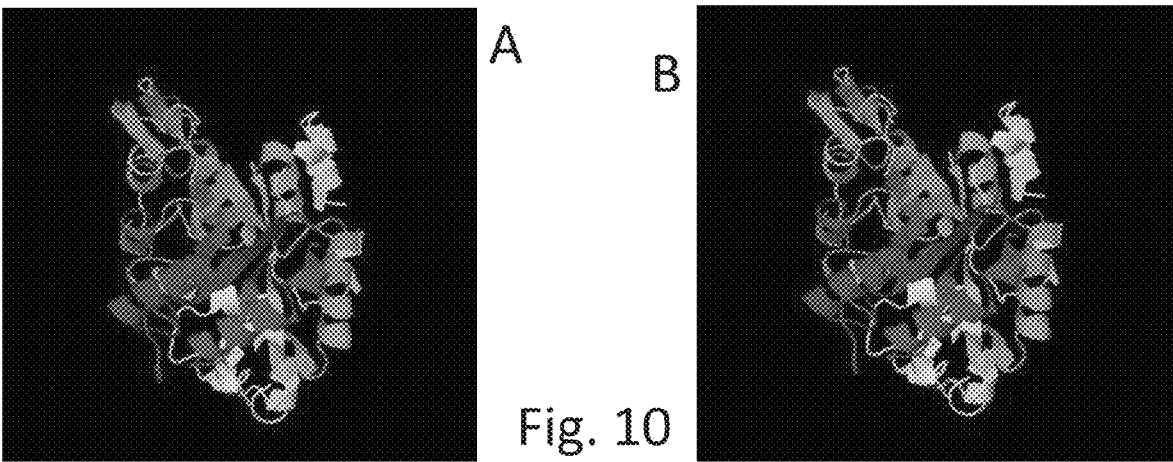
Figure 9:
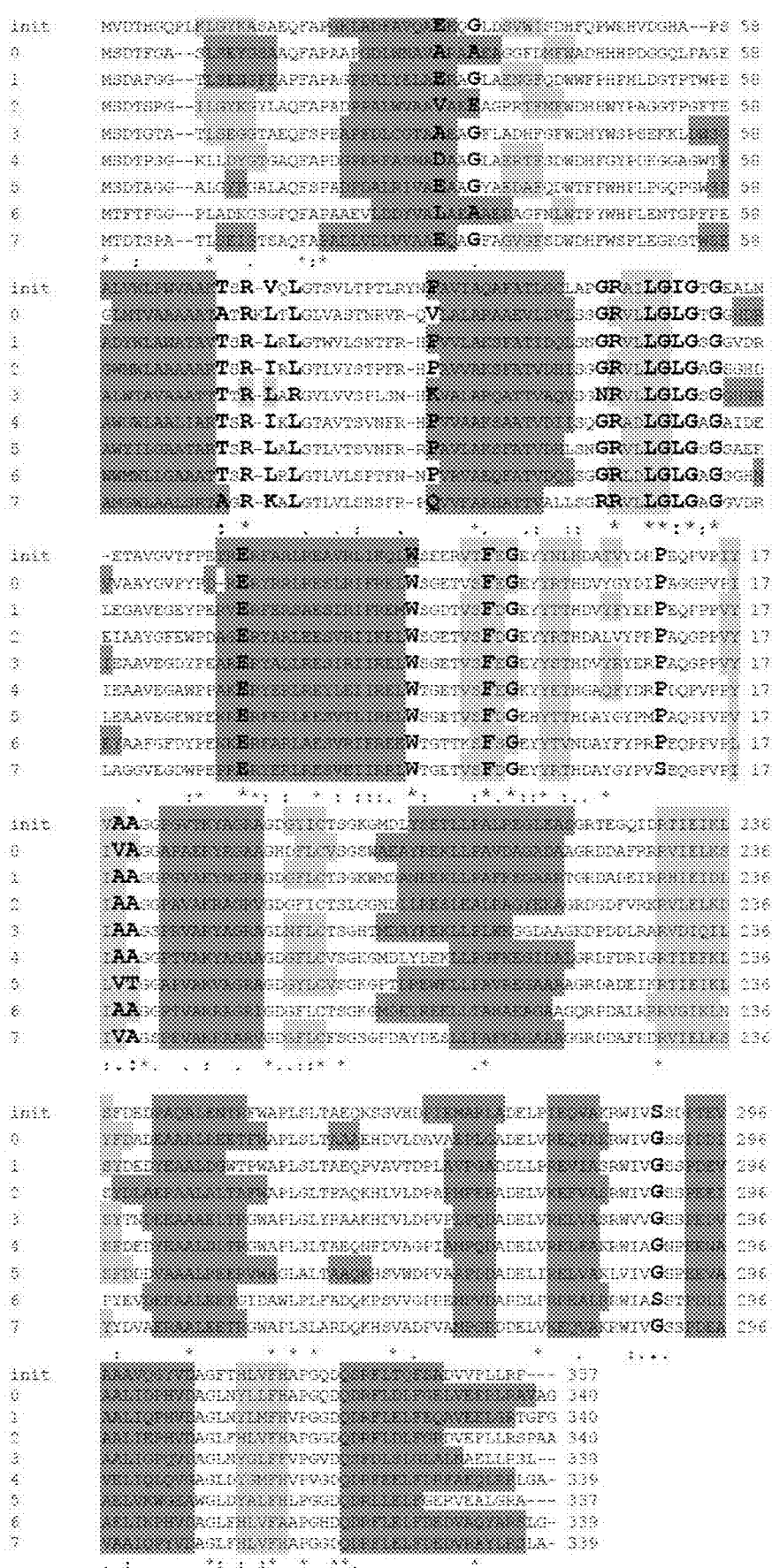
Figure 11:
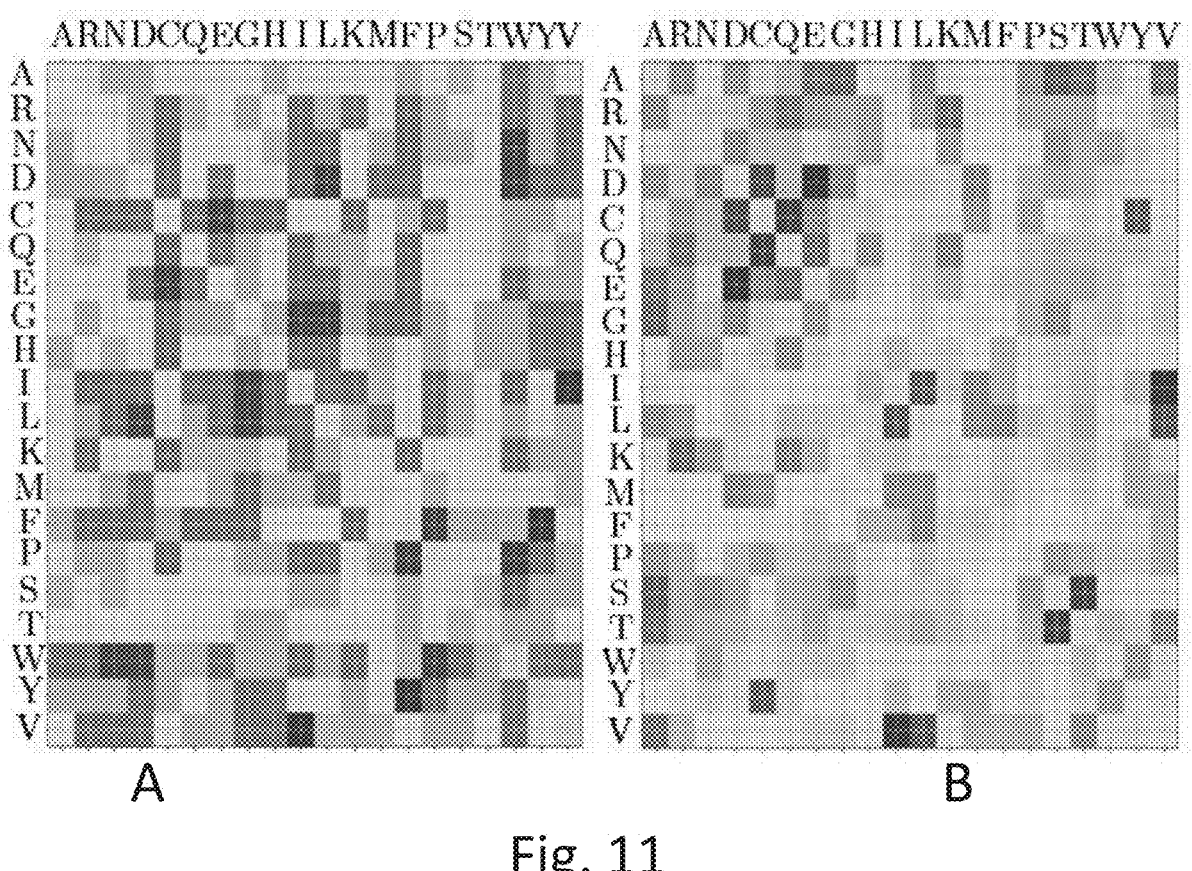
Figure 18:
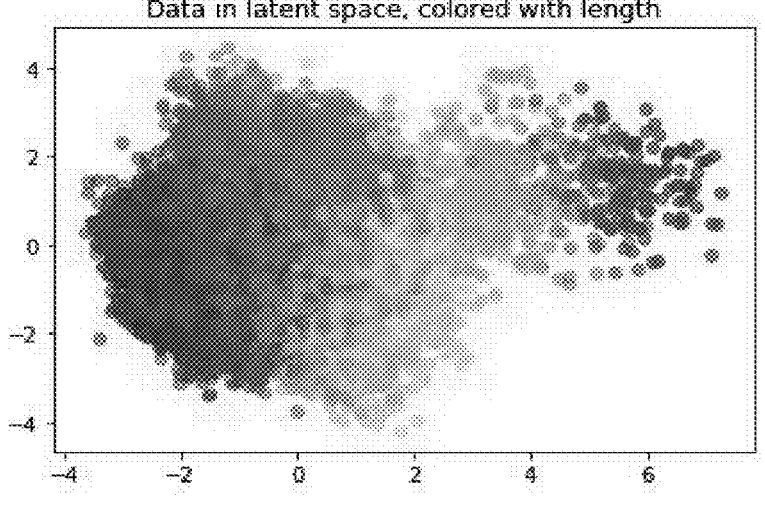
Figure 17:
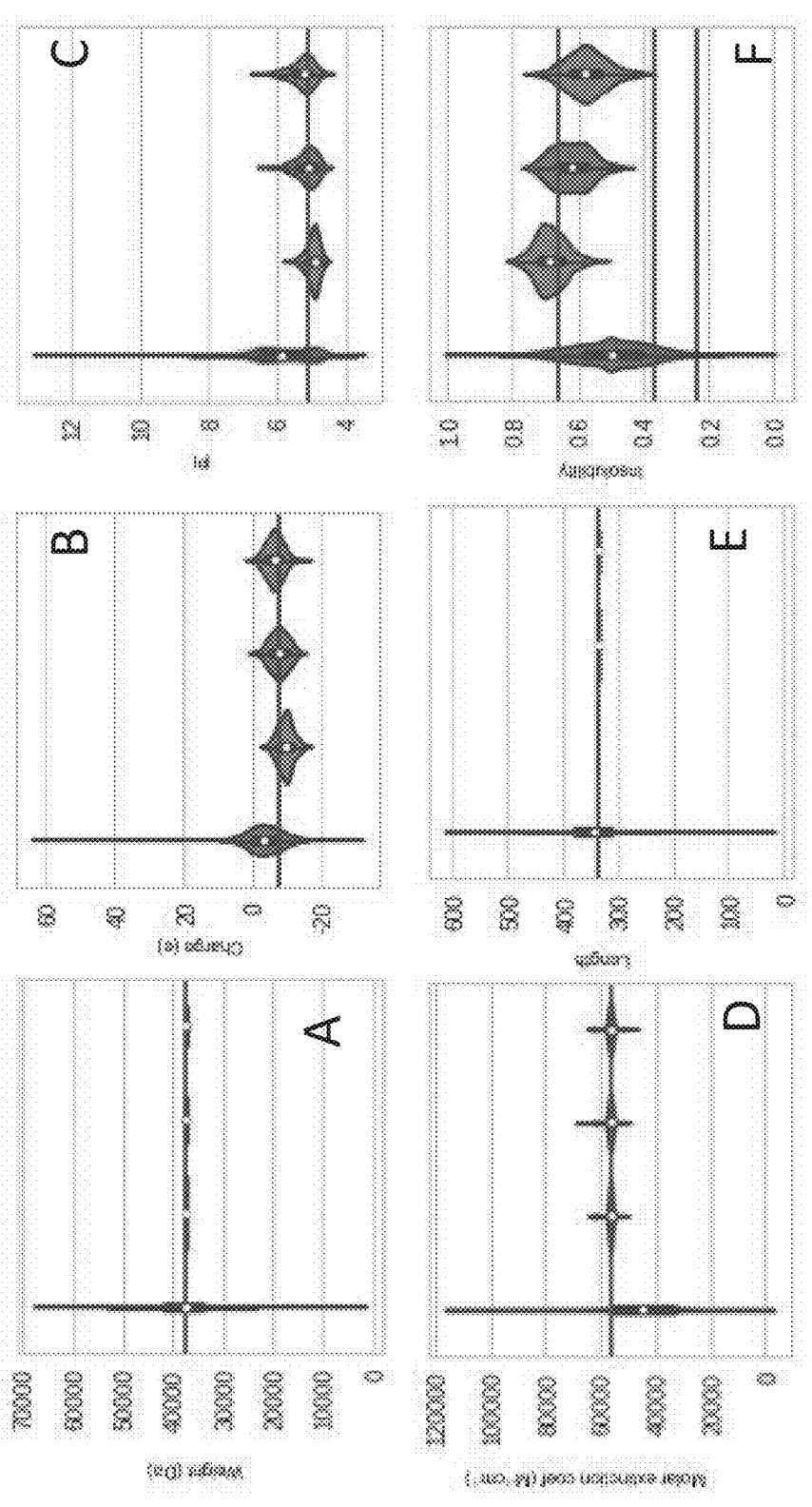
Figure 19:
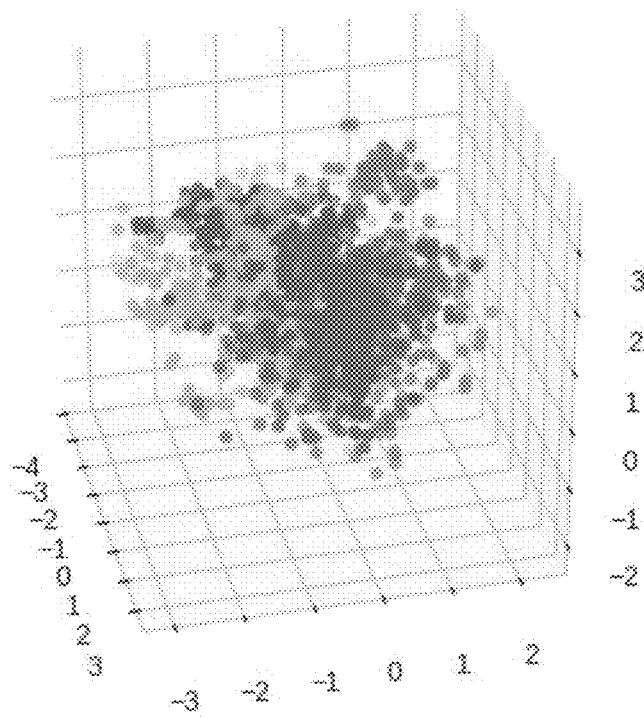
Figure 20:
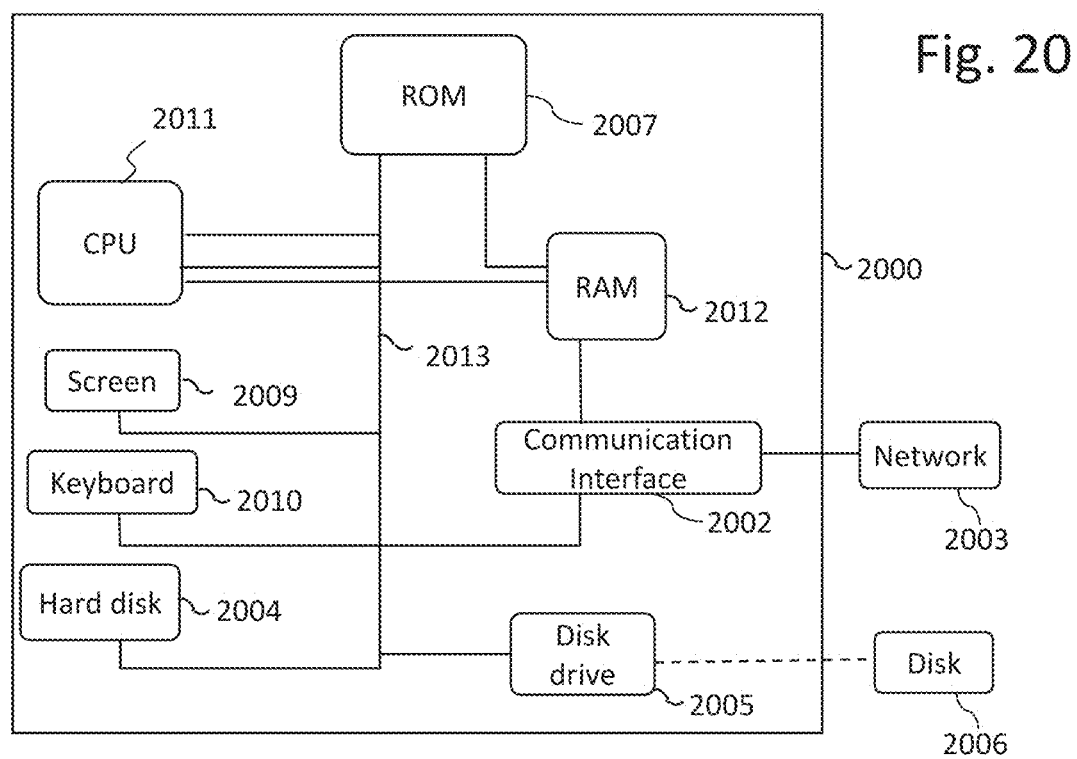
Figure 21:
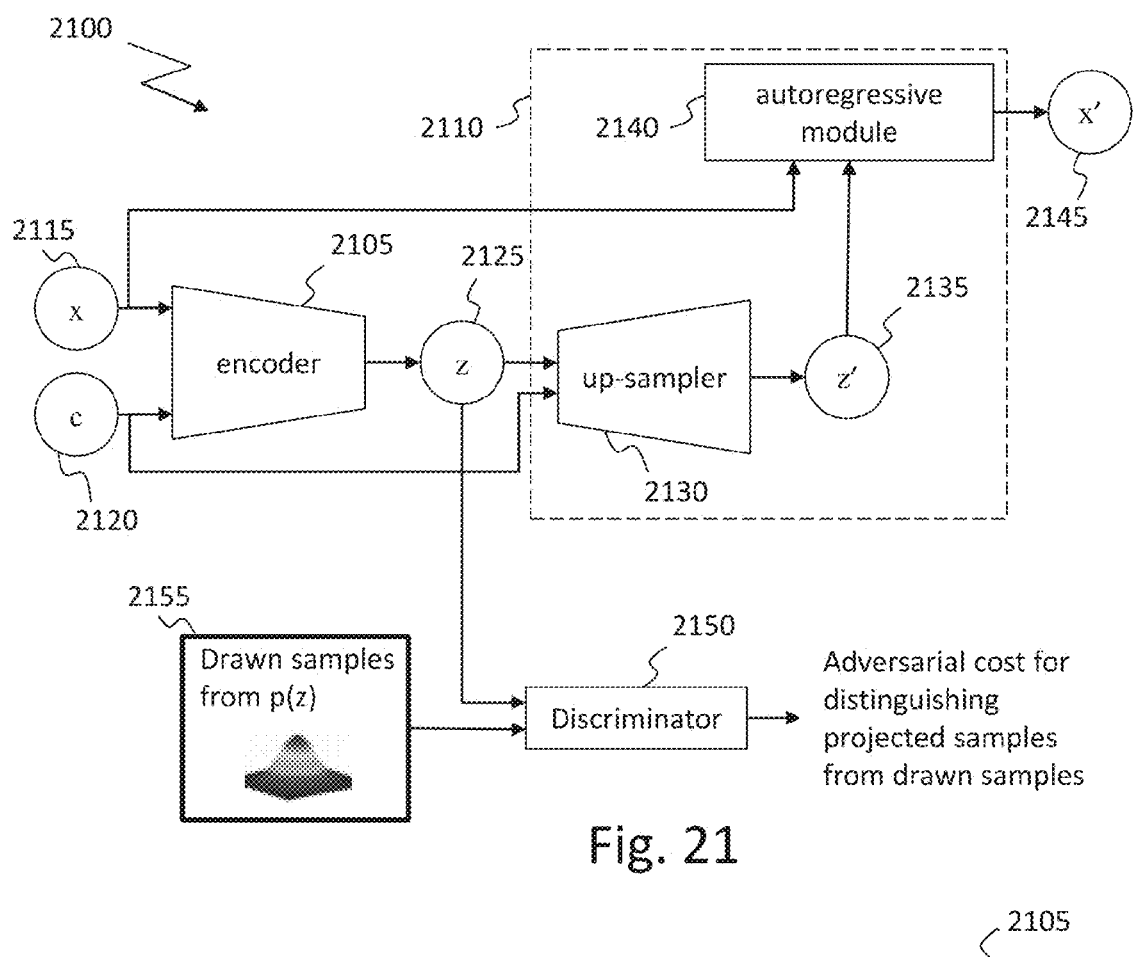
Figure 22A:
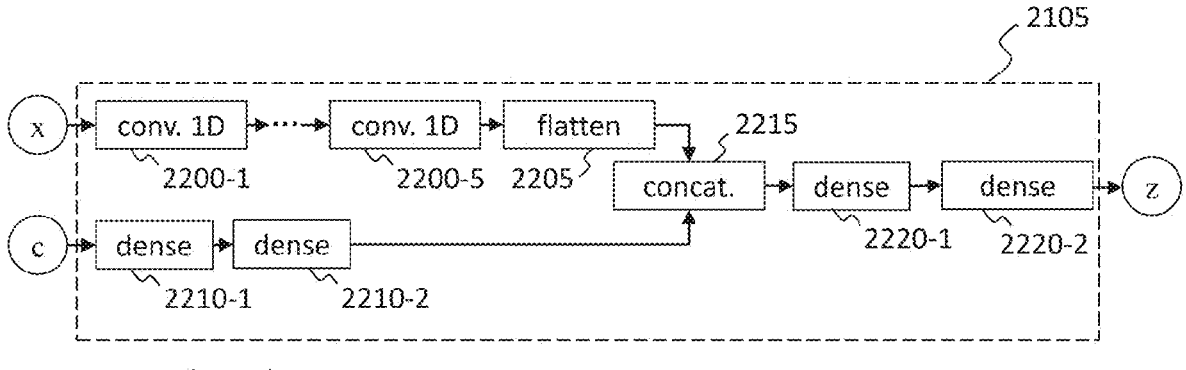
Figure 22B:
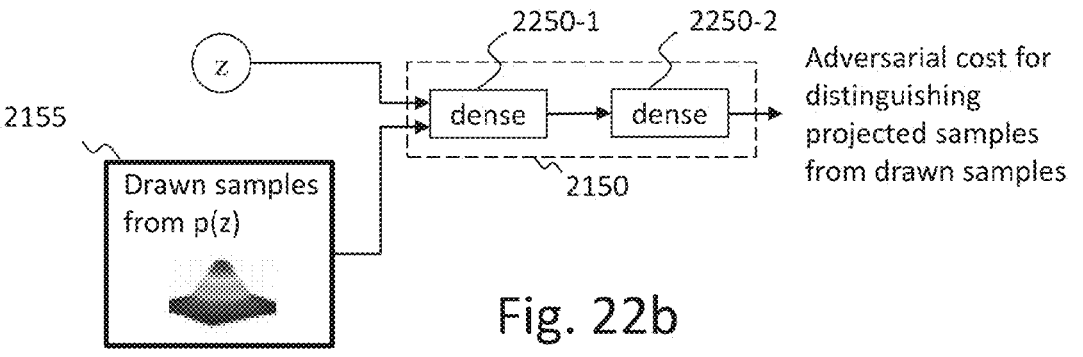

Embodiments of the invention will now be described, by way of example only, and with reference to the following drawings in which:

FIG. 1a and FIG. 1b illustrate the logical architecture of a variational auto-encoder and of a conditional variational auto-encoder, respectively;

FIG. 2a and FIG. 2b illustrate an example of the logical architecture of a conditional variational auto-encoder having an autoregressive decoder, used during the training phase and for generating new protein sequences, respectively;

FIG. 3 illustrates an example of the functional architecture of the encoder illustrated in FIG. 2a;

FIG. 4a and FIG. 4b illustrate an example of the functional architecture of the autoregressive decoder illustrated in FIGS. 2a and 2b, during training and during generation, respectively;

FIG. 5a and FIG. 5b illustrates an example of the functional architecture of the up-sampler and of network blocks of the autoregressive module, respectively, illustrated in FIGS. 2a, 2b, 4a, and 4b;

FIG. 6 illustrates an example of steps of a method for generating a protein sequence with an autoregressive neural network such as the conditional variational auto-encoder illustrated in FIGS. 2a and 2b or a (conditional) adversarial auto-encoder;

FIG. 7 illustrates a conditional probability distribution table wherein the probability of each amino acid is computed as a function of the previous amino acids in the sequence and of the up-sampled latent vector;

FIG. 8 makes it possible to compare the distribution of amino acids in generated sequences with patterns of amino acid occurrences of the training dataset;

FIG. 9 illustrates preservation of secondary structures in reconstructions by showing alignments between one protein and its reconstructions;

FIG. 10 illustrates 3D structures of the two proteins as predicted by Phyre2 for the initial protein (A) and for one of its reconstructions presented in FIG. 9 (B);

FIG. 11 illustrates a BLOSUM62 matrix and BLOSUM-like generated matrix;

FIGS. 12 to 16 illustrate generation of protein sequences when conditioned on solubility, protein length, protein length and weight, charge, and molar extinction coefficient, respectively;

FIG. 17 illustrates generation of variants of a protein with desired properties;

FIG. 18 illustrates the projection of the training dataset in the latent space of an unconditioned model, colored as a function of the protein length;

FIG. 19 illustrates the projection of 5 Interpro families in the latent space;

FIG. 20 is a block diagram illustrating components of a processing device in which embodiments of the invention may be at least partially implemented;

FIG. 21 illustrates an example of the logical architecture of a conditional adversarial auto-encoder having an autoregressive decoder;

FIG. 22a and FIG. 22b illustrate an example of the functional architecture of the encoder and of the discriminator illustrated in FIG. 21, respectively.

Figure 23:
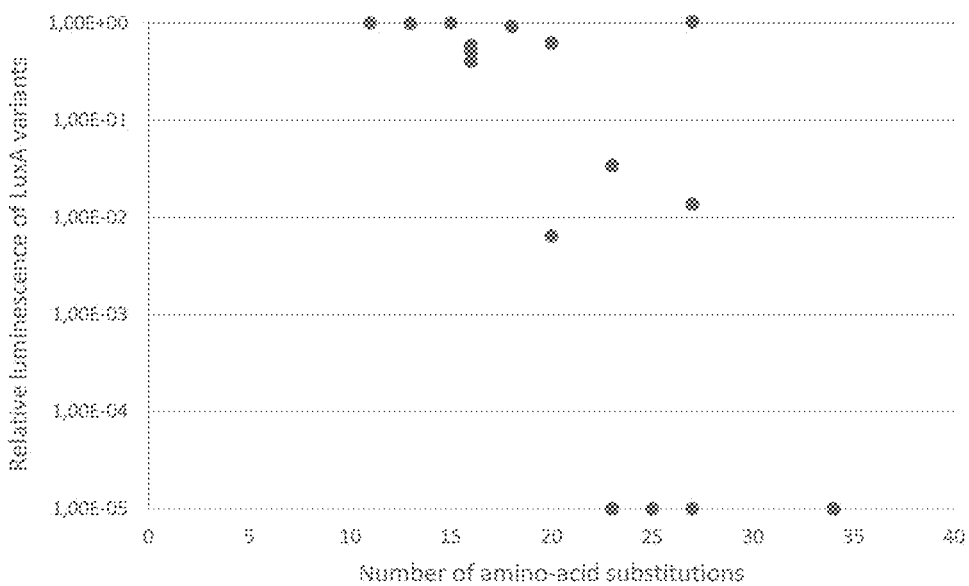
Figure 24:
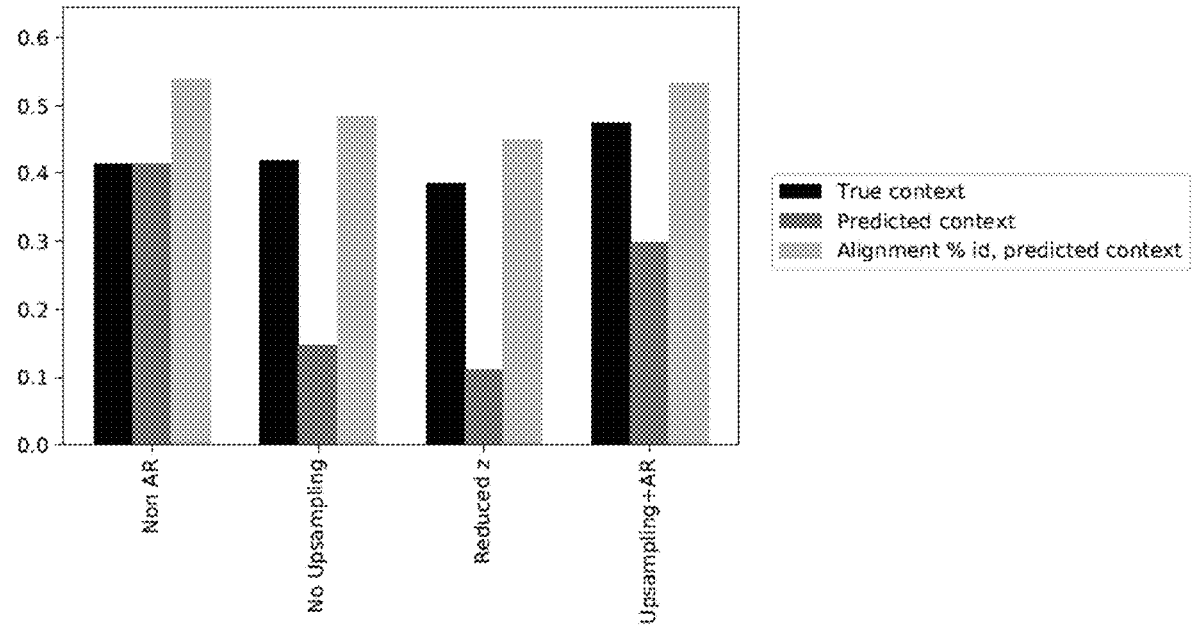
Figure 25:
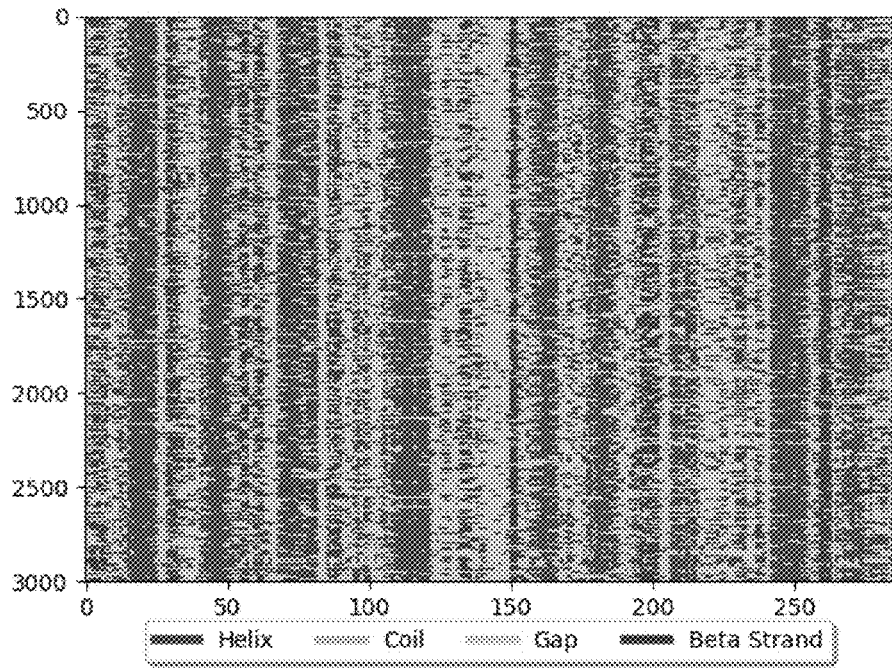
Figure 26:
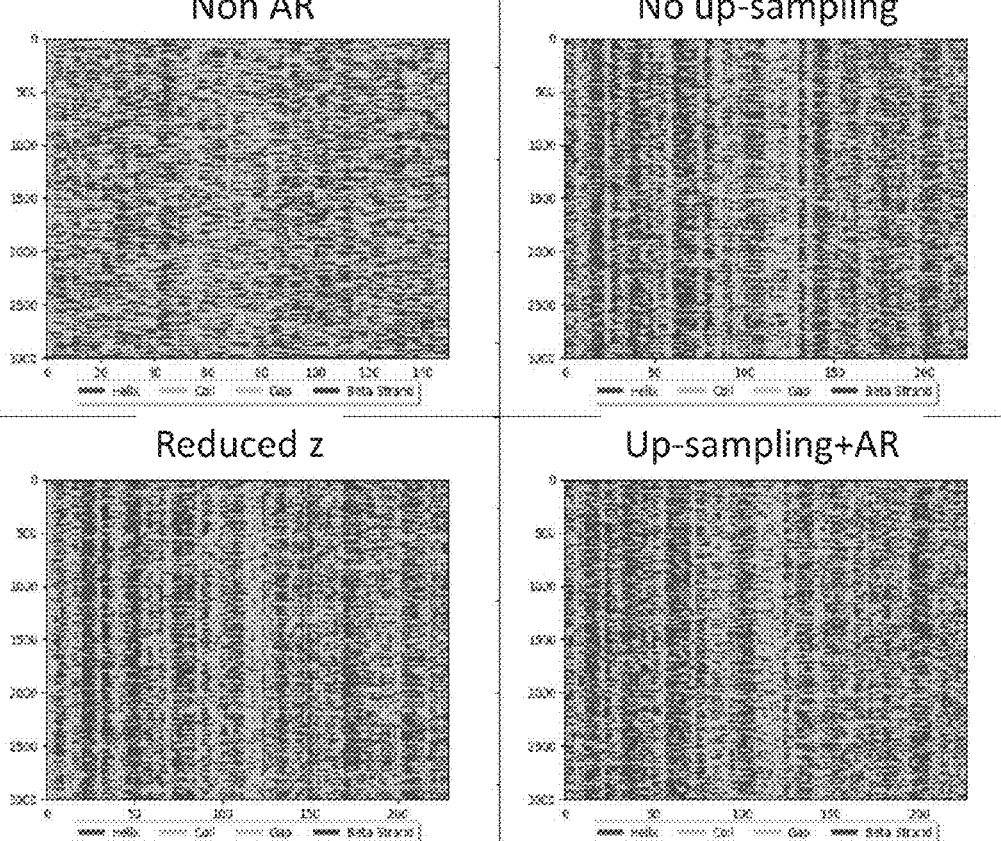
Figure 27:
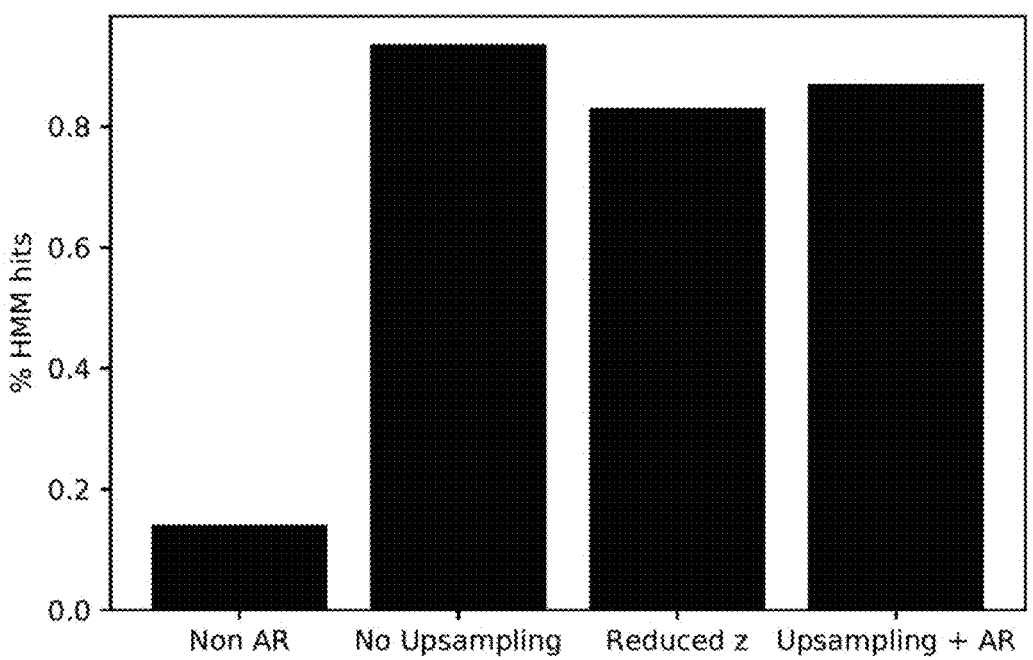
Figure 28:
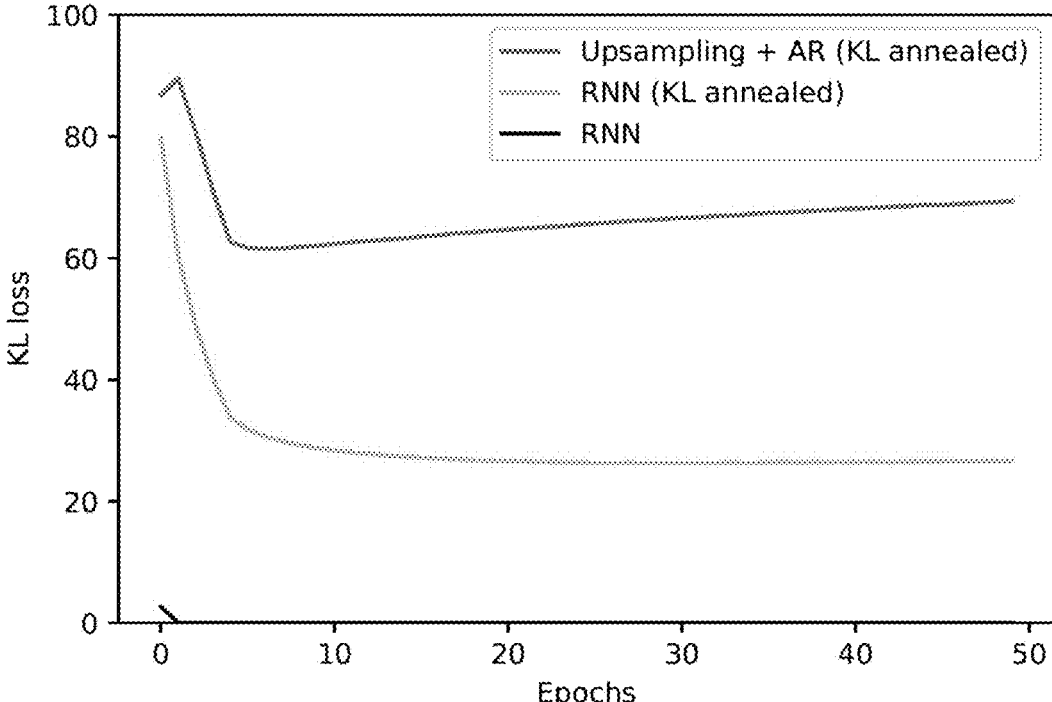

FIG. 23 illustrates the bioluminescence of LuxA variants relative to the wild-type LuxA protein as a function of the number of amino-acid substitutions (points at the bottom of the graph are below the limit of detection);

FIG. 24 illustrates the protein reconstruction accuracies for the neural network architectures "Non AR", "No up-sampling", "Reduced z" and "Up-sampling+AR";

FIG. 25 illustrates the aligned secondary structures of sequences selected at random from training set. For ease of visualisation, the proteins are first aligned using mafft, and positions in the alignment with more than 50% gaps are removed. Y-axis coordinates refer to a sequence and X-axis to amino acid positions in the sequence. Patterns along each sequence are indicated with the following color code: Alpha helix in dark blue, Coil in light blue, Gap in orange and Beta strand in red;

FIG. 26 illustrates the aligned secondary structures of sequences generated by sampling from prior of the "Non AR", "No up-sampling", "Reduced z" and "Up-sampling+ AR" models. For ease of visualisation, the proteins are first aligned using mafft, and positions in the alignment with more than 50% gaps are removed. Y-axis coordinates refer to a sequence and X-axis to amino acid positions in the sequence. Patterns along each sequence are indicated with the following color code: Alpha helix in dark blue, Coil in light blue, Gap in orange and Beta strand in red; FIG. 27 illustrates the percentage of HMM hits for samples from the "Non AR", "No up-sampling", "Reduced z" and "Up-sampling+AR" models; and FIG. 28 illustrates the evolution of KL loss term during training for the "Upsampling+AR (KL annealed)", "RNN (KL annealed)" and "RNN" models.

DETAILED DESCRIPTION OF EMBODIMENTS OF THE INVENTION

According to the invention, a generative deep neural model is used to generate protein sequences. According to embodiments, the generative deep neural model is an autoregressive neural network such as a recurrent neural network (RNN), an autoregressive convolutional neural network (autoregressive CNN), for example a variational auto-encoder (VAE) or a conditional variational auto-encoder (CVAE), or an adversarial auto-encoder (AAE) or a conditional adversarial auto-encoder (CAAE).

Still according to embodiments, the generative deep neural model comprises a probabilistic encoder and a probabilistic decoder of the variational auto-encoder type, wherein the decoder is an autoregressive decoder that may comprise an up-sampler. It has proven extremely efficient at learning high level features of complex datasets in an unsupervised fashion, and at generating novel samples with similar properties to the data they are trained on.

During training, samples of the learning dataset are encoded into latent vectors (or latent codes or latent representations) using the encoder. The latent vectors are then used to train the decoder to predict the next element in the sequence being constructed, based on previous elements of this sequence. To generate new samples, latent vectors are used to stimulate the autoregressive sequential generation of a new sample, one amino acid at a time.

According to specific embodiments, conditioning vectors comprising additional information, also referred to as conditions, are given to the encoder during the training. Such conditions typically represent characteristics of protein sequences. In such a case, both the latent vectors and the conditioning vectors are then used to train the decoder to predict the next element in the sequence being constructed, based on previous elements of this sequence. Similarly, to generate new samples, latent vectors and conditioning vectors are used to stimulate the autoregressive sequential generation of a new sample one amino acid at a time.

Variational Auto-Encoder (VAE)

As described in the article "*Tutorial on variational auto-encoders*", Doersch C., 2016, variational auto-encoders are a deep learning technique for learning latent representations. They consist in a probabilistic encoder, a probabilistic decoder, and a loss function. The probabilistic encoder is a neural network that outputs a latent representation (hidden representation) from input data, for example from an image. The dimension of the latent space is much less than the one of the input space. Likewise, the probabilistic decoder is a neural network that outputs data, for example an image, from a latent representation. The dimension of the output space is typically the same as the one of the input space.

The latent space corresponds to latent variables that may be understood as unobserved variables that capture the most salient parts of the input data used for training the variational auto-encoder. They can be thought of as a compressed version of these data.

FIG. 1$a$ and FIG. 1$b$ illustrate the logical architecture of a variational auto-encoder and of a conditional variational auto-encoder, respectively.

As illustrated in FIG. 1$a$, variational auto-encoder 100 comprises a probabilistic encoder 105 and a probabilistic decoder 110, referred to below as the encoder and the decoder, respectively. The input vector 115, denoted x, is applied to encoder 105 to generate latent vector 120, denoted z, that is in turn applied to decoder 110 to generate result 125, denoted x'. After training, output x' should be close to input x. As described above, the dimension of latent vector z is much less than that of input x and output x'.

As illustrated in FIG. 1 $b$, a main difference between a variational auto-encoder and a conditional variational auto-encoder is that additional information 130 or conditions, denoted c, is input into the encoder in addition to input vector x and in the decoder in addition to the latent representation z In a variational auto-encoder, the encoder and the decoder are jointly trained to reconstruct the sample the encoder takes as an input. During learning, the parameters of the variational auto-encoder are updated end-to-end using, for example, backpropagation with stochastic gradient descent to minimize a loss function, as described, in particular, in the article entitled "*Stochastic Backpropagation and Approximate Inference in Deep Generative Models*", Rezende D J et al., 2014, arXiv:1401.4082v3 (see e.g. § 3), as well as in the article "*Tutorial on Variational Autoencoders*", Carl Doersch, 2016, arXiv:1606.05908v2 (see e.g. § 2.2, equation 10, and the right panel of FIG. 4).

The encoder learns a distribution over the latent representation z (which typically has a reduced number of dimensions compared to the input x, as mentioned above). This leads to an information bottleneck in the variational auto-encoders, forcing them to learn an identity function in a non-trivial way and to capture high level patterns about the data. The decoder learns to predict the sample that is the most likely to be expressed by a latent code. In addition to being trained to reconstruct their inputs, variational auto-encoders are forced to learn latent representations in a space that can be decoded into valid samples. This is achieved by imposing a prior (p(z)) over the distribution of the latent representation (p(z/x)). The encoder learns the parameters of a distribution (usually normal) that is then sampled and decoded. In addition, a penalty term is used to encourage all areas of the latent space to be decoded into valid samples. The resulting model has the advantage of learning a useful latent representation of the data.

For the sake of illustration, when trained on faces, variational auto-encoders represent interpretable high level features such as hair color, having glasses or wearing a hat.

This makes it possible to condition generated examples by smart sampling of the latent space, and to perform continuous interpolations and arithmetic operations on latent vectors.

When annotations (i.e. additional information or conditions) of the training data are available, it is possible to condition the learned representation on high level features by providing this information during training to the encoder and the decoder as illustrated in FIG. 1$b$. Conditioning vector c can be seen as additional dimensions in the latent code that are not learned from the data but provided as inputs. After training, providing a latent vector and chosen conditions makes it possible to generate samples with the desired properties.

Variational Auto-Encoder Having an Autoregressive Decoder

Although variational auto-encoders effectively generate samples that capture the global structure of the data, these samples tend to be blurry. The inventors have observed that this results from each point in a generated sample being not conditioned on the other points but being only inferred from the latent space. To cope with this issue, embodiments of the invention use autoregressive decoders, for example an autoregressive decoder, in a variational auto-encoder.

Autoregressive models are used to predict the next element in a sequence, given the previous values in this sequence. The joint data distribution is modeled as a product of conditionals, as follows:

$$p(X) = \prod_{i=1}^{N} p(x_{i+1}|x_1, \dots , x_o)$$

FIG. 2a and FIG. 2b illustrate an example of the logical architecture of a conditional variational auto-encoder having an autoregressive decoder, used during the training phase and for generating new protein sequences, respectively.

As illustrated in FIG. 2a, conditional variational auto-encoder 200 comprises a probabilistic encoder 205 and a probabilistic autoregressive decoder 210, referred to as the encoder and the decoder, respectively, in the following. The input vector 215, denoted x, as well as additional information 220 or conditions, denoted c, are applied to encoder 205 to generate latent vector 225, denoted z. Encoder 205 may be similar to encoder 105 described in reference to FIG. 1b. An example of encoder 205 is illustrated in FIG. 3.

For the sake of illustration, additional information 220 may comprise the length of the protein, its charge, its isoelectric point, its molar extinction coefficient, its solubility (e.g. probability of expression in *E.coli* inclusion bodies: the smaller this quantity, the more soluble the protein is), and/or its molecular weight, it being observed that some of these values may be correlated (for example, the molecular weight of a protein is highly correlated with its length).

According to the illustrated example, latent vector 225 and additional information 220 are then applied to up-sampler 230 to generate up-sampled latent vector 235, denoted z'. Latent representation z is up-sampled in up-sampler 230 while being conditioned by additional information c to generate latent representation z'. The obtained up-sampled latent vector 235, i.e. latent representation z', and input vector x are then input in autoregressive module 240 to generated result 245, denoted x'.

It is to be noted that although an up-sampling module is used in most of the illustrated examples, it is not requested in all embodiments. For example, the size of the latent code z may be increased by concatenation to reach the one of input vector x.

A more detailed example of autoregressive decoder 210 is described by reference to FIGS. 4a, 4b, 5a, and 5b.

It is to be noted that according to particular embodiments, no additional information is fed into encoder 205 and up-sampler 230.

As illustrated in FIG. 2b, only the decoder, comprising up-sampler 230 and autoregressive module 240, is used for generating a protein sequence from a latent vector, additional information (conditions), and previously determined amino acids of the sequence being generated (x).

According to embodiments, encoder 205 and autoregressive decoder 210 comprise convolutional layers, with strided convolutions for down-sampling in the encoder and transposed convolution for up-sampling in the decoder. The kernel size of the convolutional layers is preferably set to two.

Still according to embodiments, all convolutional layers are followed by batch normalization and a parametric rectified linear unit (PReLU) activation (unless otherwise specified, in particular in description of FIGS. 3, 4a, 4b, 5a and 5b). Indeed, batch normalization has been very effective at improving both the training speed and the reconstruction performance of the network. Dense layers are preferably followed by PReLU activation, except those that output the parameters of the Gaussian distribution learned by the encoder $\mu(x,c)$ (no activation) and $\sigma(x,c)$ (softplus activation). Activations and batch normalization are not shown in FIGS. 3, 4a, 4b, 5a, and 5b to make them easier to read.

As described by reference to FIG. 5b, autoregressive decoder 210 makes use of gated activation functions, for example the gated activation functions described in "*Wave-Net: A Generative Model for Raw Audio*", van den Oord A et al., 2016, arXiv:1609.03499v2 (see e.g. § 2.3, equation 2). Feature maps of convolutional layers may be split in two parts and two different activation functions may be applied on each half, followed by elementwise multiplication. The result is convolved upon and passed to the next stack, as well as kept to be used in skip connections.

FIG. 3 illustrates an example of the functional architecture of encoder 205 illustrated in FIG. 2a. It is to be noted that other functional architectures may be implemented.

As illustrated, input vector x is fed in five successive 1D convolution layers referenced 300-1 to 300-5 (for the sake of clarity only two of them are represented). According to embodiments, the stride of these convolution layers is set to two, except for the first one which is set to one. The output of 1D convolution layer 300-5 is flattened (reference 305) so as to suppress one dimension. The convolution layers aim at establishing relations between parts of protein sequences.

In parallel, additional information or conditions c are fed into two successive dense layers 310-1 and 310-2, i.e. into two fully connected neural networks that aim at identifying what should be in protein sequences.

The output of flattened layer 305 and the output of dense layer 310-2 are then concatenated (reference 315). As illustrated, the result of the concatenation is fed into two successive dense layers 320-1 and 320-2, the result of the latter being fed into dense layers 325 and 330. Again, these fully connected neural networks aim at identifying what should be in protein sequences, taking into account the conditions.

The output of dense layer 330 is then used as input of a stochastic layer comprising an activation function 335, for example the softplus activation function, the square root function 340, and the application of a Gaussian function (references 345 and 350).

The output of the stochastic layer is added (reference 355) to the output of dense layer 325 to create latent representation z It is thus observed that the output of the encoder being stochastic (a Gaussian parametrized by the neural network), it has an additional input: random standard Gaussian noise.

This makes it possible to backpropagate the gradients of the loss through the stochastic layer.

It is also to be noted that an encoder similar to the one illustrated in FIG. 3 may be used when no additional information is used. In such a case, dense layers 310-1 and 310-2 are not implemented (as well as concatenation function 315).

FIG. 4a and FIG. 4b illustrate an example of the functional architecture of autoregressive decoder 210 illustrated in FIGS. 2a and 2b, during training and during generation, respectively. Again, it is to be noted that other functional architectures may be implemented.

As described in reference to FIGS. 2a and 2b and according to the given example, autoregressive decoder 210 comprises up-sampler 230 and autoregressive module 240.

Up-sampler 230 generates up-sampled latent vector z' from latent vector z and additional information c. An example of the functional architecture of up-sampler 230 is described in reference with FIG. 5a. Again, it is to be noted that up-sampler 230 is not required for carrying out the invention.

Up-sampled latent vector z' is fed into a set of network blocks, for example a set of K network blocks of the WaveNet type, as illustrated. Such a type of network block is described, for example, in the paper entitled "*WaveNet: A Generative Model for Raw Audio*", van den Oord A et al., 2016, arXiv:1609.03499v2 (see e.g. § 2.4).

As illustrated in FIG. 4a, during learning, input vector x is fed into the first network block of which the output is fed into the second network block and so on until the last one. As described above, input vector x represents the input protein sequence and output vector x' its reconstruction.

When generating a protein sequence from a latent representation and conditions, input vector x is initialized to zeros and previously determined amino acids of the sequence being generated (x') are fed into the first network block of which the output is fed into the second network block and so on until the last one, as illustrated in FIG. 4b. Sequentially, a reconstructed protein sequence is obtained by predicting the next amino acid in the sequence, as described in reference to Algorithm 1 given in the Appendix. At each step, an amino acid is predicted, added to input vector x, so that the next one can be predicted.

As described by reference to FIG. 5b, the output of network block k is transmitted to network block k+1 and is kept to be added later to other residual connections.

Turning back to FIGS. 4a and 4b, the outputs of network blocks 400-k are combined (reference 405) and filtered in convolution layer 410 that output is normalized (reference 415), for example using the softmax function, to generate output x'. An example of such an output is described by reference to FIG. 7.

FIG. 5a illustrates an example of the functional architecture of up-sampler 230 illustrated in FIGS. 2a, 2b, 4a, and 4b. Again, it is to be noted that other functional architectures may be implemented.

The up-sampler comprises two parts whose results are concatenated.

As illustrated, latent vector z, which may be obtained from the decoder during training or that may be obtained from another way, typically from a user, for generating new protein sequences, is fed into dense layer 500 to be up-sampled by a fully connected artificial neural network. The output of the latter is reshaped (reference 505) so as to add one dimension before being fed into four successive 1D deconvolution layers referenced 510-1 to 510-4 (for the sake of clarity only two of them are represented). The deconvolution layers add information about where something should be in the protein sequence while the fully connected neural network adds information about what should be in the protein sequence.

It is to be noted that a 1D deconvolution layer is to a 2D deconvolution layer the same as what a 1D convolution layer is to a 2D convolution layer. In other words, it is a 2D deconvolution layer applied on a 1D input to which one additional dimension has been added. For example, a tensor of shape (75, 21) is reshaped into (75, 1, 21) before being passed in the 2D deconvolution layer, thus becoming (150, 1, 21), which is finally reshaped into (150, 21).

In parallel, latent vector z is concatenated (reference 515) with additional information or conditions c. The result of this concatenation is fed into dense layer 520 the output of which being reshaped (reference 525) so as to add one dimension. Again, the fully connected neural network adds information about what should be in the protein sequence, taking into account the conditions.

Next, the output of 1D deconvolution layer 510-4 and of dense layer 520 (after it has been reshaped, reference 525) are concatenated (reference 530) to generate up-sampled latent vector z'.

FIG. 5b illustrates an example of the functional architecture of the network blocks of autoregressive module 240 illustrated in FIGS. 2a, 2b, 4a, and 4b. Again, it is to be noted that other functional architectures may be implemented. For the sake of illustration, only one network block (400-k) is illustrated.

Up-sampled latent vector z', obtained from up-sampler 230, is fed into convolution layer 550.

In parallel, the (k−1) first values of the input vector x (during training) or of the protein sequence being generated, denoted $x^{(k)}$, are fed into two successive causal convolution layers 555-1 and 555-2, the dilation factor of the causal convolution being, for example, doubled each time so that the receptive field of the autoregressive model grows exponentially with the number of WaveNet-like stacks. After three stacks, a value that is advantageously used, the receptive field is 32 (each of the three network block comprising two blocks of causal convolution, which means six causal convolutional layers).

The output of convolution layer 550 and that of causal convolution layer 555-2 are added (reference 560) and an activation function is applied on the result (reference 565). For the sake of illustration, σ represents the sigmoid activation function. A gated activation may be used, for example the one described in the paper entitled "*WaveNet: A Generative Model for Raw Audio*", van den Oord A et al., 2016, arXiv:1609.03499v2 (see e.g. § 2.3, equation 2).

The output of the activation function is then combined (reference 570) with the addition of the output of convolution layer 550 and of causal convolution layer 555-2 and the obtained result is fed into convolution layer 575 to update the protein sequence being reconstructed or generated with the $k^{th}$ prediction.

The output of convolution layer 575 (i.e. $x^{(k+1)}$) is both passed to the $(k+1)^{th}$ network block (i.e. network block 400-(k+1)) and kept to be added later to the other residual connections. As described in the paper entitled "*WaveNet: A Generative Model for Raw Audio*", van den Oord A et al., 2016, arXiv:1609.03499v2 (see e.g. § 2.4), these residual connections reduce the vanishing gradient problem, making training easier.

The output of network blocks 400-1 to 400-K are combined (reference 405) and filtered in convolution layer 410 of which the output is normalized (reference 415), for example using the softmax function, to generate output x'.

Algorithm 1 given in the appendix illustrates an example of steps for generating protein sequences. As illustrated, each amino acid is determined one after the other in a loop the size of which may be determined by the length of the protein to be generated. At each iteration, a probability is determined for each amino acid to be the one used to generate the protein sequence. As described above, it is based on a latent code, on conditions, and on the probabilities associated with each amino acid in the protein sequence for the positions preceding the one that is processed. In this example, the amino acid that is selected, at a given position, is the one of higher probability. Other methods may be used. For example, sequence variants may be generated by choosing amino acids that do not have the highest probability but, for instance, choosing the second most probable amino acid.

Turning back to FIG. 2a, variational auto-encoder 200 may be trained by minimizing the variational lower bound, as described in the paper entitled "Auto-Encoding Variational Bayes", Kingma D P et al., 2013, arXiv:1312.6114v10 (see e.g. § 2, in particular § 2.2. to § 2.4). Accordingly, the loss function preferably comprises a cross-entropy term and a Kullback-Leibler divergence term. The cross-entropy is minimum when the model predicts the right amino acid with a probability of 1 and gives a probability of 0 to all other amino acids. The Kullback-Leibler divergence is a regularization-like term that is minimum when the data projected onto the latent space follows a standard normal distribution. According to particular embodiments, the loss function is minimized using the Adam optimization algorithm mentioned above, with default parameters for 50 epochs.

FIG. 6 illustrates an example of steps of a method for generating a protein sequence with an autoregressive neural network such as the conditional variational auto-encoder illustrated in FIGS. 2a and 2b or a (conditional) adversarial auto-encoder.

As illustrated, a first step (step 600) is directed to obtaining a training dataset comprising protein sequences and, preferably, associated conditions. This training set is used to train the autoregressive neural network (step 605) until a loss error reached a threshold denoted θ error (step 610).

Step 605 comprises steps 615 to 650 described hereafter.

After training, a latent code and, preferably, associated conditions are obtained (step 615) and an index i representing a location within the protein sequence to be generated is initialized to 1 (step 620). Likewise, other variables are initialized, such as the probability for each amino acid to be selected at a given position of the sequence being generated.

If needed (as suggested with dotted line), the obtained latent code and conditions (if any) are up-sampled (step 625).

Then, the latent code and conditions (if any) or the up-sampled latent code and conditions (if any) as well as the probabilities previously obtained (i.e. if index i is greater than one) are input in the autoregressive module (step 630) for obtaining probabilities for amino acids to be selected at position i in the generated sequence (step 635).

Next, index i is incremented by one (step 640) and a test is carried out to determine whether or not the value of index i has reached the length of the protein sequence to be generated (step 645), i.e. to determine whether or not probabilities have been obtained for each location of the protein sequence to be generated, or whether or not another criterion is reached, indicating that the protein sequence has been generated. Such a criterion may be for example the selection of padding character instead of an amino acid for position i of the protein sequence.

If index i has not reached the length of the protein sequence to be generated or if the criterion is not reached, steps 630 to 645 are repeated.

On the contrary, if index i has reached the length of the protein sequence to be generated or if the criterion is reached, a protein sequence is generated as a function of the obtained probabilities (step 650). As mentioned above, for each location of the protein sequence, the amino acid associated with the higher probability may be selected.

Training such a neural network can be seen as unsupervised as the model is simply learning to reconstruct samples from the dataset while passing through an informational bottleneck. A variant of this training procedure is possible where in addition to performing reconstruction, the model is also asked to predict certain properties related to the protein. An error term reflecting how well these predictions are made can then be added to the loss function. Training such a model could be described as semi-supervised.

Generating Protein Sequences

The data used for training the variational auto-encoder 200 may be obtained from the databases known as InterPro and UniPro.

For the sake of illustration, all luciferase-like proteins (containing the Interpro domain IPR011251) having a length smaller than 600 amino acids may be chosen. There are about 72,000 of them. Some of these proteins have an easily testable activity: they emit light. Furthermore, the UniProt SPARQL endpoint may be queried to retrieve additional information about the sequences (such as Interpro families). The obtained sequences are advantageously padded with spaces at the end so that they all have the same length, for example a length of 600 amino acids. Still for the sake of illustration, the obtained sequences can be one-hot-encoded into matrices of shape 600×21 (20 amino acid, plus the padding character). Additional protein properties mays be obtained, for example they may be computed with the EMBOSS 'pepstats' software.

Accuracy

After being trained with such a luciferase-like protein dataset, variational auto-encoder 200 may predict the next amino acid in the sequence (based on the previous amino acids, the latent representation, and the conditions) with an 85.5% test accuracy. The variational auto-encoder being autoregressive, it learns quickly that after a padding character comes another one. It is almost 100% accurate at predicting padding characters and predicts the next amino acid in a sequence with a 78% accuracy.

A good accuracy of the reconstructions (i.e. protein sequence x' generated by the decoder in an autoregressive fashion from projection z of protein x, given conditions c, as described by reference to Algorithm 1 and FIG. 2b) is also obtained. The decoder generates sequence x' one amino acid at a time, the next amino acid in the sequence being predicted based on the previous predictions rather than on the input sequence (x). The accuracy of reconstructions is 82.5% overall, and 75% on the amino acid sequence (excluding padding). It is to be noted that these accuracies are lower than the test accuracy mentioned above, as errors accumulate during the reconstruction process.

FIG. 7 and table 1 in the Appendix illustrate protein reconstruction.

FIG. 7 illustrates a conditional probability distribution table wherein the probability of each amino acid is computed as a function of the previous amino acids and of the up-sampled latent vector z'. As illustrated, the most likely amino acid is added to the sequence which is constructed one amino acid at a time. For example, amino acid G (glycine) in the eighteenth position of the protein sequence is the one having the higher probability. Accordingly, it is selected as belonging to the protein sequence represented on top of the conditional probability distribution table.

Table 1 in the Appendix illustrates the alignments between a protein sequence used as input (denoted init) and the corresponding reconstructed protein sequence (denoted recons). In this example, the protein sequence that is used as input is Pyrimidine monooxygenase (RutA, UniProt ID: A1JMY1). (*) indicate identical amino acids, (:) very similar amino acids, and (.) similar amino acids.

Validity of Generated Protein Sequences

It is to be noted that to encode valid proteins, generated sequences should start with a methionine (M) (as all proteins from the dataset do) and must not have padding characters between amino acids. Out of 80,000 sequences randomly sampled from the latent space, 99.6% were valid. After having obtained these sequences, it has been assessed whether generated proteins would be found to have significant homologies to proteins present in the dataset. To that end, the HMM profile of the bacterial luciferase-like PFAM family (PF00296) have been used to identify generated proteins. As a result, 30% of the generated sequences were recognized as belonging to this family (E-value<0.1).

Table 2 in the Appendix illustrates alignment between a generated protein randomly sampled from the latent space and the most similar known sequence (glucose-6-phosphate dehydrogenase, F420-dependent, UniProt ID: D9VBX0). The latter is identified with HMMER. Again, (*) indicate identical amino acids, (:) very similar amino acids, and (.) similar amino acids.

During training, the Kullback-Leibler divergence term pushes the data projected onto the latent space to follow a standard normal distribution. However, this is not perfect and some regions of the latent space are left "empty". When sampling the latent space using a normal distribution to generate new proteins, points in the latent space that are too distant from actual projections might not be well decoded, explaining why a substantial number of the sequences generated above are not recognized as part of the PF00296 family. In contrast, reconstructions from projected points are almost always valid. As an example, 10,000 proteins from the dataset have been projected and reconstructed and it has been found that 95% of the reconstructed proteins were identified as part of the PF00296 family.

Distribution of N-Grams

It is observed that the distribution of amino acids in the generated sequences should match the natural distribution of amino acids in the dataset used for the training. As illustrated on graphs A and B in FIG. 8, the generative network is able to reproduce this distribution, but it tends to exaggerate it by predicting abundant amino acids such as Alanine (A) too frequently and rare amino acids such as Cysteine (C) not frequently enough. This is a common problem for classification tasks where categories have an imbalanced number of samples. This problem can be solved by weighting the loss associated with each class according to its abundance.

Beyond global amino acid frequencies, the network should also learn what amino acids usually follow other amino acids. The luciferase-like dataset contains 8,397 unique trigrams (3-mers). Their frequency in the dataset has been compared to their frequency in generated proteins. While the frequencies are nicely correlated, it has been observed, as illustrated on graph C in FIG. 8, the same tendency of the variational auto-encoder to produce abundant trigrams too frequently.

As mentioned above, FIG. 8 makes it possible to compare the distribution of amino acids in generated sequences with patterns of amino acid occurrences of the training dataset. Graph A illustrates the distribution of the occurrence frequencies of amino acids in luciferase-like sequences, graph B illustrates the distribution of the occurrence frequencies of amino acids in generated sequences, and graph C illustrates the comparison of the occurrence log frequencies of the 8,397 trigrams in each dataset.

Higher Level Structures of Reconstructed Proteins

While preserving features of the primary structure such as 3-mers frequencies is of importance, the variational auto-encoder should also understand aspects of secondary and tertiary structures. To investigate this, nine reconstructions of a F420-dependent glucose-6-phosphate dehydrogenase protein (UniProt ID: A6W D69), which displayed low sequence identity to the initial protein (40-48%), have been selected. If the variational auto-encoder has some understanding of protein structure, it is expected that it preserves structure even when the primary sequence diverges, by selecting amino acids that will maintain a structure similar to that of the initial protein. For the sake of illustration, secondary structure predictions have been made with PSIPRED (Protein Sequence Analysis Workbench aggregating several UCL structure prediction methods into one location) and 3D structures have been predicted using Protein Homology/analogY Recognition Engine v 2.0 (Phyre2).

FIG. 9 illustrates preservation of secondary structures in reconstructions by showing alignments between one protein (Uniprot: A6WD69, denoted init in FIG. 9) and its reconstructions (denoted 0 to 7 in FIG. 9). Secondary structures as predicted by PSIPRED are highlighted as follow: Alpha helices are colored in purple, and beta sheets in yellow. Bold amino acids are the highly conserved positions from the HMM profile of Bacterial Luciferase (PF00296). Again, (*) indicate identical amino acids, (:) very similar amino acids and (.) similar amino acids.

It is apparent from FIG. 9 that even divergent sequences reconstructed from the same point in the latent space tend to keep the same secondary structure as predicted by PSIPRED. Even with a reconstruction accuracy as low as 40%, the variational auto-encoder preserves the structure of the protein. All beta sheets and alpha helices roughly begin and start at the same place on both sequences. Phyre2 also predicts almost identical 3D structures for the initial and reconstructed proteins, as apparent from FIG. 10.

FIG. 10 illustrates 3D structures of the two proteins as predicted by Phyre2 for the initial protein (A) and for one of its reconstructions presented in FIG. 9(B).

Amino Acid Relatedness

Amino acids having similar properties (e.g. charge, polarity, or hydrophobicity) are more likely to preserve the activity and folding of the protein when swapped in a sequence. These similarities are usually represented in the form of a BLOSUM matrix (blocks substitution matrix). As apparent from FIG. 7, the variational auto-encoder seems to learn which amino acids can be swapped as seen by the fact that the few positions in a reconstructed protein that are different from the initial protein are usually very similar amino acids. This may be confirmed by comparing the knowledge obtained by the variational auto-encoder to the BLOSUM62 matrix. As mentioned above, the decoder predicts the probability that each amino acid will occupy a given position. According to embodiments, the chosen amino acid is the one with the highest probability but the other probabilities can be used to study how similar two amino acids are according to the variational auto-encoder and compute a BLOSUM-like matrix. For instance, it is expected that the probabilities for Leucine (L) and Isoleucine (I) to be relatively high when Valine (V) is predicted, since they all have hydrophobic side chains.

Algorithm 2 in the Appendix illustrates an example of steps for computing a BLOSUM-like matrix.

FIG. 11 illustrates a BLOSUM62 matrix (left) and BLOSUM-like generated matrix (right). Red indicates that high likelihood that these amino acids can be swapped and blue a low likelihood.

While the general aspect of the two matrices is different, it can be seen that the variational auto-encoder does correctly identify many of the similarities and dissimilarities between amino acids, with the notable exception of W and Y which the variational auto-encoder does not predict as easily swappable but are identified as such by the BLOSUM62 matrix. The variational auto-encoder thus learns what amino acids are related since they tend to appear in similar contexts, simply by being trained to perform reconstructions.

Conditioning

The encoder having a stochastic output (it predicts a distribution over the latent variables), the variational auto-encoder can reconstruct a given sequence in a variety of ways.

As described above, conditioning essentially consists in adding additional information to the encoder and to the decoder, which can then be used to control the generation process beyond random sampling. For the sake of illustration, the following additional information has been used as a conditioning vector (c): the length of the protein, its weight, charge, isoelectric point, molar extinction coefficient and probability of expression in inclusion bodies (a measure of solubility). These properties were computed using the pepstats tool from the EMBOSS suite. Interestingly, the information provided in conditioning vector c enabled a 2% gain in reconstruction accuracy.

To test the ability of the variational auto-encoder to condition on these properties, conditioning values have been modified linearly from −2 to +2 one at a time (quantities are standard scaled), while keeping the other values unchanged. For each set of conditioning values, 32 points have been randomly sampled in the latent space and the corresponding protein sequences have been generated. This enabled proteins to be generated which have, on average, chosen physical properties. This is exemplified, in particular, in FIG. 12 where solubility has been modified. It is to be noted that properties that are strongly linked physically such as molecular weight and length cannot be conditioned upon separately, but conditioning is still possible when both are changed in the same direction. These experiments show that it is possible to generate sequences that have chosen physical properties.

FIGS. 12 to 16 illustrate generation of protein sequences when conditioned on solubility, protein length, protein length and weight, charge, and molar extinction coefficient, respectively. As mentioned above, proteins were generated while progressively changing the considered one(s) of these parameters from −2 to 2 and keeping the other physical properties unchanged.

Figure 12:
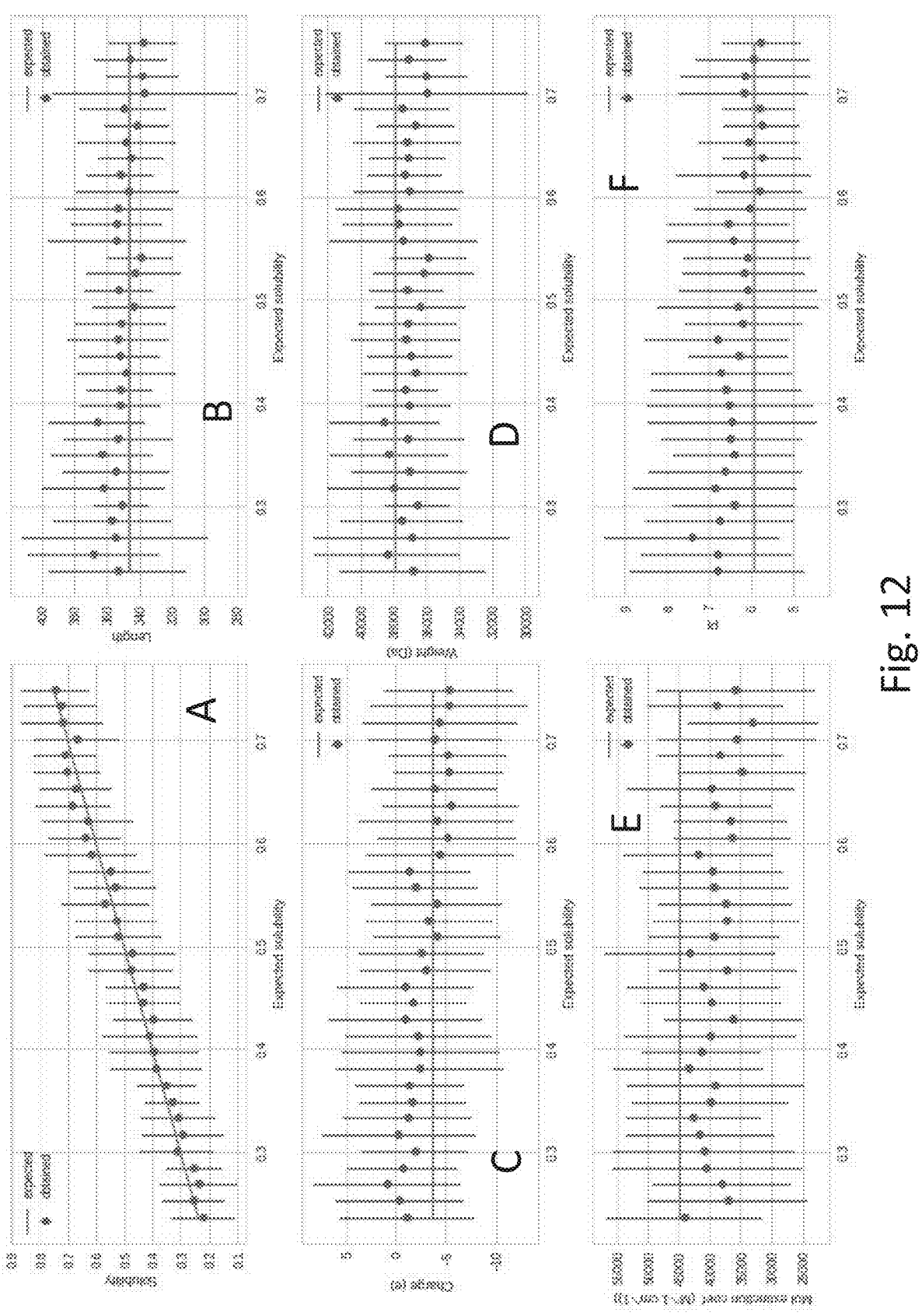
Figure 13:
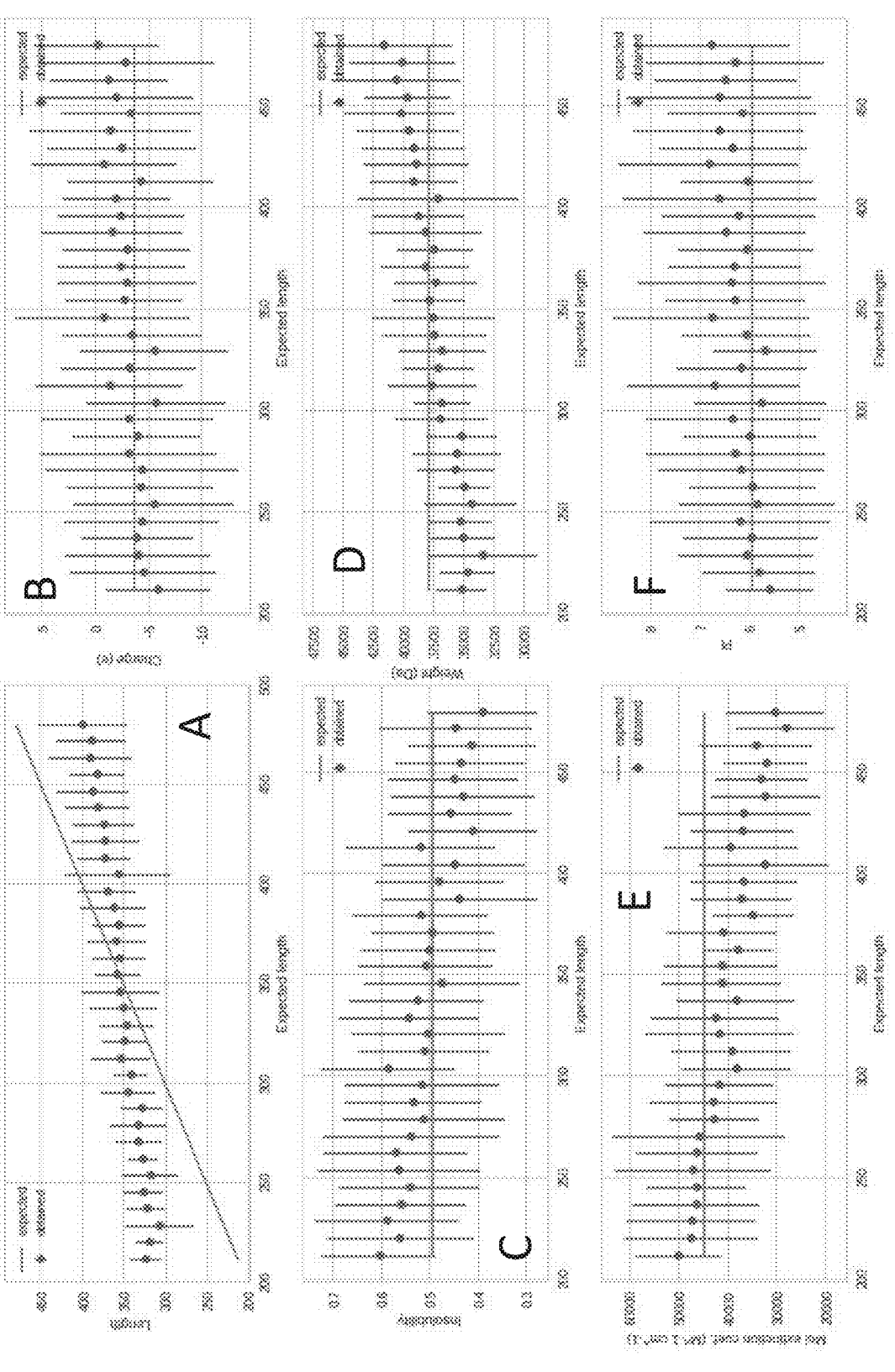
Figure 14:
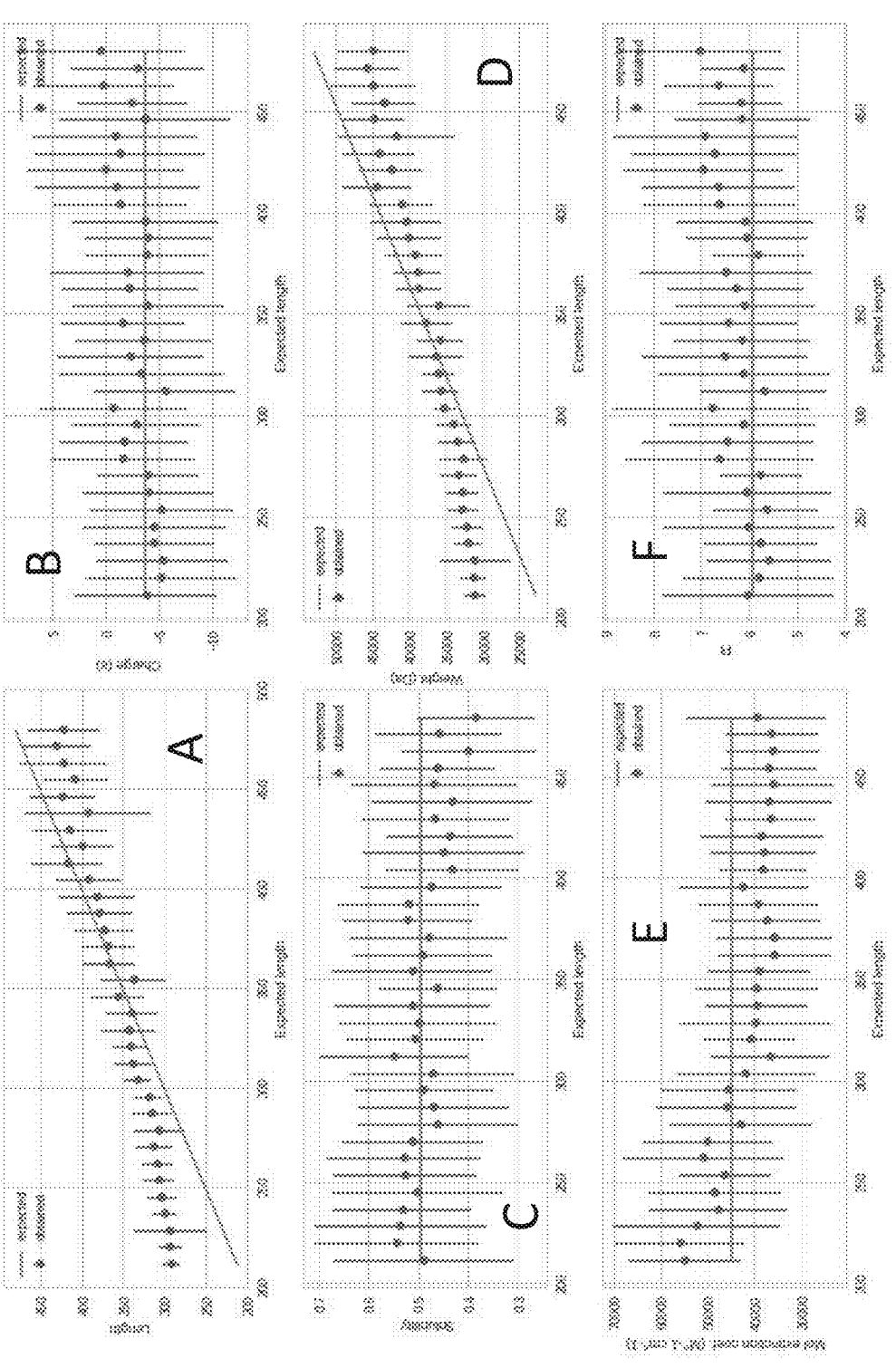
Figure 15:
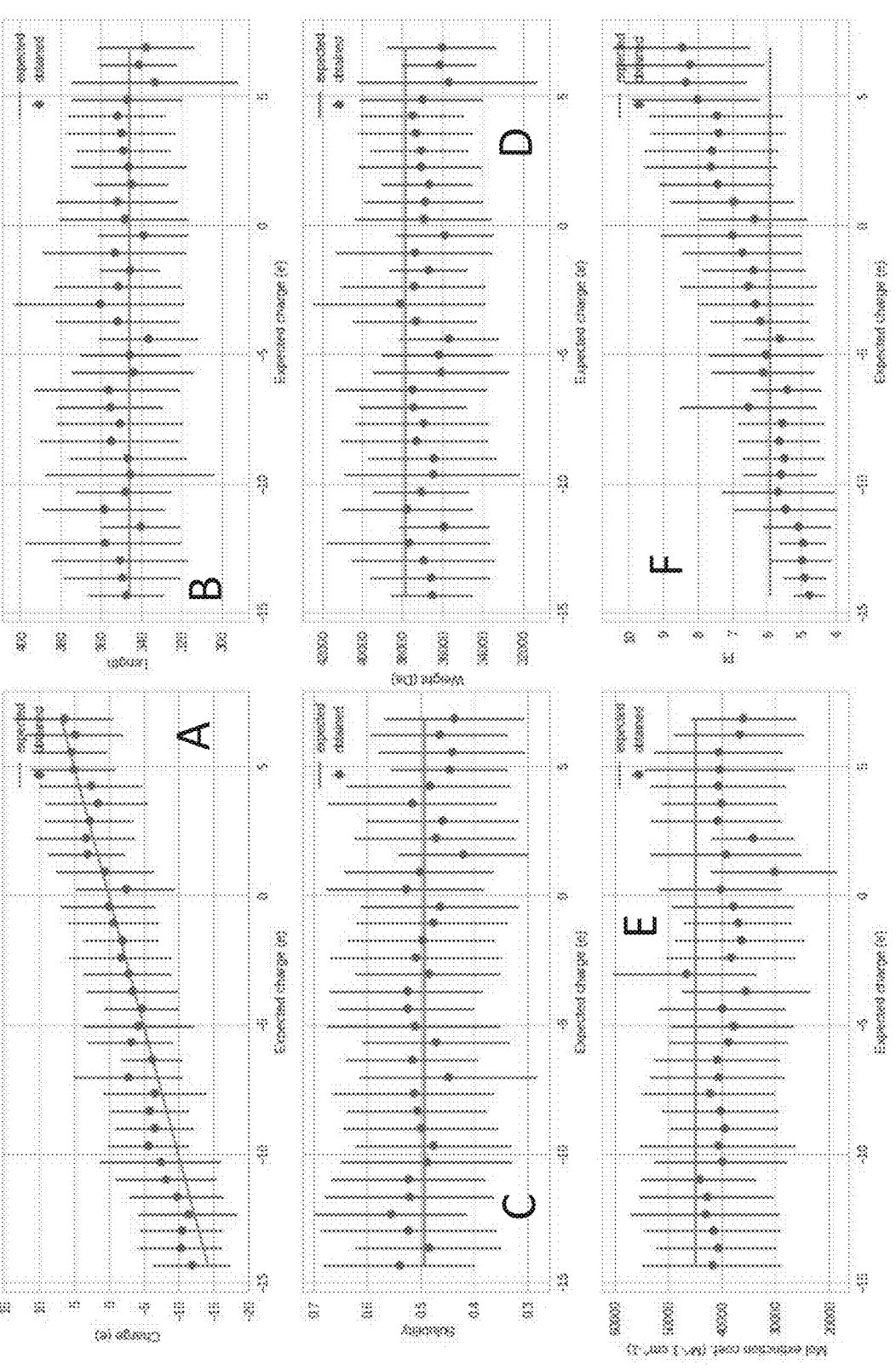
Figure 16:
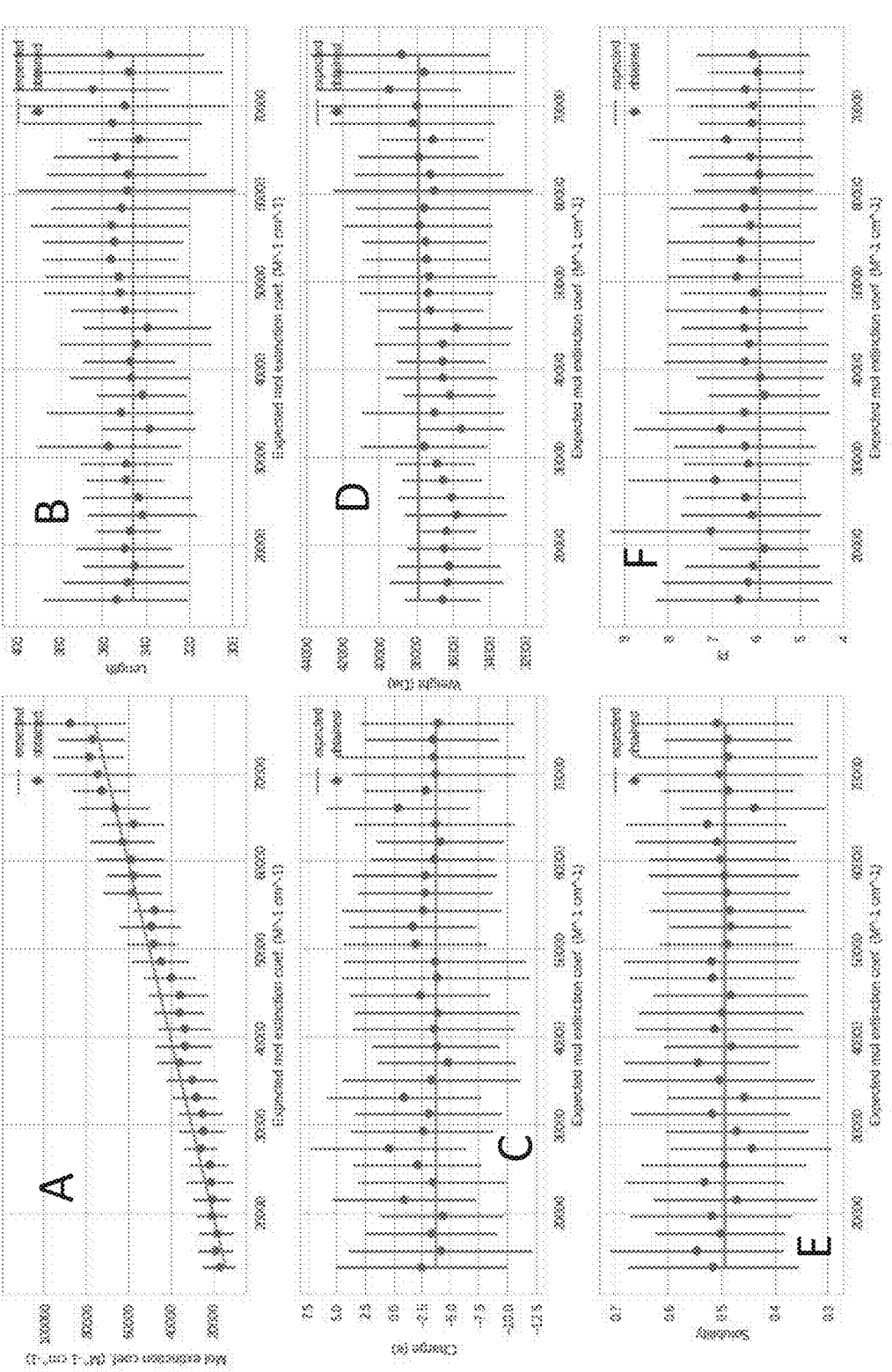

In FIG. 12,
graph A represents solubility variation,
graph B represents length variation,
graph C represents charge variation, graph D represents weight variation,
graph E represents molar extinction coefficient variation, and
graph F represents isoelectric point (P1) variation.
In FIG. 13,
graph A represents length variation,
graph B represents charge variation,
graph C represents insolubility variation,
graph D represents weight variation,
graph E represents molar extinction coefficient variation, and
graph F represents isoelectric point (P1) variation.
In FIG. 14,
graph A represents length variation,
graph B represents charge variation,
graph C represents solubility variation,
graph D represents weight variation,
graph E represents molar extinction coefficient variation, and
graph F represents isoelectric point (P1) variation.
In FIG. 15,
graph A represents charge variation,
graph B represents length variation,
graph C represents solubility variation,
graph D represents weight variation,
graph E represents molar extinction coefficient variation, and
graph F represents isoelectric point (P1) variation.
In FIG. 16,
graph A represents molar extinction coefficient variation,
graph B represents length variation,
graph C represents charge variation,
graph D represents weight variation,
graph E represents solubility variation, and
graph F represents isoelectric point (PI) variation.

The green line represents the value provided in the conditioning vector. 32 proteins were generated for each set of values. The points represent the mean and bars represent the standard deviation.

For the sake of illustration and to obtain variants of a specific protein with modified properties, an F420-dependent glucose-6-phosphate dehydrogenase was chosen and 100 different reconstructions were generated by sampling the latent space while conditioning for increased solubility, protein length, protein length and weight, charge, and molar extinction coefficient.

Regarding solubility, as expected, conditioned proteins had increased solubility on average, although not as much as expected if conditioning worked perfectly. Further, it was observed that conditioning on solubility did not affect other physical properties. Reconstructed sequences were on average 95% identical to the initial sequence, and the accuracy only dropped to 94% when conditioning.

FIG. 17 illustrates generation of variants of a protein with desired properties. Reconstructions of a F420-dependent glucose-6-phosphate dehydrogenase are generated while conditioning for increased solubility (decreased insolubility). The distributions over all the six physical properties (graph A: weight, graph B: charge, graph C: isoelectric point (PI), graph D: molar extinction coefficient, graph E: length, and graph F: insolubility) of 100 reconstructions are shown:
    blue shapes illustrate the distribution over the whole dataset,
    green shapes illustrate the distribution over 100 reconstructions of the input protein, red shapes illustrate the distribution over 100 modified
    reconstructions of the input protein (conditioning with
    insolubility=0.39),
purple shapes illustrate the distribution over 100 modified
    reconstructions of the input protein (conditioning with
    insolubility=0.22),
green lines represent the expected value for all recon-
    structions,
the red line is the expected insolubility for the insolubility
    red shape, and
purple line is the expected insolubility for the insolubility
    purple shape.

Latent Space Organization

When training the variational auto-encoder without con-
ditioning, it may be observed that physical properties are
encoded in the latent space, the principal component corre-
sponding mostly to the protein size.

FIG. 18 illustrates the projection of the training set in the
latent space of an unconditioned model, colored as a func-
tion of the protein length. The x-axis is the projection on the
first principal component (PC) and the y-axis is that on the
second principal component (PC).

Conditioning should in theory provide this physical infor-
mation to the variational auto-encoder and thus free the
latent space to encode other properties of the proteins.
Indeed, in the variational auto-encoder trained with condi-
tioning, it becomes impossible to predict protein size and the
other properties from the latent space representation.

The latent space self-organizes so that proteins from the
same families cluster together. For the sake of illustration,
the luciferase-like domain (IPR011251) combines 88 Inter-
pro families containing proteins with related functions,
similarities in sequence, or similar secondary or tertiary
structure. In the dataset described above, there are 24
non-overlapping Interpro families containing more than 100
samples. These 24 families are relatively balanced and
represent about 50,000 samples. Training a simple multi-
class logistic regression model on top of the latent repre-
sentation of the 50,000 annotated samples makes it possible
to classify proteins with a 92.7% accuracy. This shows that
families are generally well separated in the latent space,
which can be visualized in a projection.

Generating Protein Sequences: Example, Generation of
LuxA Variants

To experimentally validate the ability of a conditional
variational auto-encoder (CVAE) having an autoregressive
decoder as illustrated in FIGS. 2a to 5b, to generate func-
tional protein variants according to the method illustrated in
FIG. 6, variants of the LuxA protein from *Photorhabdus
luminescens* (Uniprot P19839) were generated by randomly
sampling the latent space around the representation of LuxA
and decoding these points into protein sequences using the
autoregressive decoder.

First, the CVAE was trained on 72,000 luciferase-like
proteins (containing the Interpro domain IPR011251) with
conditioning values corresponding to the following physical
properties obtained from the EMBOSS 'pepstats' software
(https://www.ebi.ac.uk/Tools/seqstats/emboss_pepstats/):
length of the protein (Residues), its molecular weight,
charge, isoelectric Point, A280 molar extinction coefficients
and probability of expression in inclusion bodies. These
conditioning values were not changed during the generation
process of LuxA variants, they were kept to the values of the
LuxA protein. The process for the generation corresponds to
what is illustrated in FIG. 4b, where the latent vector z was
sampled from the distribution defined by the projection of
the LuxA protein in the latent space. The variational autoencoder doesn't simply learn a point in a latent space, it
actually learns a normal distribution defined by two terms,
a mean and a variance. This distribution was simply sampled
to generate the variants of LuxA.

A set of 23 protein variants (SEQ ID NO: 30 to 52) more
or less distant from the LuxA primary sequence spanning
between 11 and 34 amino acid differences were chosen
arbitrarily (Table 3). None of the variants generated
belonged to the training set.

DNA sequences encoding these proteins were synthesized
(SEQ ID NO: 53 to 75) and cloned on an expression vector
designed to carry a bicistronic device in order to ensure that
all variants are expressed at the same level (Mutalik et al,
2013 *"Precise and reliable gene expression via standard
transcription and translation initiation elements."* Nat.
Methods 10: 354-360). The resulting plasmids were trans-
formed in an *E. coli* strain expressing luxCDBE from
another vector.

Bacterial Strains and Growth Conditions.

*E. coli* DH5 alpha, used as a host for recombinant
plasmids, was grown in LB media at 37° C. with shaking at
200 rpm. kanamycin (50 µg/ml) and chloramphenicol (20
µg/mL) were added to the medium to prevent loss of
plasmids derived from pCM17 (luxCDABE) and pFD69
(pFAB3905ΩP14BCD1cat).

Construction of Plasmids

The luxA gene was deleted from plasmid pCM17 express-
ing the luxCDABE operon (Rhee et al, 2011 *"Determination
of spatial and temporal colonization of enteropathogenic E.
coli and enterohemorrhagic E. coli in mice using biolumi-
nescent in vivo imaging."* Gut Microbes 2: 34-41). by
amplification using primers B731/LC545 (SEQ ID NO: 14
and 16) and B732/LC327 (SEQ ID NO: 15 and 17), fol-
lowed by Gibson assembly (Gibson et al, 2009 *"Enzymatic
assembly of DNA molecules up to several hundred kilo-
bases."* Nat Methods 6: 343-5) of the two PCR fragments,
giving plasmid pDB283 (pCM17ΩΔluxA) (SEQ ID NO:
77).

The kanamycin gene of pFAB3905 (P14BCD1, KmR)
(Mutalik et al, 2013) was replaced by the cat gene to allow
the complementation by luxA in *E. coli* DH5/pDB283
(pCM17ΩΔluxA) which is already resistant to kanamycin.
For this construction, the cat gene was amplified from
pZA31-luc (Lutz & Bujard, 1997 *"Independent and tight
regulation of transcriptional units in Escherichia coli via the
LacR/O, the TetR/O and AraC/I1-I2 regulatory elements."*
Nucleic Acids Res 25: 1203-1210) using primers F168/F169
(SEQ ID NO: 18 and 19) and assembled with primers
F170/F171 (SEQ ID NO: 20 and 21) under the control of a
P14BCD1 constitutive promoter in plasmid pFAB3905 giv-
ing plasmid pFD69 (pFAB3905ΩP14BCD1 cat). The luxA
gene was amplified from pCM17 (luxCDABE) using prim-
ers F172/F173 (SEQ ID NO: 22 and 23) and assembled
under the control of the P14BCD1 constitutive promoter in
plasmid pFD69 amplified with primers F174/F175 (SEQ ID
NO: 24 and 25), giving plasmid pFD72
(pFAB3905ΩP14BCD1luxAcat) (SEQ ID NO: 76).

The LuxA variants were encoded as a DNA sequence,
corresponding genes were synthesized by Twist Bioscience
(Table 4 and 5). The luxA variants were amplified from
synthesized DNA fragments using primers F208/F209 (SEQ
ID NO: 28 and 29) and cloned in plasmid pFD69, under the
control of constitutive promoter and in a bicistronic device,
amplified with primers F206/F207 (SEQ ID NO: 26 and 27)
through Gibson assembly, giving plasmids pFD90-Vx (pFAB3905ΩP14BCD1luxA-Vxcat) where x corresponds to the number of the variant. All plasmids were verified by Sanger sequencing.

The resulting plasmids (pFD72 and pFD90-Vx) were transformed in *E. coli* DH5alpha carrying the plasmid pDB283 expressing the luxCDABE operon from *Photorhabdus luminescens* with gene luxA deleted (pCM17ΩΔluxA; SEQ ID NO: 77) and transformants were selected on LB agar containing kanamycin (50 μg/ml) and chloramphenicol (20 μg/ml).

Bioluminescence Measurements

Strains were grown in triplicate overnight at 37° C. and diluted 1:100 in 1 ml of LB broth in a 96-well microplate that was incubated at 37° C. with shaking in ThermoMixer (Eppendorf). After 5h of growth, luminescence monitoring was performed with 100 μl in white 96-well microplate (Greiner, Kremsmünster) on a Centro XS LB 960 microplate luminometer (Berthold Technologies, Thoiry). The luminescence was measured during 10 s for each well. In parallel, to study the growth of the strains, the overnight cultures were diluted 1:100 in 200 μl of LB broth in a 96-well microplate that was incubated at 37° C. with shaking in a Infinite M200 PRO reader (TECAN). Absorbance was measured at 600 nm every 10 min. None of the strains showed a growth defect.

FIG. 23 illustrates the bioluminescence of LuxA variants relative to the wild-type LuxA protein as a function of the number of amino-acid substitutions. Points at the bottom of the graph are below the limit of detection.

Luminescence could be measured for 18/23 (78%) of the LuxA variants (FIG. 23), with the most distant variants still producing light carrying 27 mutations.

The probability that a random mutation in a protein sequence leads to its inactivation has been estimated to be ~34% (Guo et al., 2004 "*Protein tolerance to random amino acid change*" PNAS Jun. 22, 2004 101 (25) 9205-9210;). Accordingly, one can make the crude estimate that 27 random mutations would only lead to a functional protein in 1 case out of 100,000. The ability of the conditional variational auto-encoder (CVAE) having an autoregressive decoder to generate functional distant variant thus demonstrates its ability to learn and decode meaningful representations of proteins.

Comparison of Different Autoregressive Neural Network Architectures

The choice of the details of the decoder architecture has an important role to play in determining whether the model mainly learns to use the latent space or mainly learns to use the conditional distribution in predicting amino acids, and, by extension, has an important effect on the way in which the model generates new proteins. The conditional variational auto-encoder (CVAE) architecture having an autoregressive decoder as illustrated in FIGS. 2*a* to 5*b*, is chosen to balance the information in the latent space and in the conditional distribution. This choice is made possible by the inclusion of both an autoregressive and a feed-forward component in the decoder, and offers greater flexibility and control over the generation process than would be possible with a differently designed model. A model without latent variables which relied entirely on the conditional distribution would not offer control over the generation. A model which uses latent variables, but does not attempt to learn the conditional distribution, may struggle to generate coherent proteins.

Specifications of the Architecture According to Embodiments

Encoder

The encoder takes as input a fixed length, one-hot encoded protein sequence (padding characters are added to the end of sequences so that they are all of length 504) and outputs the parameters of the standard Normal distribution from which the latent code representing the protein is drawn. These parameters are the mean vector, and a vector of variances, each having the same number of dimensions as the latent code. To generate these parameter vectors, the one-hot encoded input is processed by a series of five 1D convolutional layers. The first layer has 21 filters and a stride size of 1. The subsequent layers all have a stride size of 2 meaning that the resolution of the representation is decreased by a factor of 2 by each of these layers. The number of filters is increased by a factor of 2 each time the resolution is decreased by a factor of 2. All convolutional layers have a kernel size of 2, PReLu activation functions and are batch normalized. Finally the output of the convolutional layers is fed separately through two output layers: a single fully connected layer with linear activation to produce the mean vector, and a fully connected layer with softplus activation to produce the variances.

Decoder

The decoder operates sequentially, with its outputs at each time step corresponding to probabilistic predictions of the identity of the amino acid at the next position in the sequence, given the latent code and the identities of the previous amino acids in the sequence. The decoder can be separated into two components: an up-sampling component and an autoregressive component. The autoregressive component acts sequentially on the output of the up-sampling component together with the input protein sequence to produce predictions for the next amino acid at each point in the sequence.

Up-Sampling Component

The up-sampler takes as input the latent vector and outputs a sequence of the same length as that of the padded proteins. It achieves this by inverting the sequence of operations in the encoder: the latent code is fed first through a fully connected layer, then through a series of deconvolutional layers, in each of which the resolution increases by a factor of 2 while the size of the feature vectors at each position is halved, until the representation is a sequence of the same length as the input proteins, with a 42-dimensional feature vector at each point in the sequence.

Autoregressive Component

The autoregressive component acts sequentially on the sequence of latent feature vectors output by the up-sampler together with the one-hot encoded input protein sequence. At time step t the autoregressive component takes as input the values of the two sequences up to position t and predicts the amino acid at position t+1.

The autoregressive processing is achieved by a series of dilated causal convolutions organized in the same manner as in a Wavenet. In detail, the one hot encoded protein sequence is first processed by a single causal convolution layer. Then the activations of this layer together with the latent feature sequence are passed through two residual blocks. In each residual block one or more dilated convolutions are applied to the activations from the previous layer or block. The resulting sequence of activations is then added to a linearly transformed version of the sequence of latent feature vectors, before being passed through a gated activation function as in Wavenet. Finally the output of the residual blocks is passed through a linear output layer with softmax activations to generate a prediction at each time step. The processing is such that the prediction at each timestep is a function only of the c preceding values of the input sequences, where c is a fixed context length which is controlled by the number of dilated convolutional layers. We use $c=64$.

PReLu activations and batch normalisation are used for the deconvolution and dilated convolution layers throughout the decoder.

Ablation Experiments

The design choices relating to the structure of the decoder outlined above play an important role in determining the ability of the model to generate interesting novel proteins. In order to highlight the effect of these choices, proteins generated by the model outlined above (referred as "Up-sampling+AR") can be compared to those generated by models which instantiate different design choices. Of particular relevance are comparisons to models in which the roles of the latent variables or that of the conditional distribution of amino acids are either suppressed or removed entirely. This section reports the results of experiments on such models, in particular:

(i) a "non autoregressive (non AR)" model in which the output of the up-sampler is used directly to predict the amino acid identities, with no information about prior amino acids, (ii) a "no up-sampling" model in which the up-sampling component is removed, and (iii) a "reduced z" model in which the information provided by the latent variables is heavily suppressed by setting the latent variable dimension to 2 and removing the up-sampling component, so that the model must rely almost entirely on conditional information in predicting amino acids (and, by extension, in generating new proteins).

Various forms of assessment were used to benchmark the behavior of generative models, each deriving from one of the following requirements on the performance of a good model: (i) a good model should be able to successfully (approximately) reconstruct known proteins having first projected them down to a lower dimensional representation, (ii) a good model should allow to generate novel proteins which share common properties or functions with other proteins from the same family but at the same time are not trivially similar to known proteins.

For comparison, the above generative models were trained with the same dataset used for the generation of LuxA variants.

Comparison of Prediction Accuracy of Amino Acid Identities

A model's reconstruction ability can be measured by the accuracy of its predictions of amino acid identities. That is, for each position (in a protein p), how accurately does the model predict the identity of the amino acid at that position in p given the latent vector z representing p and the c previous amino acids in p. This accuracy can be computed over the predictions in every position in a set of proteins (which may be a different set from those used for training), and refer to this quantity as the "amino acid reconstruction accuracy" on that set. This accuracy can be computed in two ways, corresponding to the training and generation modes: in the first, the context provided to the autoregressive component is the c previous amino acids in the protein being reconstructed, in the second the context provided the autoregressive component is the c previous predictions. We refer to these two modes as "true context" and "predicted context". When using the predicted context rather than the true context, the model's accuracy will be much lower if insertions cause the straightforward alignment between positions in p and the reconstruction to be broken. To account for this possibility, a third score is also reported, the percentage identity of the reconstruction and p, after realigning the reconstruction to p.

FIG. 24 illustrates the protein reconstruction accuracies for the neural network architectures "Non AR", "No up-sampling", "Reduced z" and "Up-sampling +AR".

These three quantities show significant differences in behavior of the differently designed models. The highest accuracy of any model trained with the "true context" is achieved by the model with both up-sampling and autoregression, due to its ability to exploit both contextual information and the global latent code. This accuracy comes at the price of reduced accuracy when reconstructing with only "predicted context", due to the reliance on the context for important information allowing errors to accumulate. The reduction in accuracy is however mitigated by the use of up-sampling, with the "no up-sampling" model showing a much greater drop in accuracy when using the predicted context.

Comparison of the Properties of the Generated Sequences

A more direct assessment of the generative abilities of the models can be made by comparing the properties of the sequences that they generate. Sequences can be generated from a VAE in an unconstrained manner by sampling from the prior distribution over the latent variables. Given a latent vector sampled from the prior, a full sequence can be generated by simply passing the latent vector to the decoder (in "predicted context" mode). A KL term (Kullback-Leibler divergence) can be used as a measure of the distance between the prior distribution and the distribution of the projection of samples into the latent space The KL term in the optimization objective forces the encoder to map proteins from the training data distribution in such a way that the distribution of the latent vectors assigned to training data points should be close to the prior. It is this constraint which (if sufficiently closely obeyed) means that latent vectors drawn from the prior should be decoded to proteins with properties close to those of the training set. This is clearly desirable behavior for a generative model, since it provides an easy way of generating novel proteins which nonetheless correspond in important ways to the known proteins from a given family, and in particular, which might be expected to show significant structural or functional similarity.

A qualitative picture of whether the proteins generated by the model are similar to those of the training dataset can be obtained by visualising the predicted secondary structures of the generated sequences.

FIG. 25 illustrates the aligned secondary structures of sequences selected at random from training set and FIG. 26 the aligned secondary structures of sequences generated by sampling from prior of the "Non AR", "No up-sampling", "Reduced z" and "Up-sampling+AR" models.

Proteins from the bacterial-luciferase like family display a consistent pattern of repeating alpha helices and beta strands in their predicted secondary structures. This is in agreement with knowledge of the secondary structures of solved proteins such as LuxA and LuxB from *Vibrio Harveyi*, which both display this pattern and fold into a TIM-barrel. A simple visualisation of the predicted secondary structures of a random sample of 3000 proteins from the training dataset makes this pattern clear (FIG. 25). A visual assessment of the quality of the samples of protein-generating models can therefore be made by visualising the predicted secondary structures of the samples in the same way and looking for evidence of the same patterns that are present in the training set (FIG. 26). Only the models with an autoregressive component are able to consistently generate proteins with the desired pattern of alternating alpha helices and beta strands.

Quantitative assessment of generation quality can be performed using the PFAM family HMM (Hidden Markov models). The HMM is a model designed to compute the probability that a sequence is a member of a given family. This is reported as an E-value, which measures the probability of a sequence achieving the same score as the sequence in question by chance.

FIG. 27 illustrates the percentage of HMM hits for samples from the "Non AR", "No up-sampling", "Reduced z" and "Up-sampling+AR" models.

The results of scoring the 3000 samples from the models visualised above confirm the observation that the autoregressive models are much more successful at generating sequences resembling those of the target family than the model which uses only an up-sampler in the decoder (FIG. 27).

Comparison to RNN Decoder

In principle the autoregressive component of the decoder can be instantiated by any autoregressive network. However the use of an autoregressive convolutional neural network (autoregressive CNN) offers an important degree of flexibility in controlling the size of the context available at each time step. By limiting this context to a size less than that of the full protein the autoregressive component is encouraged to focus on local conditional details of the sequence while the latent code is responsible for global structural details. This encourages a balancing of contributions between the two components, which ensures both information in the conditional distribution and information in the latent code are exploited. Experiments where the autoregressive component was instead instantiated with a recurrent neural network indicated that in this case this balance would be harder to control.

FIG. 28 illustrates the evolution of KL loss term during training for the "Upsampling+AR (KL annealed)", "RNN (KL annealed)" and "RNN" models.

When trained with an RNN in the decoder, the model showed a tendency to fail to place any information in the latent code, instead relying entirely on the contextual information to make amino acid predictions. This behavior can be observed by looking at the KL term in the objective function. This term measures the distance between the distribution over latent variables predicted for proteins in the training set by the encoder and the prior, a standard normal distribution. Models with an RNN in the decoder often minimize this distance early in training, by simply encouraging the encoder to output normally distributed latent codes, and focus later in training only on minimizing the reconstruction loss term (FIG. 28). This behavior results in no information being stored in the latent code, as can be seen by the fact that in this case, samples taken from the model by first sampling a latent code from the prior distribution and then passing the code to the decoder show little or no diversity, irrespective of the sampled code. Ways of mitigating this kind of problem are discussed in Bowman et al. "*Generating Sentences from a Continuous Space.*" CoRR, 2015., and experiments suggest that both gradually increasing the weight of the KL term from a small value (typically 0-0.2) to 1, and applying a dropout mask to some percentage of the positions in the "true context" input can lead models with either an RNN or CNN autoregressive component to put more information in the latent code that they otherwise would. FIG. 28 compares the behavior of the "Up-sampling+AR" model with CNN vs RNN autoregressive component with the KL term either constant at 1, or increased gradually from 0.2 to 1 ("KL annealed"). In both cases the model with a CNN autoregressive component relies more heavily on the latent code. The RNN without KL annealing does not use the latent code at all.

Conclusion

Experiments with the details of the VAE architecture reveal the extent to which the behavior of the trained model depends on the design choices made. The use of a hybrid decoder incorporating both up-sampling and autoregression is motivated by the observation that pure up-sampler/feed-forward decoders, though able to achieve good reconstruction accuracies on held out proteins, make for bad generative models, with samples drawn from these models only rarely matching the HMM profile of the family, and failing to display the secondary structure characteristic of luciferase-like proteins. At the same time, pure autoregressive models show significant drops in reconstruction accuracy when generating with only the predicted rather than true context as signal for the autoregressive predictions. This diminishes the amount of information that can be specified about the nature of the protein to be generated via the latent variables, leading to a reduction in the control over the generative process that the model affords.

Thus, an architecture with a hybrid decoder incorporating both up-sampling and autoregression, for example the conditional variational auto-encoder (CVAE) having an autoregressive decoder as illustrated in FIGS. 2a to 5b, is the architecture that achieves high performances on metrics designed to test both the ability to control the generative process through the specification of latent variables and the ability to sample novel proteins by sampling from the prior over the latent variables as desirable.

FIG. 19 illustrates the projection of five Interpro families in the latent space. The z-axis is a vector that is obtained by maximizing its projection on five normal vectors of the hyperplanes defined by the logistic regression.

FIG. 20 schematically illustrates a processing device 2000 configured to implement at least one embodiment of at least part of the invention, for example one or several of the algorithms described by reference to FIGS. 3 to 9. The processing device 2000 may be a device such as a micro-computer, a workstation, or a highly parallel computer. The device 2000 comprises a communication bus 2013 to which there are preferably connected:

a central processing unit 2011, such as a microprocessor, denoted CPU;

a read only memory 2007, denoted ROM, for storing computer programs for implementing the invention;

a random access memory 2012, denoted RAM, for storing the executable code of the method of embodiments of the invention as well as the registers adapted to record variables and parameters necessary for implementing the method for improving the assembling of raw images obtained by single molecule localization microscopy according to embodiments of the invention; and a communication interface 2002 connected to a communication network 2003 over which digital data to be processed can be transmitted.

Optionally, the apparatus 2000 may also include the following components:

a data storage means 2004 such as a hard disk, for storing computer programs for implementing methods of one or more embodiments of the invention and data used or produced during the implementation of one or more embodiments of the invention;

a disk drive 2005 for a disk 2006, the disk drive being adapted to read data from the disk 2006 or to write data onto said disk;

a screen 2009 for displaying data and/or serving as a graphical interface with the user, by means of a keyboard 2010 or any other pointing means; and graphic processing units (GPU), not represented, that allow parallel processing of large matrix data and that may be used, in particular, for carrying out operations of the artificial neural network(s). GPU may prove to be important for optimizing computation time.

The communication bus provides communication and interoperability between the various elements included in the apparatus 2000 or connected to it. The representation of the bus is not limiting and in particular the central processing unit is operable to communicate instructions to any element of the apparatus 2000 directly or by means of another element of the apparatus 2000.

The disk 2006 can be replaced by any information medium such as for example a compact disk (CD-ROM), rewritable or not, a ZIP disk or a memory card and, in general terms, by an information storage means that can be read by a microcomputer or by a microprocessor, integrated or not into the apparatus, possibly removable and adapted to store one or more programs whose execution enables the method for improving the assembling of raw images obtained by single molecule localization microscopy according to embodiments of the invention to be implemented.

The executable code may be stored either in read only memory 2007, on the hard disk 2004 or on a removable digital medium such as for example a disk 2006 as described previously. According to a variant, the executable code of the programs can be received by means of the communication network 2003, via the interface 2002, in order to be stored in one of the storage means of the apparatus 2000 before being executed, such as the hard disk 2004.

The central processing unit 2011 is adapted to control and direct the execution of the instructions or portions of software code of the program or programs according to the invention, instructions that are stored in one of the aforementioned storage means. On powering up, the program or programs that are stored in a non-volatile memory, for example on the hard disk 2004 or in the read only memory 2007, are transferred into the random access memory 2012, which then contains the executable code of the program or programs, as well as registers for storing the variables and parameters necessary for implementing the invention.

In this embodiment, the apparatus is a programmable apparatus which uses software to implement the invention. However, alternatively, the present invention may be implemented in hardware (for example, in the form of an Application Specific Integrated Circuit or ASIC).

It is to be noted that while embodiments have been described by reference to variational auto-encoders, other generative deep neural models may be used. In particular, embodiments may use adversarial auto-encoders (AAE) or conditional adversarial auto-encoders (CAAE) that add a discriminator network to an auto-encoder. The discriminator is trained to differentiate randomly sampled points in the latent space from the projection of actual data. The encoder is trained to fool this discriminator, thus forcing projections to occupy the whole latent space and ensuring that all points of the latent space can be decoded into valid samples. The concept and training procedure for this type of architecture are detailed in "Adversarial Autoencoders", Alireza Makhzani, Jonathon Shlens & Navdeep Jaitly, Ian Goodfellow, Brendan Frey, arXiv:1511.05644v2 (see e.g. § 2).

FIG. 21 illustrates an example of the logical architecture of a conditional adversarial auto-encoder having an autoregressive decoder.

As illustrated, conditional adversarial auto-encoder 2100 comprises an encoder 2105 and an autoregressive decoder 2110. The input vector 2115, denoted x, as well as additional information 2120 or conditions, denoted c, are applied to encoder 2105 to generate latent vector 2125, denoted z. An example of encoder 2105 is illustrated in FIG. 22a.

Again, for the sake of illustration, additional information 2120 may comprise the length of the protein, its charge, its isoelectric point, its molar extinction coefficient, its solubility (e.g. probability of expression in E.coli inclusion bodies: the smaller this quantity, the more soluble the protein is), and/or its molecular weight, it being observed that some of these values may be correlated (for example, the molecular weight of a protein is highly correlated with its length).

According to the illustrated example, latent vector 2125 and additional information 2120 are then applied to up-sampler 2130 to generate up-sampled latent vector 2135, denoted z'. Latent representation z is up-sampled in up-sampler 2130 while being conditioned by additional information c to generate latent representation z'. The obtained up-sampled latent vector 2135, i.e. latent representation z', and input vector x are then input in autoregressive module 2140 to generated result 2145, denoted x'.

Again, it is to be noted that the use of an up-sampling module is not requested in all embodiments. For example, the size of the latent code z may be increased by concatenation to reach the one of input vector x.

It is also to be noted that according to particular embodiments, no additional information is fed into encoder 2105 and up-sampler 2130.

Autoregressive decoder 2110 may be similar to autoregressive decoder 210 described by reference to FIG. 2a.

Encoder 2105 and decoder 2140 can be similar to those described previously, with the difference that in the case of an adversarial auto-encoder architecture, the encoder is not probabilistic and simply makes a projection of vector x onto latent space z as illustrated in FIG. 22a.

Conditional adversarial auto-encoder 2100 further comprises a discriminator 2150 for discriminating projected samples (i.e. samples projected from input vectors) from drawn samples (i.e. samples obtained from the distribution within the latent space (p(z)). An example of discriminator is illustrated in FIG. 22b.

FIG. 22a illustrates an example of the functional architecture of encoder 2105 illustrated in FIG. 21. It is to be noted that other functional architectures may be implemented.

As illustrated, input vector x is fed in five successive 1D convolution layers referenced 2200-1 to 2200-5 (for the sake of clarity only two of them are represented). According to embodiments, the stride of these convolution layers is set to two, except for the first one which is set to one. The output of 1D convolution layer 2200-5 is flattened (reference 2205) so as to suppress one dimension. The convolution layers aim at establishing relations between parts of protein sequences.

In parallel, additional information or conditions c are fed into two successive dense layers 2210-1 and 2210-2, i.e. into two fully connected neural networks that aim at identifying what should be in protein sequences.

The output of flattened layer 2205 and the output of dense layer 2210-2 are then concatenated (reference 2215). As illustrated, the result of the concatenation is fed into two successive dense layers 2220-1 and 2220-2, the result of the latter being latent vector z FIG. 22b illustrates an example of the functional architecture of discriminator 2150 illustrated in FIG. 21. It is to be noted that other functional architectures may be implemented.

As illustrated, discriminator 2150 is based on two dense layers 2250-1 and 2250-2 that are fully connected neural networks aiming at identifying what should be in protein sequences.

Training such a conditional adversarial auto-encoder and generating protein sequences with such a conditional adversarial auto-encoder may be based on the steps described by reference to FIG. 6.

Other generative deep neural models may use generative adversarial networks (GANs) that are trained to generate realistic data samples from noise using a generator network trained to fool a discriminator network. The discriminator is itself trained to distinguish generated samples from real samples. The architecture and training procedures for this type of networks are described in "*Generative Adversarial Networks*", Goodfellow I J, Pouget-Abadie J, Mirza M, Xu B, Warde-Farley D, Ozair S et al., arXiv:1406.2661v1, and "*NIPS* 2016 *Tutorial: Generative Adversarial Networks*", Goodfellow I arXiv:1701.00160v4. While GANs work very well with continuous data, it currently remains a challenge to train them on discrete data. Indeed, generating discrete data involves a discontinuous step making it impossible to train via backpropagation. A recent study proposed a strategy to train GANs on discrete data, and is another interesting avenue to generate proteins (see "*Boundary-Seeking Generative Adversarial Networks*", Devon Hjelm R, Jacob A P, Che T, Cho K, Bengio Y., arXiv:1702.08431v2)

Other generative models can be constructed in which the encoder and decoder architectures can be modified to include attention mechanisms as described for instance in "*Convolutional Sequence to Sequence Learning*", Jonas Gehring, Michael Auli, David Grangier, Denis Yarats, Yann N. Dauphin, arXiv:1705.03122v3, or in "*Attention Is All You Need*", Ashish Vaswani, Noam Shazeer, Niki Parmar, Jakob Uszkoreit, Llion Jones, Aidan N. Gomez, Lukasz Kaiser, Illia Polosukhin, arXiv:1706.03762v4.

Another possible improvement is to make the autoregressive module bi-directional. Two networks would be trained in parallel to predict the next amino-acid in a sequence, one from left to right and the other from right to left. The generation process would then happen in two steps. In a first step a protein sequence can be generated from left to right (or vice-versa), and in a second step the generated sequence can be modified according to the predictions made by the second model reading the sequence in the opposite direction.

Naturally, in order to satisfy local and specific requirements, a person skilled in the art may apply to the solution described above many modifications and alterations all of which, however, are included within the scope of protection of the invention as defined by the following claims.

APPENDIX

---

Algorithm 1: generation of a protein sequence from a latent code and conditions

---

Input: three arrays
    1. latent code z,
    2. conditions c,
    3. protein sequence x to be generated, it is padded with zeroes at initialization and is updated
       step by step to become a one-hot-encoded protein
Output: a one-hot-encoded protein
/* predict amino acids one after the other */
for i = 1 ... prot_size do
    pred ← Decoder([x,z,c]);
    pred ← pred[i,:]; // the model is autoregressive: only the i-th position is considered
    pred ← argmax pred;
        AA
    x[i,pred] ← 1;
end
return x

---

Algorithm 2: example of steps for computing a BLOSUM-like matrix

---

Input: three arrays
    $n_{samples}$: the number of proteins to sample to estimate the BLOSUM scores
    $n_{char}$: the number of amino acids (plus the padding characters)
    length: the length of proteins
Output: a BLOSUM-like matrix
BLOSUM ← $0n_{char},n_{char}$
count ← $0n_{char},n_{char}$ // normalizing factors
for i = 1 ... $n_{samples}$ do
    z ← sample(N(0,1));
    c ← sample(N(0,1));
    x ← $0lenght,n_{char}$;
    pred ← Decoder([x,z,c]);
    pred ← pred[i,:]; // the model is autoregressive: only the i-th position is considered
    most_likely ← argmax pred;
        AA
    x[i, most_likely] ← 1;
    BLOSUM[most_likely,:] ← BLOSUM[most_likely,:] + pred;
    BLOSUM[:,most_likely] ← BLOSUM[:,most_likely] + pred;

-continued

---

Algorithm 2: example of steps for computing a BLOSUM-like matrix

---

Count[most_likely,:] ← Count[most_likely,:] + 1;
    Count[:,most_likely] ← Count[:,most_likely] + 1;
End
result ← log(BLOSUM/count);
diagonal (result) ← mean(result);
return result

---

TABLE 1

--- alignment between an input protein and a reconstruction

---

```
init      MKIGVFIPIGNNGWLISSNAPQYMPSFELNKAIVQQAEHYQFDFALSMIKLRGFGGKTEF  60
recons    MKIGVFIPIGNNGWLISTNAPQYMPSFELNKAIVQKAEHYQFDFALSMIKLRGFGGKTEF  60
          ***************.***********:************************ init      WDHNLESFTLMAGLAAVTSRIKIYATAATLTLPPAIVARMASTTDSISNGPFGLNVVTGW  120
recons    WDHNLESFTLMAGLAAVTSRIKIYATAATLTLPPAIVARMASTTDSISNGPFGLNVVTGW  120
          *********************************************************** init      QKPEYEQMGLWPGDEYFSRRYDYLSEYVEVLQQFWGTGQSDFNGEFFQMDDCRVSPQPQT  180
recons    QKPEYEQMGLWPGDEYFSRRYDYLSEYVQVLRDLWGTGKSDFKGEFFQMDDCRVSPQPQA  180
          ***************************:**:*:****:***:***************:

init      PIKLICAAQSDAGMAFSAKYADYNFCFGKGVNTPTAFAPTAARLQKAAEQAGREVSSYVL  240
recons    PIKVICAGQSDAGMAFSAKYADYNFCFGKGVNTPTAFAPTAARMKEAAEKAGRDVSSYVL  240
          *:*.*********************************:.::*:*.**** init      FMIIADETDELARAKWESYKAGADTEALAWLTEQSGKDTQSGADTNVRQMADPTSAVNIN  300
recons    FMIIADETDEAARAKWESYKAGADTEALAWLTEQSGKDTKSGADTNVRQMADPTSAVNIN  300
          ******** ***********************:*************** init      MGTLVGSYANVAKMMDDIATVPGTEGILLTFDDFLSGIENFGQHIQPLMNSRADTVDTLP  360
recons    MGTLVGSYANVARMMDETATVPGTEGILLTFDDFLSGIENFGQRIQPLMKSRADIIPTPP  360
          **********:*:***********************:*:***: * * init      PAAREVA  367
recons    EAAREVA  367
             ******
```

---

TABLE 2

--- alignment between a generated protein randomly sampled
from the latent space and the most similar known sequence

---

```
generated     MPVSWLLLGHSSGVGLGGPDAAAAAEGAYGFRAAVVAERVGFDGVLLGARGSPEYP----  56
most_similar  ------MDTRTSGITIGYKASAEQFGPRHLVELAVLAERRGFDSVLVSDHYQPWRHRNGH  54
                  :  ::**: :*   .:*      :  .. :* *.;. : .* generated     --ATVARLL-AEAALHQLRLGAG-VTATSTYAPAAGVEVLGTLASLFPRDIILGLGISTG  112
most_similar  APFSMAWLAAAGERTERVRLGTSVLTATERYHPAVVAQAFGTLGALCPGRVMLGLGTGEA  114
                :* * *   . .:***:. :*** * **. .:.:***.:* *  :*****  . .

generated     ARHDEAGGRDRFQRWEGDFGDHYPAVRGALGLWTDEEVLREASFASPYYPRGVEG-W---  168
most_similar  LNE-VAVARMEWPGFEERFARLREAIDLIRPLWTEERVS----FDGEYYRTENATVYDPP  169
              .. * .* .: :* *. *: ***:*.* * . ** :

generated     ----RVVVSPRPPRAGLWLGEKPEDVG-VLGDDVALL-HAFRPVFGRSGPAVAGLLGADV  222
most_similar  SRPVPVYVAAGGPVVAKYAGRIADGFICTSGKGMELYTEKLQPAVDA------G----AE  219
                  * *:   *  ..: *.  :..  . *..: *  . .:*...      * generated     PAWAPAGLMPTVDVRLIWGGSPS----DAQFLADLERAEALAFARAEGMRGVEAEPTRRL  278
most_similar  AGREPADVARTIEIKLSYDTDAEAAAENTRFWAPLS-----------------------L  256
                . **.:  :::*  :. .   ::* * *.                          * generated     LAEATSGAPDEAAAGTLAAQQVDVEIDGTPWWAET-PRT--------VSAGLGAAEL---  326
most_similar  TADQKRGVSDPLAME-RAADELPMSQIASRWIVSSDPDEVVERIRPYVDAGFTDLVLHAP  315
                *: . *. * *   **::: :.  .: * ..: *          *.**:    * generated     ---GTRLVAVGLDAVATGATSVDGWSTVGGLAGGGDGFWIGPELYADGARRGAAFDGDVA  383
most_similar  GHDQAPFLELARQDL------LPRLSNLGG----------------------------- 339
                 :*:: :. : :        :    .:**
```

TABLE 2-continued alignment between a generated protein randomly sampled
from the latent space and the most similar known sequence

```
generated    SLSPGRVADH 393
most_similar ----------
```

TABLE 4-continued protein sequences of the LuxA variants

| Protein sequence | Nb of mismatches | SEQ ID NO: |
|---|---|---|
| LuxAM1V7 Variant | 13 | 37 |
| LuxAM1V8 Variant | 16 | 38 |
| LuxAM1V9 Variant | 15 | 39 |
| LuxAM1V10 Variant | 27 | 40 |
| LuxAM1V11 Variant | 16 | 41 |
| LuxAM1V12 Variant | 20 | 42 |
| LuxAM1V13 Variant | 10 | 43 |
| LuxAM1V14 Variant | 27 | 44 |
| LuxAM1V15 Variant | 20 | 45 |
| LuxAM1V16 Variant | 25 | 46 |
| LuxAM1V17 Variant | 25 | 47 |
| LuxAM1V18 Variant | 15 | 48 |
| LuxAM1V19 Variant | 23 | 49 |
| LuxAM1V20 Variant | 34 | 50 |
| LuxAM1V21 Variant | 18 | 51 |
| LuxAM1V22 Variant | 11 | 52 |

TABLE 3 sequences of the primers used for
plasmid construction

| Name | Sequence 5'-3' | SEQ ID NO: |
|---|---|---|
| B731 | TAATATAATAGCGAACGTTGAGTACTAAAGTTTCCAAA TTTCATAGAGAGTCC | 14 |
| B732 | CTATGAAATTTGGAAACTTTAGTACTCAACGTTCGCTA TTATATTAGCTAAGG | 15 |
| LC545 | TCATTTCGAACCCCAGAGTC | 16 |
| LC327 | CGCCTTCTTGACGAGTTCTT | 17 |
| F168 | TCTATCAACAGGAGTCCAAGCGAGCTCGATATCAAATTAC | 18 |
| F169 | TTTTGAATTCGACGTCGACGTCGATATCTGGCGAAAATGAG | 19 |
| F170 | ATCGAGCTCGCTTGGACTCCTGTTGATAGATCCAGTAATG | 20 |
| F171 | CCAGATATCGACGTCGACGTCGAATTCAAAAGATCTTAAG | 21 |
| F172 | CACAGGAGACTTTCTAATGAAATTTGGAAACTTTTTGCT TAC | 22 |
| F173 | CTCGACAACCGATCCCTAATATAATAGCGAACGTTGTTT | 23 |
| F174 | GTTTCCAAATTTCATTAGAAAGTCTCCTGTGCATGATTAAG | 24 |
| F175 | TCGCTATTATATTAGGGATCGGTTGTCGAGTAAGGATC | 25 |
| F206 | CATTAGAAAGTCTCCTGTGCATGATTAAG | 26 |
| F207 | GGATCGGTTGTCGAGTAAGGATC | 27 |
| F208 | CAATTTTCGTACTGAAACATCTTAATCATGCAC | 28 |
| F209 | CGTTTTATTTGATGCCTGGAGATCC | 29 |

TABLE 4

DNA sequences of luxA variants with homologies for
assembly in plasmid pFD72

| DNA sequence | Nb of mismatches | SEQ ID NO: |
|---|---|---|
| luxAM1V0 Reconstruction | 13 | 53 |
| luxAM1V1 Variant | 23 | 54 |
| luxAM1V2 Variant | 16 | 55 |
| luxAM1V3 Variant | 19 | 56 |
| luxAM1V4 Variant | 27 | 57 |
| luxAM1V5 Variant | 14 | 58 |
| luxAM1V6 Variant | 18 | 59 |
| luxAM1V7 Variant | 13 | 60 |
| luxAM1V8 Variant | 16 | 61 |
| luxAM1V9 Variant | 15 | 62 |
| luxAM1V10 Variant | 27 | 63 |
| luxAM1V11 Variant | 16 | 64 |
| luxAM1V12 Variant | 20 | 65 |
| luxAM1V13 Variant | 10 | 66 |
| luxAM1V14 Variant | 27 | 67 |
| luxAM1V15 Variant | 20 | 68 |
| luxAM1V16 Variant | 25 | 69 |
| luxAM1V17 Variant | 25 | 70 |
| luxAM1V18 Variant | 15 | 71 |
| luxAM1V19 Variant | 23 | 72 |
| luxAM1V20 Variant | 34 | 73 |
| luxAM1V21 Variant | 18 | 74 |
| luxAM1V22 Variant | 11 | 75 |
| pFD72 | na | 76 |

TABLE 4 protein sequences of the LuxA variants

| Protein sequence | Nb of mismatches | SEQ ID NO: |
|---|---|---|
| LuxAM1V0 Reconstruction | 13 | 30 |
| LuxAM1V1 Variant | 23 | 31 |
| LuxAM1V2 Variant | 16 | 32 |
| LuxAM1V3 Variant | 19 | 33 |
| LuxAM1V4 Variant | 27 | 34 |
| LuxAM1V5 Variant | 14 | 35 |
| LuxAM1V6 Variant | 18 | 36 |

The invention claimed is:

1. A computer method for generating representations of protein sequences having at least one specific physical or functional property, in an autoregressive neural network comprising an encoder and a decoder, the decoder comprising an autoregressive module, the method comprising:

obtaining a latent code and inputting the latent code into the autoregressive module, the latent code being an encoded representation of a protein sequence and representing essential features of the protein sequence;

obtaining additional information representative of at least one expected specific physical or functional property of the protein sequence, the at least one expected specific physical or functional property comprising at least one among solubility or insolubility, length, charge, weight, molar extinction coefficient, and isoelectric point, the additional information being input along with the latent code into the autoregressive module;

in response to the inputs, obtaining probabilities from the autoregressive module, the obtained probabilities representing probabilities for amino acids to be selected at given locations of the protein sequence; and generating, from the obtained probabilities, a representation of the protein sequence as an ordered sequence of amino acids, wherein the autoregressive module is such that, for a location of the sequence, the probabilities associated with amino acids to be selected for the location in the sequence are determined as a function of probabilities of amino acids to be selected for previous locations in the sequence, and, wherein the autoregressive neural network has been trained end-to-end with the encoder, the encoder making it possible to encode representations of protein sequences in a latent space as latent codes, additional information representative of specific physical or functional properties of protein sequences used for training the autoregressive neural network being input along with the representations of the protein sequences into the encoder during training, the protein sequence to be generated being a variant of the protein sequences used for training.

2. The method according to claim 1, wherein the decoder further comprises an up-sampling module for increasing a number of dimensions of a latent code, the obtained latent code being input into the up-sampling module and the up-sampled latent code being input into the autoregressive module.

3. The method according to claim 1, wherein the generating an ordered sequence of amino acids comprises selecting sequentially each amino acid of the ordered sequence and, after an amino acid is selected to belong to the ordered sequence, checking the likelihood of usefulness of the ordered sequence at least partially generated.

4. The method according to claim 3, wherein checking the likelihood of usefulness of the ordered sequence at least partially generated comprises comparing the length of the ordered sequence at least partially generated with a threshold.

5. The method according to claim 1, wherein the generating an ordered sequence of amino acids comprises selecting sequentially each amino acid of the ordered sequence and wherein generating an ordered sequence of amino acids is stopped if a specific symbol is selected as an amino acid for a given position of the ordered sequence.

6. The method according to claim 1, wherein the generating an ordered sequence of amino acids comprises selecting one amino acid, for a given position of the ordered sequence, among a plurality of amino acids, the one amino acid being selected as a function of the probabilities associated with amino acids of the plurality of amino acids for the given position.

7. The method according to claim 1, further comprising a learning phase for determining parameters of the autoregressive module.

8. The method according to claim 7, wherein the learning phase is unsupervised.

9. The method according to claim 1, wherein the autoregressive neural network is of the variational auto-encoder type or of the adversarial auto-encoder type.

10. The method according to claim 1, wherein the autoregressive neural network is a recurrent neural network.

11. An apparatus comprising a processor and a non-transitory computer-readable storage medium storing instructions, that are configured to cause the apparatus to perform the method according to claim 1 when executed by the processor.

12. A non-transitory computer program product comprising computer program instructions for a programmable apparatus, the computer program product comprising instructions that are configured to cause the programmable apparatus to carry out each step of the method according to claim 1 when the program is loaded and executed by a programmable apparatus.

13. A method for producing a protein, the method comprising:

performing a computer method for generating protein sequences in an autoregressive neural network comprising an encoder and a decoder, the decoder comprising an autoregressive module, the computer method comprising:

obtaining a latent code and inputting the latent code into the autoregressive module;

obtaining probabilities from the autoregressive module, the obtained probabilities representing probabilities for amino acids to be selected at given locations of a sequence; and generating an ordered sequence of amino acids from the obtained probabilities, wherein the autoregressive module is such that, for a location of the sequence, the probabilities associated with amino acids to be selected for the location in the sequence are determined as a function of probabilities of amino acids to be selected for previous locations in the sequence, and, wherein the autoregressive neural network has been trained end-to-end with the encoder, the encoder making it possible to encode protein sequences in a latent space as latent codes; and synthesizing a protein based on the generated ordered sequence of amino acids.

14. The method according to claim 13, wherein the computer method for generating protein sequences further comprises obtaining additional information representative of at least one characteristic of a protein sequence to be generated, the additional information being input along with the latent code into the autoregressive module, additional information representative of characteristics of protein sequences used for training the autoregressive neural network being input along with protein sequences into the encoder during training.

15. The method according to claim 14, wherein the additional information is directed to physical characteristics of the protein sequences to be generated and of the protein sequences used for training the autoregressive neural network.

16. The method according to claim 13, wherein the decoder further comprises an up-sampling module for increasing a number of dimensions of a latent code, the obtained latent code being input into the up-sampling module and the up-sampled latent code being input into the autoregressive module.

17. The method according to claim 13, wherein the generating an ordered sequence of amino acids comprises selecting sequentially each amino acid of the ordered sequence and, after an amino acid is selected to belong to the ordered sequence, checking the likelihood of usefulness of the ordered sequence at least partially generated.

18. The method according to claim 17, wherein checking the likelihood of usefulness of the ordered sequence at least partially generated comprises comparing the length of the ordered sequence at least partially generated with a threshold.

19. The method according to claim 13, wherein the generating an ordered sequence of amino acids comprises selecting sequentially each amino acid of the ordered sequence and wherein generating an ordered sequence of amino acids is stopped if a specific symbol is selected as an amino acid for a given position of the ordered sequence.

20. The method according to claim 13, wherein the generating an ordered sequence of amino acids comprises selecting one amino acid, for a given position of the ordered sequence, among a plurality of amino acids, the one amino acid being selected as a function of the probabilities associated with amino acids of the plurality of amino acids for the given position.

* * * * *

SEQUENCE LISTING

```
<160> NUMBER OF SEQ ID NOS: 77

<210> SEQ ID NO 1
<211> LENGTH: 337
```

<212> TYPE: PRT
<213> ORGANISM: Kineococcus radiotolerans

<400> SEQUENCE: 1

```
Met Val Asp Thr His Gly Gln Pro Leu Lys Leu Gly Tyr Lys Ala Ser
1               5                   10                  15

Ala Glu Gln Phe Ala Pro Gly Lys Leu Ala Asp Phe Ala Val Gln Ala
                20                  25                  30

Glu Glu Gln Gly Leu Asp Ser Val Trp Ile Ser Asp His Phe Gln Pro
            35                  40                  45

Trp Arg His Val Asp Gly His Ala Pro Ser Ala Leu Val Trp Leu Pro
        50                  55                  60

Trp Val Ala Ala Lys Thr Ser Arg Val Gln Leu Gly Thr Ser Val Leu
65                  70                  75                  80

Thr Pro Thr Leu Arg Tyr Asn Pro Ala Val Ile Ala Gln Ala Phe Ala
                85                  90                  95

Thr Leu Gly Cys Leu Ala Pro Gly Arg Ala Ile Leu Gly Ile Gly Thr
                100                 105                 110

Gly Glu Ala Leu Asn Glu Thr Ala Val Gly Val Thr Phe Pro Glu Thr
            115                 120                 125

Arg Glu Arg Phe Ala Arg Leu Arg Glu Ala Val Arg Leu Ile Lys Gln
            130                 135                 140

Leu Trp Ser Glu Glu Arg Val Thr Phe Glu Gly Glu Tyr Tyr Asn Leu
145                 150                 155                 160

His Asp Ala Thr Val Tyr Asp Arg Pro Glu Gln Pro Val Pro Ile Tyr
                165                 170                 175

Val Ala Ala Gly Gly Pro Gly Val Thr Lys Tyr Ala Gly Arg Ala Gly
                180                 185                 190

Asp Gly Tyr Ile Cys Thr Ser Gly Lys Gly Met Asp Leu Tyr Ser Glu
            195                 200                 205

Thr Leu Leu Pro Ala Leu Arg Glu Gly Leu Glu Ala Ser Gly Arg Thr
            210                 215                 220

Glu Gly Gln Ile Asp Arg Thr Ile Glu Ile Lys Leu Ser Phe Asp Glu
225                 230                 235                 240

Asp Pro Ala Gln Ala Leu Glu Asn Thr Arg Phe Trp Ala Pro Leu Ser
                245                 250                 255

Leu Thr Ala Glu Gln Lys Ser Ser Val His Asp Pro Ile Glu Met Ala
                260                 265                 270

Arg Leu Ala Asp Glu Leu Pro Ile Glu Gln Val Ala Lys Arg Trp Ile
            275                 280                 285

Val Ser Ser Asp Pro Thr Glu Val Ala Ala Ala Val Gln Gly Tyr Val
    290                 295                 300

Asp Ala Gly Phe Thr His Leu Val Phe His Ala Pro Gly Gln Asp Gln
305                 310                 315                 320

Ser Arg Phe Leu Thr Gln Phe Ser Ala Asp Val Val Pro Leu Leu Arg
                325                 330                 335

Pro
```

<210> SEQ ID NO 2
<211> LENGTH: 340
<212> TYPE: PRT
<213> ORGANISM: Artificial Sequence
<220> FEATURE:
<223> OTHER INFORMATION: reconstructed sequence -continued

<400> SEQUENCE: 2

```
Met Ser Asp Thr Phe Gly Ala Ser Leu Ser Glu Tyr Gly Ser Ala Ala
1               5                   10                  15

Gln Phe Ala Pro Ala Ala Pro Gly Asp Leu Trp Asn Ala Val Ala Arg
            20                  25                  30

Ala Ala Glu Ala Gly Gly Phe Asp Met Phe Trp Ala Asp His His His
        35                  40                  45

Pro Asp Gly Gly Gln Leu Pro Ala Gly Glu Gly Leu Met Thr Val Ala
    50                  55                  60

Ala Ala Ala Ala Thr Ala Thr Arg Lys Leu Thr Leu Gly Leu Val Ala
65                  70                  75                  80

Ser Thr Asn Arg Val Arg Gln Val Leu Ala Leu Ala Arg Ala Ala Glu
                85                  90                  95

Val Leu Ser Val Leu Ser Ser Gly Arg Val Leu Leu Gly Leu Gly Thr
            100                 105                 110

Gly Gly His Asp Arg Val Val Ala Ala Tyr Gly Val Pro Tyr Pro Asp
        115                 120                 125

Arg Glu Arg Tyr Arg Arg Leu Arg Glu Ser Leu Arg Ile Phe Arg Glu
    130                 135                 140

Leu Trp Ser Gly Glu Thr Val Ser Phe Glu Gly Glu Tyr Tyr Arg Thr
145                 150                 155                 160

His Asp Val Tyr Gly Tyr Asp Ile Pro Ala Gly Gly Pro Val Pro Ile
                165                 170                 175

Ile Val Ala Gly Gly Ala Pro Ala Glu Arg Tyr Arg Gly Ala Ala Gly
            180                 185                 190

His Asp Phe Leu Cys Val Ser Gly Ser Trp Ala Glu Ala Tyr Arg Glu
        195                 200                 205

Lys Leu Leu Pro Ala Val Asp Ala Gly Ala Asp Ala Ala Gly Arg Asp
    210                 215                 220

Asp Ala Phe Arg Arg Arg Val Ile Glu Leu Lys Ser Tyr Phe Asp Ala
225                 230                 235                 240

Asp Glu Ala Ala Ala Leu Arg Glu Glu Thr Phe Trp Ala Pro Leu Ser
                245                 250                 255

Leu Thr Ala Ala Ala Glu His Asp Val Leu Asp Ala Val Ala Glu Pro
            260                 265                 270

Leu Gly Ala Asp Glu Leu Val Arg Glu Gln Val Ala Lys Arg Trp Ile
        275                 280                 285

Val Gly Ser Ser Pro Asp Asp Ile Ala Ala Leu Ile Asp Pro His Val
    290                 295                 300

Asp Ala Gly Leu Asn Tyr Leu Leu Phe His Ala Pro Gly Gln Asp Gln
305                 310                 315                 320

Asp Arg Phe Leu Asp Leu Phe Gly Glu Leu Val Glu Glu Arg Leu Arg
                325                 330                 335

Ala Val Ala Gly
                340
```

<210> SEQ ID NO 3
<211> LENGTH: 340
<212> TYPE: PRT
<213> ORGANISM: Artificial Sequence
<220> FEATURE:
<223> OTHER INFORMATION: reconstructed sequence

<400> SEQUENCE: 3

```
Met Ser Asp Ala Phe Gly Gly Thr Leu Ser Glu Asn Gly Phe Phe Ala
1               5                   10                  15

Pro Phe Ala Pro Ala Gly Pro Asp Ala Leu Tyr Glu Leu Ala Glu Arg
            20                  25                  30

Ala Gly Leu Ala Glu Asn Gly Phe Gln Asp Trp Trp Phe Pro His Pro
        35                  40                  45

His Leu Asp Gly Thr Pro Thr Trp Pro Glu Ala Asp Tyr Trp Leu Ala
        50                  55                  60

Trp Ala Thr Ala Val Thr Ser Arg Leu Arg Leu Gly Thr Trp Val Leu
65                  70                  75                  80

Ser Asn Thr Phe Arg His Pro Val Val Leu Ala Lys Ser Phe Ala Thr
                85                  90                  95

Ile Asp Gln Leu Ser Asn Gly Arg Val Leu Leu Gly Leu Gly Ser Gly
            100                 105                 110

Gly Val Asp Arg Leu Glu Gly Ala Val Glu Gly Glu Tyr Pro Glu Arg
        115                 120                 125

Val Glu Arg Phe Glu Arg Ser Ala Glu Ser Ile Arg Ile Phe Arg Glu
    130                 135                 140

Met Trp Ser Gly Asp Thr Val Ser Phe Asp Gly Glu Tyr Tyr Thr Thr
145                 150                 155                 160

His Asp Val Tyr Phe Tyr Glu Arg Pro Glu Gln Pro Pro Pro Val Tyr
                165                 170                 175

Ile Ala Ala Gly Gly Pro Gly Val Ala Lys Tyr Asn Gly Arg Ala Gly
            180                 185                 190

Asp Gly Phe Leu Cys Thr Ser Gly Lys Trp Met Asp Ala Asn Arg Glu
        195                 200                 205

Lys Leu Leu Pro Ala Phe Lys Glu Gly Ala Ala Arg Thr Gly Arg Asp
    210                 215                 220

Ala Asp Glu Ile Arg Arg His Ile Glu Ile Asp Leu Ser Tyr Asp Glu
225                 230                 235                 240

Asp Tyr Glu Ala Ala Leu Asp Gly Trp Thr Pro Trp Ala Pro Leu Ser
                245                 250                 255

Leu Thr Ala Glu Gln Pro Val Ala Val Thr Asp Pro Leu Ala Val Pro
            260                 265                 270

Gly Ala Asp Asp Leu Leu Pro Arg Glu Val Ile Ala Ser Arg Trp Ile
        275                 280                 285

Val Gly Ser Ser Pro Asp Glu Val Ala Ala Leu Ile Gln Pro His Val
    290                 295                 300

Asp Ala Gly Leu Asn Tyr Leu Met Phe His Val Pro Gly Gly Asp Gln
305                 310                 315                 320

Asp Arg Phe Leu Glu Leu Phe Glu Gln Ala Val Glu Glu Leu Gly Arg
                325                 330                 335

Thr Gly Phe Gly
            340
```

<210> SEQ ID NO 4
<211> LENGTH: 340
<212> TYPE: PRT
<213> ORGANISM: Artificial Sequence
<220> FEATURE:
<223> OTHER INFORMATION: reconstructed sequence

```
<400> SEQUENCE: 4

Met Ser Asp Thr Ser Arg Gly Ile Leu Gly Tyr Lys Gly Tyr Leu Ala
1               5                   10                  15

Gln Phe Ala Pro Ala Asp Pro Pro Ala Leu Trp Val Ala Ala Val Ala
                20                  25                  30

Glu Glu Ala Gly Arg Arg Thr Phe Met Phe Trp Asp His His Trp Tyr
            35                  40                  45

Pro Ala Gly Gly Thr Pro Gly Phe Thr Glu Gly Trp Met Trp Leu Ala
        50                  55                  60

Ala Ala Ala Ala Arg Thr Ser Arg Ile Arg Leu Gly Thr Leu Val Tyr
65                  70                  75                  80

Ser Thr Pro Phe Arg His Pro Ala Val Val Ala Lys Ser Phe Ala Thr
                85                  90                  95

Val Asp His Ile Ser Gly Gly Arg Val Leu Leu Gly Leu Gly Ala Gly
            100                 105                 110

Ser Gly His Asp Glu Ile Ala Ala Tyr Gly Phe Glu Trp Pro Asp Ala
        115                 120                 125

Gly Glu Arg Tyr Ala Arg Leu Glu Glu Ser Val Arg Ile Ile Lys Glu
    130                 135                 140

Leu Trp Ser Gly Glu Thr Val Ser Phe Asp Gly Glu Tyr Tyr Arg Thr
145                 150                 155                 160

His Asp Ala Leu Val Tyr Pro Arg Pro Ala Gln Gly Pro Pro Val Tyr
                165                 170                 175

Ile Ala Ala Gly Gly Pro Ala Val Ala Lys Arg Ala Gly Arg Val Gly
            180                 185                 190

Asp Gly Phe Ile Cys Thr Ser Leu Gly Gly Asn Asp Leu Leu Arg Glu
        195                 200                 205

Ser Leu Glu Ala Leu Arg Ala Gly Tyr Glu Lys Ala Gly Arg Asp Gly
    210                 215                 220

Asp Phe Val Arg Lys Arg Val Leu Glu Leu Lys Asp Ser Tyr Asp Leu
225                 230                 235                 240

Ala Glu Arg Ala Ala Leu Ala Leu Thr Ala Phe Trp Ala Pro Leu Gly
                245                 250                 255

Leu Thr Pro Ala Gln Lys His Leu Val Leu Asp Pro Ala Pro Met Pro
            260                 265                 270

Glu Arg Ala Asp Glu Leu Val Lys Glu Phe Val Ala Ser Arg Trp Ile
        275                 280                 285

Val Gly Ser Ser Pro Glu Glu Ile Ala Ala Leu Ile Glu Pro His Val
    290                 295                 300

Asp Ala Gly Leu Phe His Leu Val Phe His Ala Pro Gly Gly Asp Gln
305                 310                 315                 320

Asp Arg Phe Leu Asp Leu Phe Gly Arg Asp Val Glu Pro Leu Leu Arg
                325                 330                 335

Ser Pro Ala Ala
            340

<210> SEQ ID NO 5
<211> LENGTH: 338
<212> TYPE: PRT
<213> ORGANISM: Artificial Sequence
<220> FEATURE:
<223> OTHER INFORMATION: reconstructed sequence
```

```
<400> SEQUENCE: 5

Met Ser Asp Thr Gly Thr Ala Thr Leu Ser Glu Gly Gly Thr Ala Glu
1               5                   10                  15

Gln Phe Ser Pro Glu Ala Pro Phe Asp Leu Cys Gly Thr Ala Ala Glu
            20                  25                  30

Ala Gly Phe Leu Ala Asp His Phe Gly Phe Trp Asp His Tyr Trp Ser
            35                  40                  45

Pro Ser Glu Lys Lys Leu Asp Trp Ser Gly Ala Leu Trp Thr Ala Val
        50                  55                  60

Ala Ala Ala Thr Thr Thr Thr Arg Leu Ala Arg Gly Val Leu Val Val
65                  70                  75                  80

Ser Pro Leu Ser Asn His Lys Val Ala Leu Ala Arg Gln Ala Thr Thr
                85                  90                  95

Val Ala Gln Val Ser Gly Asn Arg Val Leu Leu Gly Leu Gly Ser Gly
            100                 105                 110

Gly His Asn Arg Ile Glu Ala Ala Val Glu Gly Asp Tyr Pro Glu Ala
            115                 120                 125

Arg Glu Arg Tyr Ala Gln Leu Arg Glu Ser Ile Arg Ile Ile Arg Glu
            130                 135                 140

Leu Trp Ser Gly Glu Thr Val Ser Phe Glu Gly Glu Tyr Tyr Ser Thr
145                 150                 155                 160

His Asp Val Tyr Arg Tyr Glu Arg Pro Ala Gln Gly Pro Pro Val Tyr
                165                 170                 175

Ile Ala Ala Gly Ser Pro Arg Val Ala Arg Tyr Ala Gly Arg Ala Gly
            180                 185                 190

Asp Asn Phe Leu Cys Thr Ser Gly His Thr Met Asp Ala Tyr Arg Glu
            195                 200                 205

Lys Leu Leu Pro Leu Trp Lys Gly Gly Asp Ala Ala Gly Lys Asp Pro
        210                 215                 220

Asp Asp Leu Arg Ala Arg Val Asp Ile Gln Ile Leu Ser Tyr Thr Asn
225                 230                 235                 240

Asp Glu Glu Ala Ala Ala Glu Leu Thr Arg Gly Trp Ala Pro Leu Gly
            245                 250                 255

Leu Tyr Arg Ala Ala Lys His Asp Val Leu Asp Pro Val Pro Leu Pro
            260                 265                 270

Gln Asp Ala Asp Glu Leu Val Arg Glu Leu Val Ala Ser Arg Trp Val
        275                 280                 285

Val Gly Ser Ser Pro Glu Asp Val Ala Ala Leu Ile Gly Pro Gln Val
        290                 295                 300

Asp Ala Gly Leu Asn Tyr Gly Leu Phe Phe Val Pro Gly Val Asp Gln
305                 310                 315                 320

Ser Phe Asp Leu Ser Leu Gly Leu Ala Leu Asn Ala Glu Leu Leu Arg
                325                 330                 335

Ser Leu

<210> SEQ ID NO 6
<211> LENGTH: 339
<212> TYPE: PRT
<213> ORGANISM: Artificial Sequence
<220> FEATURE:
<223> OTHER INFORMATION: reconstructed sequence
```

-continued

<400> SEQUENCE: 6

```
Met Ser Asp Thr Pro Ser Gly Lys Leu Leu Asp Tyr Gly Thr Gly Ala
1               5                   10                  15

Gln Phe Ala Pro Asp Gly Pro Glu Arg Phe Ala Ser Met Ala Asp Ala
                20                  25                  30

Ala Gly Leu Ala Glu Arg Thr Phe Ser Asp Trp Asp His Phe Gly Tyr
            35                  40                  45

Pro Asp Lys Gly Gly Ala Gly Trp Thr Pro Ala Trp Gly Trp Leu Ala
        50                  55                  60

Ala Leu Ile Ala Arg Thr Ser Arg Ile Lys Leu Gly Thr Ala Val Thr
65                  70                  75                  80

Ser Val Asn Phe Arg His Pro Val Val Ala Ala Lys Ser Ala Ala Thr
                85                  90                  95

Val Asp Ile Ile Ser Gln Gly Arg Ala Asp Leu Gly Leu Gly Ala Gly
                100                 105                 110

Ala Ile Asp Glu Ile Glu Ala Ala Val Glu Gly Ala Trp Pro Pro Ala
            115                 120                 125

Lys Glu Arg Tyr Glu Arg Leu Arg Glu Tyr Leu Glu Ile Ile Arg Glu
        130                 135                 140

Leu Trp Thr Gly Glu Thr Val Ser Phe Glu Gly Lys Tyr Tyr Glu Thr
145                 150                 155                 160

His Gly Ala Gln Phe Tyr Asp Arg Pro Asp Gln Pro Val Pro Pro Tyr
                165                 170                 175

Ile Ala Ala Gly Gly Pro Thr Val Ala Lys Tyr Ala Gly Ala Ala Gly
            180                 185                 190

Asp Gly Phe Leu Cys Val Ser Gly Lys Gly Met Asp Leu Tyr Asp Glu
        195                 200                 205

Lys Leu Leu Pro Gly Phe Lys Glu Gly Ile Asp Ala Leu Gly Arg Asp
    210                 215                 220

Phe Asp Arg Ile Gly Arg Thr Ile Glu Phe Lys Leu Ser Phe Asp Glu
225                 230                 235                 240

Asp Tyr Glu Ala Ala Leu Asp Leu Thr Arg Gly Trp Ala Pro Leu Ser
                245                 250                 255

Leu Thr Ala Glu Gln Asn Phe Asp Val Ala Gly Pro Ile Ala Met Pro
            260                 265                 270

Gln Asp Ala Asp Glu Leu Val Arg Glu Leu Phe Ala Lys Arg Trp Ile
        275                 280                 285

Ala Gly Asn Pro Glu Glu Asn Ala Val Glu Leu Ile Gln Leu Gln Val
        290                 295                 300

Gly Ala Gly Leu Asp Tyr Gly Met Phe His Val Pro Val Gly Asp Gln
305                 310                 315                 320

Asp Arg Phe Glu Glu Leu Phe Asp Arg Phe Ala Glu Gln Leu Arg Arg
                325                 330                 335

Leu Gly Ala
```

<210> SEQ ID NO 7
<211> LENGTH: 337
<212> TYPE: PRT
<213> ORGANISM: Artificial Sequence
<220> FEATURE:
<223> OTHER INFORMATION: reconstructed sequence

<400> SEQUENCE: 7

Met Ser Asp Thr Ala Gly Gly Ala Leu Gly Tyr Pro Gly Ala Leu Ala
1               5                   10                  15

Gln Phe Ser Pro Ala Asp Pro Asp Ala Leu Arg Ile Val Ala Glu Ala
                20                  25                  30

Ala Gly Tyr Ala Glu Asp Ala Phe Gln Asp Trp Thr Phe Pro Trp His
            35                  40                  45

Pro Leu Pro Gly Gln Pro Gly Trp Ser Pro Ala Trp Tyr Ile Leu Gly
        50                  55                  60

Ala Ala Thr Ala Arg Thr Ser Arg Leu Ala Leu Ser Thr Leu Val Thr
65                  70                  75                  80

Ser Val Asn Phe Arg Arg Pro Ala Val Leu Ala Lys Ser Phe Ala Thr
                85                  90                  95

Val Asp His Leu Ser Asn Gly Arg Val Leu Leu Gly Leu Gly Ser Gly
            100                 105                 110

Ser Ala Glu Arg Leu Glu Ala Ala Val Glu Gly Glu Trp Pro Glu Lys
        115                 120                 125

Arg Glu Arg Phe Glu Arg Leu Glu Glu Ser Val Thr Leu Ile Arg Glu
        130                 135                 140

Leu Trp Ser Gly Glu Thr Val Ser Phe Asp Gly Glu His Tyr Thr Thr
145                 150                 155                 160

His Asp Ala Tyr Gly Tyr Pro Met Pro Ala Gln Gly Pro Val Pro Val
                165                 170                 175

Leu Val Thr Gly Gly Ala Pro Val Ala Lys Val Ala Gly Arg Ala Gly
            180                 185                 190

Asp Gly Tyr Leu Cys Val Ser Gly Lys Gly Pro Thr Asp Arg Glu Trp
        195                 200                 205

Lys Leu Leu Pro Ala Val Arg Glu Gly Ala Ala Ala Gly Arg Asp
    210                 215                 220

Ala Asp Glu Ile Lys Arg Thr Ile Glu Ile Lys Leu Ser Phe Asp Asp
225                 230                 235                 240

Asp Val Ala Ala Ala Leu Arg Glu Glu Arg Val Trp Ala Gly Leu Ala
            245                 250                 255

Leu Thr Ala Ala Gln Lys His Ser Val Trp Asp Pro Val Ala Ala Pro
            260                 265                 270

Asp Asp Ala Asp Glu Leu Ile Arg Glu Leu Val Ala Lys Leu Val Ile
        275                 280                 285

Val Gly Ser Pro Glu Glu Val Ala Ala Glu Leu Val Lys Trp Gly Glu
    290                 295                 300

Ala Trp Gly Leu Asp Tyr Ala Leu Phe His Leu Pro Gly Gly Asp Gln
305                 310                 315                 320

Asp Arg Leu Leu Glu Leu Phe Gly Glu Arg Val Glu Ala Leu Gly Arg
                325                 330                 335

Ala

<210> SEQ ID NO 8
<211> LENGTH: 339
<212> TYPE: PRT
<213> ORGANISM: Artificial Sequence
<220> FEATURE:
<223> OTHER INFORMATION: reconstructed sequence -continued

<400> SEQUENCE: 8

```
Met Thr Phe Thr Phe Gly Gly Pro Leu Ala Asp Lys Gly Ser Gly Pro
1               5                   10                  15

Gln Phe Ala Pro Ala Ala Glu Val Leu Asp Asp Tyr Val Ala Leu Ala
            20                  25                  30

Glu Ala Ala Glu Arg Ala Gly Phe Asn Leu Trp Thr Pro Tyr Trp His
        35                  40                  45

Pro Leu Glu Asn Thr Gly Pro Phe Pro Glu Trp Trp Met Trp Leu Leu
    50                  55                  60

Gly Ala Ala Ala Thr Thr Ser Arg Leu Arg Leu Gly Thr Leu Val Leu
65                  70                  75                  80

Ser Pro Thr Phe Asn Asn Pro Val Arg Val Ala Glu Gln Phe Ala Thr
                85                  90                  95

Val Asp Gln Leu Ser Gly Gly Arg Leu Asp Leu Gly Leu Gly Ala Gly
            100                 105                 110

Ser Gly His Asn Glu Tyr Ala Ala Phe Gly Phe Asp Tyr Pro Glu Lys
        115                 120                 125

Lys Glu Arg Phe Ala Arg Leu Ala Glu Ser Val Arg Ile Phe Arg Glu
    130                 135                 140

Glu Trp Thr Gly Thr Thr Lys Ser Phe Ser Gly Glu Tyr Tyr Thr Val
145                 150                 155                 160

Asn Asp Ala Tyr Phe Tyr Pro Arg Pro Glu Gln Pro Val Pro Leu
                165                 170                 175

Ile Ala Ala Gly Gly Pro Thr Val Ala Lys Arg Ala Gly Arg Ile Gly
            180                 185                 190

Asp Gly Phe Leu Cys Thr Ser Gly Lys Gly Met Asp Glu Tyr Arg Glu
        195                 200                 205

Lys Leu Leu Thr Ala His Ala Glu Ala Gly Ala Ala Gly Gln Arg Pro
    210                 215                 220

Asp Ala Leu Arg Arg Arg Val Gly Ile Lys Leu Asn Pro Tyr Glu Val
225                 230                 235                 240

Asp Glu Lys Ala Ala Leu Glu Glu Thr Gly Ile Asp Ala Trp Leu Pro
                245                 250                 255

Leu Phe Ala Asp Gln Lys Pro Ser Val Val Gly Pro Arg Glu Met Pro
            260                 265                 270

Val Asp Ala Arg Asp Leu Pro Arg Arg Glu Ala Leu Arg Arg Trp Ile
        275                 280                 285

Ala Ser Ser Thr Pro Asp Leu Ile Ala Glu Leu Ile Lys Pro His Val
    290                 295                 300

Asp Ala Gly Leu Phe His Leu Val Phe Ala Ala Pro Gly His Asp Gln
305                 310                 315                 320

Asp Arg Phe Leu Glu Leu Phe Asp Glu Asp Val Ala Gln Tyr Ala Arg
                325                 330                 335

Ser Leu Gly
```

<210> SEQ ID NO 9
<211> LENGTH: 339
<212> TYPE: PRT
<213> ORGANISM: Artificial Sequence
<220> FEATURE:
<223> OTHER INFORMATION: reconstructed sequence -continued

```
<400> SEQUENCE: 9

Met Thr Asp Thr Ser Pro Ala Thr Leu Ser Glu Ile Gly Thr Ser Ala
1               5                   10                  15

Gln Phe Ala Pro Ala Asp Leu Val Asp Leu Val Val Ala Ala Glu Gln
            20                  25                  30

Ala Gly Phe Ala Gly Val Gly Phe Ser Asp Trp Asp His Phe Trp Ser
        35                  40                  45

Pro Leu Glu Gly Lys Gly Thr Trp Ser Glu Ala Met Gly Trp Leu Ala
    50                  55                  60

Ala Leu Ser Arg Thr Ala Gly Arg Lys Ala Leu Gly Thr Leu Val Leu
65                  70                  75                  80

Ser Asn Ser Phe Arg Pro Gln Val Val Phe Ala Arg His Ala Thr Thr
                85                  90                  95

Val Ala Leu Leu Ser Gly Arg Arg Val Leu Leu Gly Leu Gly Ala Gly
            100                 105                 110

Gly Val Asp Arg Leu Ala Gly Gly Val Glu Gly Asp Trp Pro Glu Pro
        115                 120                 125

Arg Glu Arg Tyr Glu Arg Leu Arg Glu Ser Val Glu Ile Ile Arg Arg
    130                 135                 140

Leu Trp Thr Gly Glu Thr Val Ser Phe Asp Gly Glu Tyr Tyr Arg Thr
145                 150                 155                 160

His Asp Ala Tyr Gly Tyr Pro Val Ser Glu Gln Gly Pro Val Pro Ile
                165                 170                 175

Ile Val Ala Gly Ser Pro Glu Val Ala Lys Arg Ala Ala Arg Val Gly
            180                 185                 190

Asp Gly Phe Leu Cys Phe Ser Gly Ser Gly Pro Asp Ala Tyr Asp Glu
        195                 200                 205

Ser Leu Leu Pro Ala Phe Lys Ala Gly Ala Ala Ala Gly Gly Arg Asp
    210                 215                 220

Asp Ala Phe Arg Asp Arg Val Ile Glu Leu Lys Ser Tyr Tyr Asp Val
225                 230                 235                 240

Ala Glu Arg Ala Ala Leu Glu Glu Thr Arg Gly Trp Ala Pro Leu Ser
                245                 250                 255

Leu Ala Arg Asp Gln Lys His Ser Val Ala Asp Pro Val Ala Met Pro
            260                 265                 270

Gly Arg Asp Asp Glu Leu Val Lys Glu Gln Val Ala Lys Arg Trp Ile
        275                 280                 285

Val Gly Ser Ser Pro Asp Glu Ala Val Ala Ala Ile Gln Pro Tyr Val
    290                 295                 300

Asp Ala Gly Leu Phe His Leu Val Phe His Ala Pro Gly Gly Asp Gln
305                 310                 315                 320

Asp Arg Phe Leu Glu Leu Phe Asp Glu Asp Val Arg Ala Tyr Leu Arg
                325                 330                 335

Ser Leu Ala

<210> SEQ ID NO 10
<211> LENGTH: 367
<212> TYPE: PRT
<213> ORGANISM: Yersinia enterocolitica
```

<400> SEQUENCE: 10

```
Met Lys Ile Gly Val Phe Ile Pro Ile Gly Asn Asn Gly Trp Leu Ile
1               5                   10                  15

Ser Ser Asn Ala Pro Gln Tyr Met Pro Ser Phe Glu Leu Asn Lys Ala
                20                  25                  30

Ile Val Gln Gln Ala Glu His Tyr Gln Phe Asp Phe Ala Leu Ser Met
                35                  40                  45

Ile Lys Leu Arg Gly Phe Gly Gly Lys Thr Glu Phe Trp Asp His Asn
        50                  55                  60

Leu Glu Ser Phe Thr Leu Met Ala Gly Leu Ala Ala Val Thr Ser Arg
65                  70                  75                  80

Ile Lys Ile Tyr Ala Thr Ala Ala Thr Leu Thr Leu Pro Pro Ala Ile
                85                  90                  95

Val Ala Arg Met Ala Ser Thr Ile Asp Ser Ile Ser Asn Gly Arg Phe
                100                 105                 110

Gly Leu Asn Val Val Thr Gly Trp Gln Lys Pro Glu Tyr Glu Gln Met
        115                 120                 125

Gly Leu Trp Pro Gly Asp Glu Tyr Phe Ser Arg Arg Tyr Asp Tyr Leu
        130                 135                 140

Ser Glu Tyr Val Glu Val Leu Gln Asp Phe Trp Gly Thr Gly Gln Ser
145                 150                 155                 160

Asp Phe Asn Gly Glu Phe Phe Gln Met Asp Asp Cys Arg Val Ser Pro
                165                 170                 175

Gln Pro Gln Thr Pro Ile Lys Leu Ile Cys Ala Ala Gln Ser Asp Ala
                180                 185                 190

Gly Met Ala Phe Ser Ala Lys Tyr Ala Asp Tyr Asn Phe Cys Phe Gly
        195                 200                 205

Lys Gly Val Asn Thr Pro Thr Ala Phe Ala Pro Thr Ala Ala Arg Leu
        210                 215                 220

Gln Lys Ala Ala Glu Gln Ala Gly Arg Glu Val Ser Ser Tyr Val Leu
225                 230                 235                 240

Phe Met Ile Ile Ala Asp Glu Thr Asp Glu Leu Ala Arg Ala Lys Trp
                245                 250                 255

Glu Ser Tyr Lys Ala Gly Ala Asp Thr Glu Ala Leu Ala Trp Leu Thr
                260                 265                 270

Glu Gln Ser Gly Lys Asp Thr Gln Ser Gly Ala Asp Thr Asn Val Arg
        275                 280                 285

Gln Met Ala Asp Pro Thr Ser Ala Val Asn Ile Asn Met Gly Thr Leu
        290                 295                 300

Val Gly Ser Tyr Ala Asn Val Ala Lys Met Met Asp Asp Ile Ala Thr
305                 310                 315                 320

Val Pro Gly Thr Glu Gly Ile Leu Leu Thr Phe Asp Asp Phe Leu Ser
                325                 330                 335

Gly Ile Glu Asn Phe Gly Gln His Ile Gln Pro Leu Met Asn Ser Arg
        340                 345                 350

Ala Asp Ile Val Asp Thr Leu Pro Pro Ala Ala Arg Glu Val Ala
        355                 360                 365
```

<210> SEQ ID NO 11
<211> LENGTH: 367
<212> TYPE: PRT
<213> ORGANISM: Artificial Sequence
<220> FEATURE:
<223> OTHER INFORMATION: reconstructed sequence

<400> SEQUENCE: 11

```
Met Lys Ile Gly Val Phe Ile Pro Ile Gly Asn Asn Gly Trp Leu Ile
1               5                  10                 15

Ser Thr Asn Ala Pro Gln Tyr Met Pro Ser Phe Glu Leu Asn Lys Ala
                20                 25                 30

Ile Val Gln Lys Ala Glu His Tyr Gln Phe Asp Phe Ala Leu Ser Met
            35                 40                 45

Ile Lys Leu Arg Gly Phe Gly Gly Lys Thr Glu Phe Trp Asp His Asn
        50                 55                 60

Leu Glu Ser Phe Thr Leu Met Ala Gly Leu Ala Ala Val Thr Ser Arg
65                 70                 75                 80

Ile Lys Ile Tyr Ala Thr Ala Ala Thr Leu Thr Leu Pro Pro Ala Ile
                85                 90                 95

Val Ala Arg Met Ala Ser Thr Ile Asp Ser Ile Ser Asn Gly Arg Phe
            100                105                110

Gly Leu Asn Val Val Thr Gly Trp Gln Lys Pro Glu Tyr Glu Gln Met
        115                120                125

Gly Leu Trp Pro Gly Asp Glu Tyr Phe Ser Arg Arg Tyr Asp Tyr Leu
    130                135                140

Ser Glu Tyr Val Gln Val Leu Arg Asp Leu Trp Gly Thr Gly Lys Ser
145                150                155                160

Asp Phe Lys Gly Glu Phe Phe Gln Met Asp Asp Cys Arg Val Ser Pro
                165                170                175

Gln Pro Gln Ala Pro Ile Lys Val Ile Cys Ala Gly Gln Ser Asp Ala
            180                185                190

Gly Met Ala Phe Ser Ala Lys Tyr Ala Asp Tyr Asn Phe Cys Phe Gly
        195                200                205

Lys Gly Val Asn Thr Pro Thr Ala Phe Ala Pro Thr Ala Ala Arg Met
    210                215                220

Lys Glu Ala Ala Glu Lys Ala Gly Arg Asp Val Ser Ser Tyr Val Leu
225                230                235                240

Phe Met Ile Ile Ala Asp Glu Thr Asp Glu Ala Ala Arg Ala Lys Trp
                245                250                255

Glu Ser Tyr Lys Ala Gly Ala Asp Thr Glu Ala Leu Ala Trp Leu Thr
            260                265                270

Glu Gln Ser Gly Lys Asp Thr Lys Ser Gly Ala Asp Thr Asn Val Arg
        275                280                285

Gln Met Ala Asp Pro Thr Ser Ala Val Asn Ile Asn Met Gly Thr Leu
    290                295                300

Val Gly Ser Tyr Ala Asn Val Ala Arg Met Met Asp Glu Ile Ala Thr
305                310                315                320

Val Pro Gly Thr Glu Gly Ile Leu Leu Thr Phe Asp Asp Phe Leu Ser
                325                330                335

Gly Ile Glu Asn Phe Gly Gln Arg Ile Gln Pro Leu Met Lys Ser Arg
            340                345                350

Ala Asp Ile Ile Pro Thr Thr Pro Glu Ala Ala Arg Glu Val Ala
        355                360                365
```

<210> SEQ ID NO 12
<211> LENGTH: 393
<212> TYPE: PRT
<213> ORGANISM: Artificial Sequence
<220> FEATURE:
<223> OTHER INFORMATION: generated sequence -continued

<400> SEQUENCE: 12

```
Met Pro Val Ser Trp Leu Leu Leu Gly His Ser Ser Gly Val Gly Leu
1               5                   10                  15

Gly Gly Pro Asp Ala Ala Ala Ala Ala Glu Gly Ala Tyr Gly Phe Arg
            20                  25                  30

Ala Ala Val Val Ala Glu Arg Val Gly Phe Asp Gly Val Leu Leu Gly
        35                  40                  45

Ala Arg Gly Ser Pro Glu Tyr Pro Ala Thr Val Ala Arg Leu Leu Ala
    50                  55                  60

Glu Ala Ala Leu His Gln Leu Arg Leu Gly Ala Gly Val Thr Ala Thr
65                  70                  75                  80

Ser Thr Tyr Ala Pro Ala Ala Gly Val Glu Val Leu Gly Thr Leu Ala
                85                  90                  95

Ser Leu Phe Pro Arg Asp Ile Ile Leu Gly Leu Gly Ile Ser Thr Gly
            100                 105                 110

Ala Arg His Asp Glu Ala Gly Gly Arg Asp His Phe Gln Arg Trp Glu
        115                 120                 125

Gly Asp Phe Gly Asp His Tyr Pro Ala Val Arg Gly Ala Leu Gly Leu
    130                 135                 140

Trp Thr Asp Glu Glu Val Leu Arg Glu Ala Ser Phe Ala Ser Pro Tyr
145                 150                 155                 160

Tyr Pro Arg Gly Val Glu Gly Trp Arg Val Val Ser Pro Arg Pro
                165                 170                 175

Pro Arg Ala Gly Leu Trp Leu Gly Glu Lys Pro Glu Asp Val Gly Val
            180                 185                 190

Leu Gly Asp Asp Val Ala Leu Leu His Ala Phe Arg Pro Val Phe Gly
            195                 200                 205

Arg Ser Gly Pro Ala Val Ala Gly Leu Leu Gly Ala Asp Val Pro Ala
    210                 215                 220

Trp Ala Pro Ala Gly Leu His Pro Ile Val Asp Val Arg Leu Ile Trp
225                 230                 235                 240

Gly Gly Ser Pro Ser Asp Ala Gln Phe Leu Ala Asp Leu Glu Arg Ala
            245                 250                 255

Glu Ala Leu Ala Phe Ala Arg Ala Glu Gly Met Arg Gly Val Glu Ala
        260                 265                 270

Glu Pro Thr Arg Arg Leu Leu Ala Glu Ala Thr Ser Gly Ala Pro Asp
    275                 280                 285

Glu Ala Ala Ala Gly Thr Leu Ala Ala Gln Gln Val Asp Val Glu Ile
    290                 295                 300

Asp Gly Thr Pro Trp Trp Ala Glu Thr Pro Arg Thr Val Ser Ala Gly
305                 310                 315                 320

Leu Gly Ala Ala Glu Leu Gly Thr Arg Leu Val Ala Val Gly Leu Asp
            325                 330                 335

Ala Val Ala Thr Gly Ala Thr Ser Val Asp Gly Trp Ser Thr Val Gly
        340                 345                 350

Gly Leu Ala Gly Gly Gly Asp Gly Phe Trp Ile Gly Pro Glu Leu Tyr
        355                 360                 365

Ala Asp Gly Ala Arg Arg Gly Ala Ala Phe Asp Gly Asp Val Ala Ser
    370                 375                 380

Leu Ser Pro Gly Arg Val Ala Asp His
385                 390
```

-continued

<210> SEQ ID NO 13
<211> LENGTH: 339
<212> TYPE: PRT
<213> ORGANISM: Streptomyces sp. AA4

<400> SEQUENCE: 13

Met Asp Thr Arg Thr Ser Gly Ile Thr Ile Gly Tyr Lys Ala Ser Ala
1               5                   10                  15

Glu Gln Phe Gly Pro Arg His Leu Val Glu Leu Ala Val Leu Ala Glu
                20                  25                  30

Arg Arg Gly Phe Asp Ser Val Leu Val Ser Asp His Tyr Gln Pro Trp
            35                  40                  45

Arg His Arg Asn Gly His Ala Pro Phe Ser Met Ala Trp Leu Ala Ala
        50                  55                  60

Ala Gly Glu Arg Thr Glu Arg Val Arg Leu Gly Thr Ser Val Leu Thr
65                  70                  75                  80

Ala Thr Phe Arg Tyr His Pro Ala Val Val Ala Gln Ala Phe Gly Thr
                85                  90                  95

Leu Gly Ala Leu Cys Pro Gly Arg Val Met Leu Gly Leu Gly Thr Gly
                100                 105                 110

Glu Ala Leu Asn Glu Val Ala Val Ala Arg Met Glu Trp Pro Gly Phe
            115                 120                 125

Glu Glu Arg Phe Ala Arg Leu Arg Glu Ala Ile Asp Leu Ile Arg Arg
        130                 135                 140

Leu Trp Thr Glu Glu Arg Val Ser Phe Asp Gly Glu Tyr Tyr Arg Thr
145                 150                 155                 160

Glu Asn Ala Thr Val Tyr Asp Arg Pro Ser Arg Pro Val Pro Val Tyr
                165                 170                 175

Val Ala Ala Gly Gly Pro Val Val Ala Lys Tyr Ala Gly Arg Ile Ala
                180                 185                 190

Asp Gly Phe Ile Cys Thr Ser Gly Lys Gly Met Glu Leu Tyr Thr Glu
            195                 200                 205

Lys Leu Gln Pro Ala Val Asp Ala Gly Ala Glu Ala Gly Arg Glu Pro
        210                 215                 220

Ala Asp Val Ala Arg Thr Ile Glu Ile Lys Leu Ser Tyr Asp Thr Asp
225                 230                 235                 240

Ala Glu Ala Ala Ala Glu Asn Thr Arg Phe Trp Ala Pro Leu Ser Leu
                245                 250                 255

Thr Ala Asp Gln Lys His Gly Val Ser Asp Pro Leu Ala Met Glu Arg
                260                 265                 270

Ala Ala Asp Glu Leu Pro Met Ser Gln Ile Ala Ser Arg Trp Ile Val
            275                 280                 285

Ser Ser Asp Pro Asp Glu Val Val Glu Arg Ile Arg Pro Tyr Val Asp
        290                 295                 300

Ala Gly Phe Thr Asp Leu Val Leu His Ala Pro Gly His Asp Gln Ala
305                 310                 315                 320

Arg Phe Leu Glu Leu Ala Arg Gln Asp Leu Leu Pro Arg Leu Arg Asn
                325                 330                 335

Leu Gly Gly

<210> SEQ ID NO 14
<211> LENGTH: 53
<212> TYPE: DNA
<213> ORGANISM: Artificial Sequence
<220> FEATURE:
<223> OTHER INFORMATION: Primer

<400> SEQUENCE: 14
taatataata gcgaacgttg agtactaaag tttccaaatt tcatagagag tcc          53

<210> SEQ ID NO 15
<211> LENGTH: 53
<212> TYPE: DNA
<213> ORGANISM: Artificial Sequence
<220> FEATURE:
<223> OTHER INFORMATION: Primer

<400> SEQUENCE: 15
ctatgaaatt tggaaacttt agtactcaac gttcgctatt atattagcta agg          53

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
tcatttcgaa ccccagagtc                                              20

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
cgccttcttg acgagttctt                                              20

<210> SEQ ID NO 18
<211> LENGTH: 40
<212> TYPE: DNA
<213> ORGANISM: Artificial Sequence
<220> FEATURE:
<223> OTHER INFORMATION: Primer

<400> SEQUENCE: 18
tctatcaaca ggagtccaag cgagctcgat atcaaattac                        40

<210> SEQ ID NO 19
<211> LENGTH: 41
<212> TYPE: DNA
<213> ORGANISM: Artificial Sequence
<220> FEATURE:
<223> OTHER INFORMATION: Primer

<400> SEQUENCE: 19
ttttgaattc gacgtcgacg tcgatatctg gcgaaaatga g                      41

<210> SEQ ID NO 20
<211> LENGTH: 40
<212> TYPE: DNA
<213> ORGANISM: Artificial Sequence
<220> FEATURE:
<223> OTHER INFORMATION: Primer

<400> SEQUENCE: 20
atcgagctcg cttggactcc tgttgataga tccagtaatg                        40

<210> SEQ ID NO 21

```
<211> LENGTH: 40
<212> TYPE: DNA
<213> ORGANISM: Artificial Sequence
<220> FEATURE:
<223> OTHER INFORMATION: Primer

<400> SEQUENCE: 21
ccagatatcg acgtcgacgt cgaattcaaa agatcttaag                              40

<210> SEQ ID NO 22
<211> LENGTH: 42
<212> TYPE: DNA
<213> ORGANISM: Artificial Sequence
<220> FEATURE:
<223> OTHER INFORMATION: Primer

<400> SEQUENCE: 22
cacaggagac tttctaatga aatttggaaa cttttttgctt ac                         42

<210> SEQ ID NO 23
<211> LENGTH: 39
<212> TYPE: DNA
<213> ORGANISM: Artificial Sequence
<220> FEATURE:
<223> OTHER INFORMATION: Primer

<400> SEQUENCE: 23
ctcgacaacc gatccctaat ataatagcga acgttgttt                              39

<210> SEQ ID NO 24
<211> LENGTH: 41
<212> TYPE: DNA
<213> ORGANISM: Artificial Sequence
<220> FEATURE:
<223> OTHER INFORMATION: Primer

<400> SEQUENCE: 24
gtttccaaat ttcattagaa agtctcctgt gcatgattaa g                          41

<210> SEQ ID NO 25
<211> LENGTH: 38
<212> TYPE: DNA
<213> ORGANISM: Artificial Sequence
<220> FEATURE:
<223> OTHER INFORMATION: Primer

<400> SEQUENCE: 25
tcgctattat attagggatc ggttgtcgag taaggatc                              38

<210> SEQ ID NO 26
<211> LENGTH: 29
<212> TYPE: DNA
<213> ORGANISM: Artificial Sequence
<220> FEATURE:
<223> OTHER INFORMATION: Primer

<400> SEQUENCE: 26
cattagaaag tctcctgtgc atgattaag                                        29

<210> SEQ ID NO 27
<211> LENGTH: 23
<212> TYPE: DNA
<213> ORGANISM: Artificial Sequence
<220> FEATURE:
<223> OTHER INFORMATION: Primer
```

-continued

<400> SEQUENCE: 27
ggatcggttg tcgagtaagg atc                                                    23

<210> SEQ ID NO 28
<211> LENGTH: 33
<212> TYPE: DNA
<213> ORGANISM: Artificial Sequence
<220> FEATURE:
<223> OTHER INFORMATION: Primer

<400> SEQUENCE: 28
caattttcgt actgaaacat cttaatcatg cac                                          33

<210> SEQ ID NO 29
<211> LENGTH: 25
<212> TYPE: DNA
<213> ORGANISM: Artificial Sequence
<220> FEATURE:
<223> OTHER INFORMATION: Primer

<400> SEQUENCE: 29
cgttttattt gatgcctgga gatcc                                                   25

<210> SEQ ID NO 30
<211> LENGTH: 360
<212> TYPE: PRT
<213> ORGANISM: Artificial Sequence
<220> FEATURE:
<223> OTHER INFORMATION: reconstructed sequence

<400> SEQUENCE: 30

Met Lys Phe Gly Asn Phe Leu Leu Thr Tyr Gln Pro Pro Gln Phe Ser
1               5                   10                  15

Gln Thr Glu Val Met Lys Arg Leu Val Lys Leu Gly Arg Val Ser Glu
            20                  25                  30

Glu Cys Gly Phe Asp Thr Val Trp Leu Leu Glu His His Phe Thr Glu
        35                  40                  45

Phe Gly Leu Leu Gly Asn Pro Tyr Val Ala Ala Ala Tyr Leu Leu Gly
    50                  55                  60

Ala Thr Lys Lys Leu Asn Val Gly Thr Ala Ala Ile Val Leu Pro Thr
65                  70                  75                  80

Ala His Pro Val Arg Gln Leu Glu Asp Val Asn Leu Leu Asp Gln Met
                85                  90                  95

Ser Lys Gly Arg Phe Arg Phe Gly Ile Cys Arg Gly Leu Tyr Asn Lys
            100                 105                 110

Asp Phe Arg Val Phe Gly Val Asp Met Asn Asn Thr Arg Ala Leu Met
            115                 120                 125

Glu Cys Trp Tyr Gly Leu Ile Lys Asn Gly Met Thr Glu Gly Tyr Val
    130                 135                 140

Glu Ala Asp Asn Glu His Ile Lys Phe His Lys Val Lys Val Asn Pro
145                 150                 155                 160

Thr Ala Tyr Ser Gln Gly Gly Ala Pro Val Tyr Val Val Ala Glu Ser
                165                 170                 175

Ala Ser Thr Thr Glu Trp Ala Ala Gln His Gly Leu Pro Met Ile Leu
            180                 185                 190

Ser Trp Ile Ile Asn Thr Asn Glu Lys Lys Ala Gln Leu Glu Leu Tyr
            195                 200                 205

```
Asn Glu Val Ala Gln Glu Tyr Gly His Asp Val His Asn Ile Asp His
    210             215                 220
Cys Leu Ser Tyr Ile Thr Ser Val Asp His Asp Ser Ile Lys Ala Lys
225             230                 235                 240
Glu Ile Cys Arg Asn Phe Leu Gly His Trp Tyr Asp Ser Tyr Val Asn
            245                 250                 255
Ala Thr Thr Ile Phe Asp Asp Ser Asp Gln Thr Lys Gly Tyr Asp Phe
            260                 265                 270
Asn Lys Gly Gln Trp Arg Asp Phe Val Leu Lys Gly His Lys Asp Thr
            275                 280                 285
Asn Arg Arg Ile Asp Tyr Ser Tyr Glu Ile Asn Pro Val Gly Thr Pro
    290             295                 300
Lys Glu Cys Ile Asp Ile Ile Gln Thr Asp Ile Asp Ala Thr Gly Ile
305             310                 315                 320
Ser Asn Ile Cys Cys Gly Phe Glu Ala Asn Gly Thr Val Asp Glu Ile
            325                 330                 335
Ile Ala Ser Met Lys Leu Phe Gln Ser Asp Val Met Pro Phe Leu Lys
            340                 345                 350
Glu Lys Gln Arg Ser Leu Leu Tyr
    355                 360
```

```
<210> SEQ ID NO 31
<211> LENGTH: 359
<212> TYPE: PRT
<213> ORGANISM: Artificial Sequence
<220> FEATURE:
<223> OTHER INFORMATION: reconstructed sequence

<400> SEQUENCE: 31

Met Lys Phe Gly Asn Phe Leu Leu Thr Tyr Gln Pro Pro Gln Phe Ser
1               5                   10                  15
Gln Thr Glu Val Met Gln Arg Leu Val Asn Leu Gly Arg Ala Ser Glu
            20                  25                  30
Glu Cys Gly Phe Asp Thr Val Trp Leu Leu Glu His His Phe Thr Glu
            35                  40                  45
Phe Gly Leu Leu Gly Asn Pro Tyr Val Ala Ala Tyr Leu Leu Gly
    50                  55                  60
Ala Thr Lys His Leu Asn Val Gly Thr Ala Ala Ile Val Leu Pro Thr
65              70                  75                  80
Ala His Pro Val Arg Gln Leu Glu Asp Val Asn Leu Leu Asp Gln Met
            85                  90                  95
Ser Lys Gly Arg Phe Arg Phe Gly Ile Cys Arg Gly Leu Tyr Asn Lys
            100                 105                 110
Asp Phe Asn Val Phe Gly Val Asp Met Asn Asn Thr Arg Ala Leu Thr
            115                 120                 125
Glu Cys Trp Tyr Gly Leu Ile Lys Asn Gly Met Thr Glu Gly Tyr Met
    130             135                 140
Glu Ala Asp Asn Glu His Ile Lys Phe His Lys Val Lys Val Asn Pro
145             150                 155                 160
Thr Ala Tyr Ser Lys Gly Gly Ala Pro Val Tyr Val Val Ala Glu Ser
            165                 170                 175
Ala Ser Thr Thr Glu Trp Ala Ala Gln His Gly Leu Pro Met Ile Leu
            180                 185                 190
Ser Trp Ile Ile Asn Thr Asn Glu Lys Lys Ala Gln Ile Asp Leu Tyr
    195             200                 205
```

-continued

```
Asn Glu Val Ala Gln Glu His Gly His Asp Val His Asn Ile Asp His
    210             215                 220

Cys Leu Ser Tyr Ile Thr Ser Val Asp His Asp Ser Lys Lys Ala Lys
225             230                 235                 240

Glu Ile Cys Arg Asp Phe Leu Gly His Trp Tyr Asp Ser Tyr Val Asn
            245             250                 255

Ala Thr Thr Ile Phe Asp Asp Ser Asp Gln Thr Lys Gly Tyr Gly Phe
            260             265                 270

Asn Lys Gly Gln Trp His Asp Phe Val Leu Lys Gly His Lys Asp Thr
        275             280                 285

Asn Arg Arg Val Asp Tyr Ser Tyr Glu Ile Asn Pro Val Gly Thr Pro
    290             295                 300

Gln Glu Cys Ile Asp Ile Ile Gln Thr Asp Ile Asp Ala Thr Gly Ile
305             310                 315                 320

Ser Asn Ile Cys Cys Gly Phe Glu Ala Asn Gly Thr Val Asp Glu Ile
            325             330                 335

Ile Ala Ser Met Lys Leu Phe Gln Ser Asp Val Met Pro Phe Leu Lys
            340             345                 350

Glu Lys Gln Arg Ser Leu Leu
        355
```

```
<210> SEQ ID NO 32
<211> LENGTH: 359
<212> TYPE: PRT
<213> ORGANISM: Artificial Sequence
<220> FEATURE:
<223> OTHER INFORMATION: reconstructed sequence

<400> SEQUENCE: 32

Met Lys Phe Gly Asn Phe Leu Leu Thr Tyr Gln Pro Pro Gln Phe Ser
1               5                   10                  15

Gln Thr Glu Val Met Gln Arg Leu Val Lys Leu Gly Arg Val Ser Glu
            20                  25                  30

Glu Cys Gly Phe Asp Thr Val Trp Leu Leu Glu His His Phe Thr Glu
        35                  40                  45

Phe Gly Leu Leu Gly Asn Pro Tyr Val Ala Ala Ala Tyr Leu Leu Gly
    50                  55                  60

Ala Thr Lys Lys Leu Asn Val Gly Thr Ala Ala Ile Val Leu Pro Thr
65                  70                  75                  80

Ala His Pro Val Arg Gln Leu Glu Asp Val Asn Leu Leu Asp Gln Met
            85                  90                  95

Ser Lys Gly Arg Phe Arg Phe Gly Ile Cys Arg Gly Leu Tyr Asn Lys
            100                 105                 110

Asp Phe Arg Val Phe Gly Val Asp Met Asn Asn Thr Arg Ala Leu Met
            115                 120                 125

Glu Cys Trp Tyr Gly Leu Ile Lys Asn Gly Met Thr Glu Gly Tyr Met
    130                 135                 140

Glu Ala Asp Asn Glu His Ile Lys Phe His Lys Val Lys Val Asn Pro
145                 150                 155                 160

Thr Ala Tyr Thr Gln Gly Gly Ala Pro Ile Tyr Val Val Ala Glu Ser
                165                 170                 175

Ala Ser Thr Thr Glu Trp Ala Ala Gln Phe Gly Leu Pro Met Ile Leu
            180                 185                 190

Ser Trp Ile Ile Asn Thr Asn Glu Lys Ile Ala Gln Leu Glu Leu Tyr
        195                 200                 205
```

```
Asn Glu Val Ala Gln Glu Tyr Gly His Asp Val His Asn Ile Asp His
    210             215             220
```

```
Cys Leu Ser Tyr Ile Thr Ser Val Asp His Asp Ser Ile Lys Ala Lys
225             230             235             240
```

```
Glu Ile Cys Arg Gln Phe Leu Gly His Trp Tyr Asp Ser Tyr Val Asn
            245             250             255
```

```
Ala Thr Thr Ile Phe Asp Asp Ser Asp Gln Thr Lys Gly Tyr Asp Phe
            260             265             270
```

```
Asn Lys Gly Gln Trp Arg Asp Phe Val Leu Lys Gly His Lys Asp Thr
            275             280             285
```

```
Asn Arg Arg Ile Asp Tyr Ser Tyr Glu Ile Asn Pro Val Gly Thr Pro
    290             295             300
```

```
Lys Glu Cys Ile Asp Ile Ile Gln Thr Asp Ile Asp Ala Thr Gly Ile
305             310             315             320
```

```
Ser Asn Ile Cys Cys Gly Phe Glu Ala Asn Gly Thr Val Asp Glu Ile
            325             330             335
```

```
Ile Ala Ser Met Lys Leu Phe Gln Ser Asp Val Met Pro Phe Leu Lys
            340             345             350
```

```
Glu Lys Gln Arg Ser Leu Leu
        355
```

```
<210> SEQ ID NO 33
<211> LENGTH: 359
<212> TYPE: PRT
<213> ORGANISM: Artificial Sequence
<220> FEATURE:
<223> OTHER INFORMATION: reconstructed sequence
```

```
<400> SEQUENCE: 33
```

```
Met Lys Phe Gly Asn Phe Leu Leu Thr Tyr Gln Pro Pro Gln Phe Ser
1               5               10              15
```

```
Gln Thr Glu Val Met Gln Arg Leu Val Lys Leu Gly Arg Val Ser Glu
            20              25              30
```

```
Glu Cys Gly Phe Asp Thr Val Trp Leu Leu Glu His His Phe Thr Glu
        35              40              45
```

```
Phe Gly Leu Leu Gly Asn Pro Tyr Val Ala Ala Ala Tyr Leu Leu Gly
    50              55              60
```

```
Ala Thr Lys Lys Leu Asn Val Gly Thr Ala Ala Ile Val Leu Pro Thr
65              70              75              80
```

```
Ala His Pro Val Arg Gln Leu Glu Asp Val Asn Leu Leu Asp Gln Met
            85              90              95
```

```
Ser Lys Gly Arg Phe Arg Phe Gly Ile Cys Arg Gly Leu Tyr Asn Lys
            100             105             110
```

```
Asp Phe Arg Val Phe Gly Val Asp Met Asn Asn Thr Arg Ala Leu Met
            115             120             125
```

```
Glu Cys Trp Tyr Gly Leu Ile Lys Asn Gly Met Thr Glu Gly Tyr Val
    130             135             140
```

```
Glu Ala Asp Asn Glu His Ile Lys Phe His Lys Val Lys Val Asn Pro
145             150             155             160
```

```
Thr Ala Tyr Ser Gln Gly Gly Ala Pro Val Tyr Val Val Ala Glu Ser
            165             170             175
```

```
Ala Ser Thr Thr Glu Trp Ala Ala Gln His Gly Leu Pro Met Ile Leu
            180             185             190
```

```
Ser Trp Ile Ile Asn Thr Asn Glu Lys Ile Ala Gln Ile Glu Leu Tyr
    195             200             205
```

```
Asn Glu Val Ala Gln Glu Tyr Gly His Asp Ile His Asn Ile Asp His
    210             215                 220
```

```
Cys Leu Ser Tyr Ile Thr Ser Val Asp His Asp Ser Ile Lys Ala Lys
225             230                 235                 240
```

```
Glu Ile Cys Arg Asn Phe Leu Gly His Trp Tyr Asp Ser Tyr Val Asn
                245                 250                 255
```

```
Ala Thr Thr Ile Phe Asp Asp Ser Asp Lys Thr Lys Gly Tyr Gly Phe
                260             265                 270
```

```
Asn Lys Gly Gln Trp Arg Asp Phe Val Leu Lys Gly His Lys Asp Thr
            275             280             285
```

```
Asn Arg Arg Ile Asp Tyr Ser Tyr Glu Ile Asn Pro Val Gly Thr Pro
    290             295                 300
```

```
Lys Glu Cys Ile Asp Ile Ile Gln Thr Asp Ile Asp Ala Thr Gly Ile
305             310                 315                 320
```

```
Ser Asn Ile Cys Cys Gly Phe Glu Ala Asn Gly Thr Val Asp Glu Ile
                325             330                 335
```

```
Ile Ala Ser Met Lys Leu Phe Gln Ser Asp Val Met Pro Phe Leu Lys
                340             345                 350
```

```
Glu Thr Gln Arg Ser Leu Leu
            355
```

```
<210> SEQ ID NO 34
<211> LENGTH: 360
<212> TYPE: PRT
<213> ORGANISM: Artificial Sequence
<220> FEATURE:
<223> OTHER INFORMATION: reconstructed sequence

<400> SEQUENCE: 34
```

```
Met Lys Phe Gly Asn Phe Leu Leu Thr Tyr Gln Pro Pro Gln Leu Asp
1               5                   10                  15
```

```
Gln Ser Glu Val Met Ala Arg Leu Val Lys Leu Gly Arg Val Ser Glu
            20                  25                  30
```

```
Glu Cys Gly Phe Asp Thr Val Trp Leu Leu Glu His His Phe Thr Glu
            35                  40                  45
```

```
Phe Gly Leu Leu Gly Asn Pro Tyr Val Ala Ala Ala Tyr Leu Leu Gly
    50                  55                  60
```

```
Ala Thr Lys Lys Leu Asn Val Gly Thr Ala Ala Ile Val Leu Pro Thr
65              70                  75                  80
```

```
Ala His Pro Val Arg Gln Leu Glu Asp Val Asn Leu Leu Asp Gln Met
                85                  90                  95
```

```
Ser Lys Gly Arg Phe Arg Phe Gly Ile Cys Arg Gly Leu Tyr Asn Lys
            100                 105                 110
```

```
Asp Phe Arg Val Phe Gly Val Asp Met Asn Asn Ser Arg Ala Leu Met
            115                 120                 125
```

```
Glu Cys Trp Tyr Asp Leu Ile Lys Glu Gly Met Thr Glu Gly Tyr Val
    130                 135                 140
```

```
Glu Ala Asp Thr Glu His Ile Lys Phe His Lys Val Lys His Leu Pro
145             150                 155                 160
```

```
Thr Ala Tyr Ser Gln Gly Gly Ala Pro Val Tyr Val Val Ala Glu Ser
            165                 170                 175
```

```
Ala Ser Thr Thr Glu Trp Ala Ala Gln His Gly Leu Pro Met Ile Leu
            180                 185                 190
```

```
Ser Trp Ile Ile Asn Thr Asn Glu Lys Lys Ala Gln Leu Glu Leu Tyr
            195                 200                 205
```

```
Asn Glu Val Ala Gln Glu Tyr Gly His Asp Ile His Asn Ile Asp His
    210             215             220
Cys Leu Ser Tyr Ile Thr Ser Val Asp His Asp Ser Ile Arg Ala Lys
225             230             235             240
Glu Lys Cys Val Asn His Leu Gly His Trp Tyr Asp Ser Tyr Val Asn
            245             250             255
Ala Thr Thr Ile Phe Asp Asp Ser Asp Gln Thr Lys Gly Tyr Gly Phe
            260             265             270
Asn Lys Gly Gln Trp Arg Asp Phe Val Leu Lys Gly His Lys Asp Thr
        275             280             285
Asn Arg Arg Ile Asp Tyr Ser Tyr Glu Ile Asn Pro Val Gly Thr Pro
    290             295             300
Asn Glu Cys Ile Asp Ile Ile Gln Thr Asp Ile Asp Ala Thr Gly Ile
305             310             315             320
Ser Asn Ile Cys Cys Gly Phe Glu Ala Asn Gly Thr Val Asp Glu Arg
            325             330             335
Ile Ala Ser Met Leu Leu Phe Gln Ser Asp Val Met Pro Phe Leu Lys
            340             345             350
Glu Lys Gln Arg Ser Leu Leu Tyr
        355             360
```

```
<210> SEQ ID NO 35
<211> LENGTH: 360
<212> TYPE: PRT
<213> ORGANISM: Artificial Sequence
<220> FEATURE:
<223> OTHER INFORMATION: reconstructed sequence

<400> SEQUENCE: 35
```

```
Met Lys Phe Gly Asn Phe Leu Leu Thr Tyr Gln Pro Pro Gln Phe Ser
1               5               10              15
Gln Thr Glu Val Met Gln Arg Leu Val Lys Leu Gly Arg Val Ser Glu
            20              25              30
Glu Cys Gly Phe Asp Thr Val Trp Leu Leu Glu His His Phe Thr Glu
        35              40              45
Phe Gly Leu Leu Gly Asn Pro Tyr Val Ala Ala Ala Tyr Leu Leu Gly
    50              55              60
Ala Thr Lys Lys Leu Asn Val Gly Thr Ala Ala Ile Val Leu Pro Thr
65              70              75              80
Ala His Pro Val Arg Gln Leu Glu Asp Val Asn Leu Leu Asp Gln Met
            85              90              95
Ser Lys Gly Arg Phe Arg Phe Gly Ile Cys Arg Gly Leu Tyr Asn Lys
            100             105             110
Asp Phe Arg Val Phe Gly Val Asp Met Asn Asn Thr Arg Ala Leu Met
            115             120             125
Glu Cys Trp Tyr Gly Leu Ile Lys Asn Gly Met Thr Glu Gly Tyr Val
    130             135             140
Glu Ala Asp Asn Glu His Ile Lys Phe His Lys Val Lys Val Asn Pro
145             150             155             160
Thr Ala Tyr Ser Gln Gly Gly Ala Pro Val Tyr Val Val Ala Glu Ser
            165             170             175
Ala Ser Thr Thr Glu Trp Ala Ala Gln Phe Gly Leu Pro Met Ile Leu
            180             185             190
Ser Trp Ile Ile Asn Thr Asn Glu Lys Lys Ala Gln Leu Glu Leu Tyr
    195             200             205
```

```
Asn Glu Val Ala Gln Glu Tyr Gly His Asp Ile His Asn Ile Asp His
    210             215                 220
Cys Leu Ser Tyr Ile Thr Ser Val Asp His Asp Ser Ile Lys Ala Lys
225                 230                 235                 240
Glu Ile Cys Arg Asn Phe Leu Gly His Trp Tyr Asp Ser Tyr Val Asn
                245                 250                 255
Ala Thr Thr Ile Phe Asp Asp Ser Asp Gln Thr Lys Gly Tyr Gly Phe
                260                 265                 270
Asn Lys Gly Gln Trp Arg Asp Phe Val Leu Lys Gly His Lys Asn Thr
                275                 280                 285
Asn Arg Arg Ile Asp Tyr Ser Tyr Glu Ile Asn Pro Val Gly Thr Pro
    290                 295                 300
Lys Glu Cys Ile Asp Ile Ile Gln Thr Asp Ile Asp Ala Thr Gly Ile
305                 310                 315                 320
Ser Asn Ile Cys Cys Gly Phe Glu Ala Asn Gly Thr Val Asp Glu Ile
                325                 330                 335
Ile Ala Ser Met Lys Leu Phe Gln Ser Asp Val Met Pro Phe Leu Lys
                340                 345                 350
Glu Lys Gln Arg Ser Leu Leu Tyr
        355                 360

<210> SEQ ID NO 36
<211> LENGTH: 359
<212> TYPE: PRT
<213> ORGANISM: Artificial Sequence
<220> FEATURE:
<223> OTHER INFORMATION: reconstructed sequence

<400> SEQUENCE: 36

Met Lys Phe Gly Asn Phe Leu Leu Thr Tyr Gln Pro Pro Gln Phe Ser
1               5                   10                  15
Gln Thr Glu Val Met Lys Arg Leu Val Lys Leu Gly Arg Val Ser Glu
                20                  25                  30
Glu Cys Gly Phe Asp Thr Val Trp Leu Leu Glu His His Phe Thr Glu
            35                  40                  45
Phe Gly Leu Leu Gly Asn Pro Tyr Val Ala Ala Ala Tyr Leu Leu Gly
    50                  55                  60
Ala Thr Lys Lys Leu Asn Val Gly Thr Ala Ala Ile Val Leu Pro Thr
65                  70                  75                  80
Ala His Pro Val Arg Gln Leu Glu Asp Val Asn Leu Leu Asp Gln Met
                85                  90                  95
Ser Lys Gly Arg Phe Arg Phe Gly Ile Cys Arg Gly Leu Tyr Asn Lys
                100                 105                 110
Asp Phe Arg Val Phe Gly Val Asp Met Asp Asn Thr Arg Ala Leu Met
            115                 120                 125
Glu Cys Trp Tyr Gly Leu Ile Lys Asn Gly Met Thr Glu Gly Tyr Val
    130                 135                 140
Glu Ala Asp Asn Glu His Ile Lys Phe His Lys Val Lys Val Asn Pro
145                 150                 155                 160
Thr Ala Tyr Ser Gln Gly Gly Ala Pro Ile Tyr Val Val Ala Glu Ser
                165                 170                 175
Ala Ser Thr Thr Glu Trp Ala Ala Gln His Gly Leu Pro Met Ile Leu
            180                 185                 190
Ser Trp Ile Ile Asn Thr Asn Glu Lys Lys Ala Gln Leu Glu Leu Tyr
    195                 200                 205
```

```
Asn Glu Val Ala Gln Glu His Gly His Asp Val His Asn Ile Asp His
    210             215             220
```

```
Cys Leu Ser Tyr Ile Thr Ser Val Asp His Asp Ser Ile Lys Ala Lys
225             230             235             240
```

```
Glu Ile Cys Arg Asn Phe Leu Gly His Trp Tyr Asp Ser Tyr Val Asn
            245             250             255
```

```
Ala Thr Thr Ile Phe Asp Asp Ser Asp Gln Thr Lys Gly Tyr Gly Phe
            260             265             270
```

```
Asn Lys Gly Gln Trp Arg Asp Phe Val Leu Lys Gly His Lys Asp Thr
            275             280             285
```

```
Asn Arg Arg Ile Asp Tyr Ser Tyr Glu Ile Asn Pro Val Gly Thr Pro
    290             295             300
```

```
Lys Glu Cys Ile Asp Ile Ile Gln Thr Asp Ile Asp Ala Thr Gly Ile
305             310             315             320
```

```
Ser Asn Ile Cys Cys Gly Phe Glu Ala Asn Gly Thr Val Asp Glu Ile
            325             330             335
```

```
Ile Ala Ser Met Lys Leu Phe Gln Ser Asp Val Met Pro Phe Leu Lys
            340             345             350
```

```
Glu Lys Gln Arg Ser Leu Leu
        355
```

```
<210> SEQ ID NO 37
<211> LENGTH: 360
<212> TYPE: PRT
<213> ORGANISM: Artificial Sequence
<220> FEATURE:
<223> OTHER INFORMATION: reconstructed sequence

<400> SEQUENCE: 37
```

```
Met Lys Phe Gly Asn Phe Leu Leu Thr Tyr Gln Pro Pro Gln Phe Ser
1               5               10              15
```

```
Gln Thr Glu Val Met Gln Arg Leu Val Lys Leu Gly Arg Val Ser Glu
            20              25              30
```

```
Glu Cys Gly Phe Asp Thr Val Trp Leu Leu Glu His His Phe Thr Glu
        35              40              45
```

```
Phe Gly Leu Leu Gly Asn Pro Tyr Val Ala Ala Ala Tyr Leu Leu Gly
    50              55              60
```

```
Ala Thr Lys Lys Leu Asn Val Gly Thr Ala Ala Ile Val Leu Pro Thr
65              70              75              80
```

```
Ala His Pro Val Arg Gln Leu Glu Asp Val Asn Leu Leu Asp Gln Met
            85              90              95
```

```
Ser Lys Gly Arg Phe Arg Phe Gly Ile Cys Arg Gly Leu Tyr Asn Lys
            100             105             110
```

```
Asp Phe Arg Val Phe Gly Val Asp Met Asn Asn Thr Arg Ala Leu Met
            115             120             125
```

```
Glu Cys Trp Tyr Gly Leu Ile Lys Asn Gly Met Thr Glu Gly Tyr Met
    130             135             140
```

```
Glu Ala Asp Asn Glu His Ile Lys Phe His Lys Val Lys Val Asn Pro
145             150             155             160
```

```
Thr Ala Tyr Ser Gln Gly Gly Ala Pro Val Tyr Val Val Ala Glu Ser
            165             170             175
```

```
Ala Ser Thr Thr Glu Trp Ala Ala Gln His Gly Leu Pro Met Ile Leu
            180             185             190
```

```
Ser Trp Ile Ile Asn Thr Asn Glu Lys Lys Ala Gln Leu Glu Leu Tyr
    195             200             205
```

```
Asn Glu Val Ala Gln Glu His Gly His Asp Ile His Asn Ile Asp His
    210             215             220

Cys Leu Ser Tyr Ile Thr Ser Val Asp His Asp Ser Ile Lys Ala Lys
225             230             235             240

Glu Ile Cys Arg Asn Phe Leu Gly His Trp Tyr Asp Ser Tyr Val Asn
            245             250             255

Ala Thr Thr Ile Phe Asp Asp Ser Asp Gln Thr Lys Gly Tyr Asp Phe
            260             265             270

Asn Lys Gly Gln Trp Arg Asp Phe Val Leu Lys Gly His Lys Asp Thr
        275             280             285

Asn Arg Arg Ile Asp Tyr Ser Tyr Glu Ile Asn Pro Val Gly Thr Pro
    290             295             300

Lys Glu Cys Ile Asp Ile Ile Gln Thr Asp Ile Asp Ala Thr Gly Ile
305             310             315             320

Ser Asn Ile Cys Cys Gly Phe Glu Ala Asn Gly Thr Val Asp Glu Ile
            325             330             335

Ile Ala Ser Met Lys Leu Phe Gln Ser Asp Val Met Pro Phe Leu Lys
            340             345             350

Glu Lys Gln Arg Ser Leu Leu Tyr
        355             360

<210> SEQ ID NO 38
<211> LENGTH: 360
<212> TYPE: PRT
<213> ORGANISM: Artificial Sequence
<220> FEATURE:
<223> OTHER INFORMATION: reconstructed sequence

<400> SEQUENCE: 38

Met Lys Phe Gly Asn Phe Leu Leu Thr Tyr Gln Pro Pro Gln Leu Pro
1               5               10              15

Gln Thr Glu Val Met Lys Arg Leu Val Lys Leu Gly Arg Val Ser Glu
            20              25              30

Gly Cys Gly Phe Asp Thr Val Trp Leu Leu Glu His His Phe Thr Glu
        35              40              45

Phe Gly Leu Leu Gly Asn Pro Tyr Val Ala Ala Ala His Leu Leu Gly
    50              55              60

Ala Thr Lys Lys Leu Asn Val Gly Thr Ala Ala Ile Val Leu Pro Thr
65              70              75              80

Ala His Pro Ile Arg Gln Leu Glu Asp Val Asn Leu Leu Asp Gln Met
            85              90              95

Ser Lys Gly Arg Phe Arg Phe Gly Ile Cys Arg Gly Leu Tyr Asn Lys
            100             105             110

Asp Phe Arg Val Phe Gly Thr Asp Met Asn Asn Ser Arg Val Leu Met
            115             120             125

Glu Cys Trp Tyr Gly Leu Ile Lys Asn Gly Met Thr Glu Gly Tyr Met
    130             135             140

Glu Ala Asp Asn Glu His Ile Lys Phe His Lys Val Lys Val Asn Pro
145             150             155             160

Thr Ala Tyr Ser Arg Gly Gly Ala Pro Val Tyr Val Val Ala Glu Ser
            165             170             175

Ala Ser Thr Thr Glu Trp Ala Ala Gln Phe Gly Leu Pro Met Ile Leu
            180             185             190

Ser Trp Ile Ile Asn Thr Asn Glu Lys Lys Ala Gln Ala Glu Leu Tyr
    195             200             205
```

-continued

```
Asn Glu Val Ala Leu Glu Tyr Gly Arg Asp Ile His Asn Ile Asp His
    210                 215                 220
```

```
Cys Leu Ser Tyr Ile Thr Ser Val Asp His Asp Ser Ile Lys Ala Lys
225                 230                 235                 240
```

```
Glu Ile Cys Arg Asn Phe Leu Gly His Trp Tyr Asp Ser Tyr Val Asn
                245                 250                 255
```

```
Ala Thr Thr Ile Phe Asp Asp Ser Asp Gln Thr Lys Gly Tyr Asp Phe
                260                 265                 270
```

```
Asn Lys Gly Gln Trp Arg Asp Phe Val Leu Lys Gly His Lys Asp Thr
                275                 280                 285
```

```
Asn Arg Arg Ile Asp Tyr Ser Tyr Glu Ile Asn Pro Val Gly Thr Pro
    290                 295                 300
```

```
Glu Glu Cys Ile Asp Ile Ile Gln Thr Asp Ile Asp Ala Thr Gly Ile
305                 310                 315                 320
```

```
Ser Asn Ile Cys Cys Gly Phe Glu Ala Asn Gly Thr Val Asp Glu Ile
                325                 330                 335
```

```
Ile Ala Ser Met Lys Leu Phe Gln Ser Asp Val Met Pro Phe Leu Lys
                340                 345                 350
```

```
Glu Lys Gln Arg Ser Leu Leu Tyr
        355                 360
```

```
<210> SEQ ID NO 39
<211> LENGTH: 360
<212> TYPE: PRT
<213> ORGANISM: Artificial Sequence
<220> FEATURE:
<223> OTHER INFORMATION: reconstructed sequence

<400> SEQUENCE: 39
```

```
Met Lys Phe Gly Asn Phe Leu Leu Thr Tyr Gln Pro Pro Gln Phe Ser
1                 5                   10                  15
```

```
Gln Thr Glu Val Met Lys Arg Leu Val Lys Leu Gly Arg Val Ser Glu
                20                  25                  30
```

```
Glu Cys Gly Phe Asp Thr Val Trp Leu Leu Glu His His Phe Thr Glu
            35                  40                  45
```

```
Phe Gly Leu Leu Gly Asn Pro Tyr Val Ala Ala Ala Tyr Leu Leu Gly
    50                  55                  60
```

```
Ala Thr Lys Lys Leu Asn Val Gly Thr Ala Ala Ile Val Leu Pro Thr
65                  70                  75                  80
```

```
Ala His Pro Val Arg Gln Leu Glu Asp Val Asn Leu Leu Asp Gln Met
                85                  90                  95
```

```
Ser Lys Gly Arg Phe Arg Phe Gly Ile Cys Arg Gly Leu Tyr Asn Lys
                100                 105                 110
```

```
Asp Phe Arg Val Phe Gly Val Asp Met Asn Asn Ser Arg Ala Leu Met
                115                 120                 125
```

```
Glu Cys Trp Tyr Gly Leu Ile Lys Asn Gly Met Thr Glu Gly Tyr Val
    130                 135                 140
```

```
Glu Ala Asp Asn Glu His Ile Lys Phe His Lys Val Lys Val Asn Pro
145                 150                 155                 160
```

```
Thr Ala Tyr Ser Gln Gly Gly Ala Pro Ile Tyr Val Val Ala Glu Ser
                165                 170                 175
```

```
Ala Ser Thr Thr Glu Trp Ala Ala Gln His Gly Leu Pro Met Ile Leu
                180                 185                 190
```

```
Ser Trp Ile Ile Asn Thr Asn Glu Lys Lys Ala Gln Leu Glu Phe Tyr
    195                 200                 205
```

```
Asn Glu Val Ala Gln Glu Tyr Gly His Asp Ile His Asn Ile Asp His
    210             215             220
```

```
Cys Leu Ser Tyr Ile Thr Ser Val Asp His Asp Ser Ile Lys Ala Lys
225             230             235             240
```

```
Glu Ile Cys Arg Asn Phe Leu Gly His Trp Tyr Asp Ser Tyr Val Asn
            245             250             255
```

```
Ala Thr Thr Ile Phe Asp Asp Ser Asp Gln Thr Lys Gly Tyr Gly Phe
            260             265             270
```

```
Asn Lys Gly Gln Trp Arg Asp Phe Val Leu Lys Gly His Lys Asn Thr
            275             280             285
```

```
Asn Arg Arg Ile Asp Tyr Ser Tyr Glu Ile Asn Pro Val Gly Thr Pro
    290             295             300
```

```
Lys Glu Cys Ile Asp Ile Ile Gln Thr Asp Ile Asp Ala Thr Gly Ile
305             310             315             320
```

```
Ser Asn Ile Cys Cys Gly Phe Glu Ala Asn Gly Thr Val Asp Glu Ile
            325             330             335
```

```
Ile Ala Ser Met Lys Leu Phe Gln Ser Asp Val Met Pro Phe Leu Lys
            340             345             350
```

```
Glu Lys Gln Arg Ser Leu Leu Tyr
        355             360
```

<210> SEQ ID NO 40
<211> LENGTH: 360
<212> TYPE: PRT
<213> ORGANISM: Artificial Sequence
<220> FEATURE:
<223> OTHER INFORMATION: reconstructed sequence

<400> SEQUENCE: 40

```
Met Lys Phe Gly Asn Phe Leu Leu Thr Tyr Gln Pro Pro Glu Phe Ser
1               5               10              15
```

```
Gln Thr Glu Val Met Lys Arg Leu Val Lys Leu Gly Arg Val Ser Glu
            20              25              30
```

```
Glu Cys Gly Phe Asp Glu Val Trp Leu Leu Glu His His Phe Thr Glu
        35              40              45
```

```
Phe Gly Leu Leu Gly Asn Pro Tyr Val Ala Ala Ala His Leu Leu Gly
    50              55              60
```

```
Ala Thr Lys Lys Leu Asn Val Gly Thr Ala Ala Ile Val Leu Pro Thr
65              70              75              80
```

```
Ala His Pro Val Arg Gln Leu Glu Asp Val Asn Leu Leu Asp Gln Met
            85              90              95
```

```
Ser Lys Gly Arg Phe Arg Phe Gly Ile Cys Arg Gly Leu Tyr Asn Lys
            100             105             110
```

```
Asp Phe Arg Val Phe Gly Val Asp Met Asn Asn Ser Arg Val Leu Met
            115             120             125
```

```
Glu Cys Trp Tyr Gly Leu Met Lys Asn Gly Met Thr Glu Gly Tyr Met
    130             135             140
```

```
Glu Ala Asp Asn Glu His Ile Lys Phe His Lys Val Lys Val Asn Pro
145             150             155             160
```

```
Thr Ala Tyr Thr Gln Gly Gly Ala Pro Ile Tyr Val Val Ala Glu Ser
            165             170             175
```

```
Ala Ser Thr Thr Glu Trp Ala Ala Gln His Gly Leu Pro Met Ile Leu
            180             185             190
```

```
Ser Trp Ile Ile Asn Asn Asn Glu Lys Ile Tyr Gln Ala Lys Phe Tyr
    195             200             205
```

```
Asn Glu Val Ala Gln Glu Ser Gly His Asp Ile His Asn Ile Asp His
    210             215             220
```

```
Cys Leu Ser Tyr Ile Thr Ser Val Asp His Asp Ser Ile Lys Ala Lys
225             230             235             240
```

```
Glu Ile Cys Arg Asn Phe Leu Gly His Trp Tyr Asp Ser Tyr Val Asn
            245             250             255
```

```
Ala Thr Thr Ile Phe Asp Asp Ser Asp Lys Thr Lys Gly Tyr Asp Phe
            260             265             270
```

```
Asn Lys Gly Gln Trp Arg Asp Phe Val Leu Lys Gly His Lys Asp Thr
            275             280             285
```

```
Asn Arg Arg Ile Asp Tyr Ser Tyr Glu Ile Asn Pro Val Gly Thr Pro
    290             295             300
```

```
Lys Glu Cys Ile Asp Ile Ile Gln Thr Asp Ile Asp Ala Thr Gly Ile
305             310             315             320
```

```
Ser Ile Asn Cys Cys Gly Phe Glu Ala Asn Gly Thr Val Asp Glu Ile
            325             330             335
```

```
Ile Ala Ser Met Lys Leu Phe Gln Ser Asp Val Met Pro Phe Leu Lys
            340             345             350
```

```
Glu Lys Gln Arg Ser Leu Leu Tyr
        355             360
```

```
<210> SEQ ID NO 41
<211> LENGTH: 360
<212> TYPE: PRT
<213> ORGANISM: Artificial Sequence
<220> FEATURE:
<223> OTHER INFORMATION: reconstructed sequence

<400> SEQUENCE: 41
```

```
Met Lys Phe Gly Asn Phe Leu Leu Thr Tyr Gln Pro Pro Gln Phe Ser
1               5               10              15
```

```
Gln Thr Glu Val Met Lys Arg Leu Val Lys Leu Gly Arg Val Ser Glu
            20              25              30
```

```
Glu Cys Gly Phe Asp Thr Val Trp Leu Leu Glu His His Phe Thr Glu
        35              40              45
```

```
Phe Gly Leu Leu Gly Asn Pro Tyr Val Ala Ala Ala Tyr Leu Leu Gly
    50              55              60
```

```
Ala Thr Lys Lys Leu Asn Val Gly Thr Ala Ala Ile Val Leu Pro Thr
65              70              75              80
```

```
Ala His Pro Val Arg Gln Leu Glu Asp Val Asn Leu Leu Asp Gln Met
            85              90              95
```

```
Ser Lys Gly Arg Phe Arg Phe Gly Ile Cys Arg Gly Leu Tyr Asn Lys
            100             105             110
```

```
Asp Phe Arg Val Phe Gly Val Asp Met Asn Asn Thr Arg Ala Leu Met
            115             120             125
```

```
Glu Cys Trp Tyr Gly Leu Ile Lys Asn Gly Met Thr Glu Gly Tyr Met
    130             135             140
```

```
Glu Ala Asp Asn Glu His Ile Lys Phe His Lys Val Lys Val Asn Pro
145             150             155             160
```

```
Thr Ala Tyr Ser Lys Gly Gly Ala Pro Ile Tyr Val Val Ala Glu Ser
            165             170             175
```

```
Ala Ser Thr Thr Glu Trp Ala Ala Gln Phe Gly Leu Pro Met Ile Leu
            180             185             190
```

```
Ser Trp Ile Ile Asn Thr Asn Glu Lys Lys Ala Gln Leu Glu Leu Tyr
    195             200             205
```

```
Asn Glu Val Ala Arg Glu Tyr Gly His Asp Ile His Asn Ile Asp His
    210                 215                 220
Cys Leu Ser Tyr Ile Thr Ser Val Asp His Asp Ser Ile Lys Ala Lys
225                 230                 235                 240
Glu Ile Cys Arg Gln Phe Leu Gly His Trp Tyr Asp Ser Tyr Val Asn
                245                 250                 255
Ala Thr Thr Ile Phe Asp Asp Ser Asp Gln Thr Lys Gly Tyr Gly His
                260                 265                 270
Asn Lys Gly Gln Trp Arg Asp Phe Val Leu Lys Gly His Lys Asp Thr
            275                 280                 285
Asn Arg Arg Ile Asp Tyr Ser Tyr Glu Ile Asn Pro Leu Gly Thr Pro
    290                 295                 300
Lys Glu Cys Ile Asp Ile Ile Gln Thr Asp Ile Asp Ala Thr Gly Ile
305                 310                 315                 320
Ser Asn Ile Cys Cys Gly Phe Glu Ala Asn Gly Thr Val Asp Glu Ile
                325                 330                 335
Ile Ala Ser Met Lys Leu Phe Gln Ser Asp Val Met Pro Phe Leu Lys
                340                 345                 350
Glu Thr Gln Arg Ser Leu Leu Tyr
            355                 360
```

<210> SEQ ID NO 42
<211> LENGTH: 360
<212> TYPE: PRT
<213> ORGANISM: Artificial Sequence
<220> FEATURE:
<223> OTHER INFORMATION: reconstructed sequence

<400> SEQUENCE: 42

```
Met Lys Phe Gly Asn Phe Leu Leu Thr Tyr Gln Pro Pro Gln Phe Pro
1                   5                   10                  15
Gln Thr Glu Val Met Gln Arg Leu Val Lys Leu Gly Arg Val Ser Glu
                20                  25                  30
Glu Cys Gly Phe Asp Thr Val Trp Leu Leu Glu His His Phe Thr Glu
            35                  40                  45
Phe Gly Leu Leu Gly Asn Pro Tyr Val Ala Ala Ala Tyr Leu Leu Gly
    50                  55                  60
Ala Thr Lys Lys Leu Asn Val Gly Thr Ala Val Ile Val Leu Pro Thr
65                  70                  75                  80
Ala His Pro Val Arg Gln Leu Glu Asp Val Asn Leu Leu Asp Gln Met
                85                  90                  95
Ser Lys Gly Arg Phe Arg Phe Gly Ile Cys Arg Gly Leu Tyr Asn Lys
                100                 105                 110
Asp Phe Arg Val Phe Gly Val Asp Met Asn Asn Thr Arg Ala Leu Met
            115                 120                 125
Glu Cys Trp Tyr Gly Leu Ile Lys Arg Gly Met Thr Glu Gly Tyr Val
    130                 135                 140
Glu Ala Asp Asn Glu His Ile Lys Phe His Lys Val Lys Val Asn Pro
145                 150                 155                 160
Thr Ala Tyr Ser Gln Gly Gly Ala Pro Ile Tyr Val Val Ala Glu Ser
                165                 170                 175
Ala Ser Thr Thr Glu Trp Ala Ala Gln His Gly Leu Pro Met Ile Leu
            180                 185                 190
Ser Trp Ile Ile Asn Thr Asn Glu Lys Lys Ala Gln Leu Glu Leu Tyr
    195                 200                 205
```

-continued

```
Asn Glu Val Ala Gln Glu His Gly His Asp Ile His Asn Ile Asp His
    210                 215                 220
```

```
Cys Leu Ser Tyr Ile Thr Ser Val Asp His Asp Ser Ile Lys Ala Lys
225                 230                 235                 240
```

```
Glu Ile Cys Arg Gln Phe Leu Gly His Trp Tyr Asp Ser Tyr Val Asn
                245                 250                 255
```

```
Ala Thr Thr Ile Phe Asp Asp Ser Asp Gln Thr Lys Gly Tyr Gly Phe
                260                 265                 270
```

```
Asn Lys Gly Gln Trp Arg Asp Phe Val Leu Lys Gly His Lys Asp Thr
                275                 280                 285
```

```
Asn Arg Arg Ile Asp Tyr Ser Tyr Glu Ile Asn Pro Val Gly Thr Pro
    290                 295                 300
```

```
Lys Glu Cys Ile Asp Ile Ile Gln Thr Asp Ile Asp Ala Thr Gly Ile
305                 310                 315                 320
```

```
Ser Asn Ile Cys Cys Gly Phe Glu Ala Asn Gly Thr Val Asn Glu Ile
                325                 330                 335
```

```
Ile Ala Ser Met Lys Leu Phe Gln Ser Asp Val Met Pro Phe Leu Lys
                340                 345                 350
```

```
Glu Lys Gln Arg Ser Leu Leu Tyr
        355                 360
```

```
<210> SEQ ID NO 43
<211> LENGTH: 360
<212> TYPE: PRT
<213> ORGANISM: Artificial Sequence
<220> FEATURE:
<223> OTHER INFORMATION: reconstructed sequence

<400> SEQUENCE: 43
```

```
Met Lys Phe Gly Asn Phe Leu Leu Thr Tyr Gln Pro Pro Gln Phe Ser
1               5                   10                  15
```

```
Gln Thr Glu Val Met Lys Arg Leu Val Lys Leu Gly Arg Val Ser Glu
                20                  25                  30
```

```
Glu Cys Gly Phe Asp Thr Val Trp Leu Leu Glu His His Phe Thr Glu
            35                  40                  45
```

```
Phe Gly Leu Leu Gly Asn Pro Tyr Val Ala Ala Ala Tyr Leu Leu Gly
    50                  55                  60
```

```
Ala Thr Lys Lys Leu Asn Val Gly Thr Ala Ala Ile Val Leu Pro Thr
65                  70                  75                  80
```

```
Ala His Pro Val Arg Gln Leu Glu Asp Val Asn Leu Leu Asp Gln Met
                85                  90                  95
```

```
Ser Lys Gly Arg Phe Arg Phe Gly Ile Cys Arg Gly Leu Tyr Asn Lys
                100                 105                 110
```

```
Asp Phe Arg Val Phe Gly Val Asp Met Asn Asn Thr Arg Ala Leu Met
            115                 120                 125
```

```
Glu Cys Trp Tyr Gly Leu Ile Lys Asn Gly Met Thr Glu Gly Tyr Met
    130                 135                 140
```

```
Glu Ala Asp Asn Glu His Ile Lys Phe His Lys Val Lys Val Asn Pro
145                 150                 155                 160
```

```
Thr Ala Tyr Ser Gln Gly Gly Ala Pro Ile Tyr Val Val Ala Glu Ser
                165                 170                 175
```

```
Ala Ser Thr Thr Glu Trp Ala Ala Gln Phe Gly Leu Pro Met Ile Leu
            180                 185                 190
```

```
Ser Trp Ile Ile Asn Thr Asn Glu Lys Lys Ala Gln Leu Glu Leu Tyr
    195                 200                 205
```

-continued

```
Asn Glu Val Ala Gln Glu Tyr Gly His Asp Ile His Asn Ile Asp His
    210             215             220
```

```
Cys Leu Ser Tyr Ile Thr Ser Val Asp His Asp Ser Ile Lys Ala Lys
225             230             235             240
```

```
Glu Ile Cys Arg Asn Phe Leu Gly His Trp Tyr Asp Ser Tyr Val Asn
                245             250             255
```

```
Ala Thr Thr Ile Phe Asp Asp Ser Asp Gln Thr Lys Gly Tyr Asp Phe
                260             265             270
```

```
Asn Lys Gly Gln Trp Arg Asp Phe Val Leu Lys Gly His Lys Asp Thr
            275             280             285
```

```
Asn Arg Arg Ile Asp Tyr Ser Tyr Glu Ile Asn Pro Val Gly Thr Pro
    290             295             300
```

```
Gln Glu Cys Ile Asp Ile Ile Gln Thr Asp Ile Asp Ala Thr Gly Ile
305             310             315             320
```

```
Ser Asn Ile Cys Cys Gly Phe Glu Ala Asn Gly Thr Val Asp Glu Ile
                325             330             335
```

```
Ile Ala Ser Met Lys Leu Phe Gln Ser Asp Val Met Pro Phe Leu Lys
                340             345             350
```

```
Glu Lys Gln Arg Ser Leu Leu Tyr
        355             360
```

```
<210> SEQ ID NO 44
<211> LENGTH: 360
<212> TYPE: PRT
<213> ORGANISM: Artificial Sequence
<220> FEATURE:
<223> OTHER INFORMATION: reconstructed sequence

<400> SEQUENCE: 44
```

```
Met Lys Phe Gly Asn Phe Leu Leu Thr Tyr Gln Pro Pro Gln Phe Ser
1               5               10              15
```

```
Gln Thr Glu Val Met Lys Arg Leu Val Lys Leu Gly Arg Val Ser Glu
            20              25              30
```

```
Glu Cys Gly Phe Asp Thr Val Trp Leu Leu Glu His His Phe Thr Glu
        35              40              45
```

```
Phe Gly Leu Leu Gly Asn Pro Tyr Val Ala Ala Ala Asn Leu Leu Gly
    50              55              60
```

```
Ala Thr Lys Lys Leu Asn Val Gly Thr Ala Ala Ile Val Leu Pro Thr
65              70              75              80
```

```
Ala His Pro Val Arg Gln Leu Glu Asp Val Asn Leu Leu Asp Gln Met
                85              90              95
```

```
Ser Lys Gly Arg Phe Arg Phe Gly Ile Cys Arg Gly Leu Tyr Asn Lys
            100             105             110
```

```
Asp Phe Arg Val Phe Gly Tyr Asp Met Asp Asn Thr Arg Ala Leu Met
            115             120             125
```

```
Glu Cys Trp Tyr Gly Leu Ile Lys Asn Gly Met Thr Glu Gly Tyr Met
    130             135             140
```

```
Glu Ala Asp Asn Glu His Ile Lys Phe Pro Lys Val His Val Asn Pro
145             150             155             160
```

```
Thr Ala Tyr Thr Gln Gly Gly Ala Pro Ile Tyr Val Val Ala Glu Ser
                165             170             175
```

```
Ala Ser Thr Thr Glu Trp Ala Ala Gln Phe Gly Leu Pro Met Ile Leu
            180             185             190
```

```
Ser Trp Ile Val Asn Lys Asn Glu Lys Ile Ala Gln Leu Asp Leu Tyr
            195             200             205
```

-continued

```
Asn Glu Val Ala Gln Glu His Gly His Asp Val His Asn Ile Asp His
    210             215             220

Cys Leu Ser Tyr Ile Thr Ser Val Asp His Asp Ser Val Lys Ala Lys
225             230             235             240

Glu Val Cys Glu Asn Phe Leu Gly His Trp Tyr Asp Ser Tyr Val Asn
            245             250             255

Ala Thr Thr Ile Phe Asp Asp Ser Asp Gln Thr Lys Gly Tyr Gly Phe
            260             265             270

Asn Lys Gly Gln Trp Arg Asp Phe Val Leu Lys Gly His Lys Asp Thr
    275             280             285

Asn Arg Arg Ile Asp Tyr Ser Tyr Glu Ile Asn Pro Val Gly Thr Pro
    290             295             300

Lys Glu Cys Ile Asp Ile Ile Gln Thr Asp Ile Asp Ala Thr Gly Ile
305             310             315             320

Ser Asn Ile Cys Cys Gly Phe Glu Ala Asn Gly Thr Val Asp Glu Ile
            325             330             335

Ile Ala Ser Met Lys Leu Phe Gln Ser Asp Val Met Pro Phe Leu Lys
            340             345             350

Glu Lys Gln Arg Ser Leu Leu Met
    355             360

<210> SEQ ID NO 45
<211> LENGTH: 360
<212> TYPE: PRT
<213> ORGANISM: Artificial Sequence
<220> FEATURE:
<223> OTHER INFORMATION: reconstructed sequence

<400> SEQUENCE: 45

Met Lys Phe Gly Asn Phe Leu Leu Thr Tyr Gln Pro Pro Gln Phe Ser
1               5               10              15

Gln Thr Glu Val Met Lys Arg Leu Val Lys Leu Gly Arg Val Ser Glu
            20              25              30

Glu Cys Gly Phe Asp Thr Val Trp Leu Leu Glu His His Phe Thr Glu
            35              40              45

Phe Gly Leu Leu Gly Asn Pro Tyr Val Ala Ala Ala Asn Leu Leu Gly
    50              55              60

Ala Thr Lys Lys Leu Asn Val Gly Thr Ala Ala Ile Val Leu Pro Thr
65              70              75              80

Ala His Pro Val Arg Gln Leu Glu Asp Val Asn Leu Leu Asp Gln Met
            85              90              95

Ser Lys Gly Arg Phe Arg Phe Gly Ile Cys Arg Gly Leu Tyr Asn Lys
            100             105             110

Asp Phe Arg Val Phe Gly Val Asp Met Asn Asn Thr Arg Ala Leu Met
            115             120             125

Glu Cys Trp Tyr Gly Leu Ile Lys Asn Gly Met Thr Glu Gly Tyr Val
    130             135             140

Glu Ala Asp Asn Glu His Ile Lys Phe His Lys Val Lys Leu Asn Pro
145             150             155             160

Thr Ala Tyr Ser Arg Gly Gly Ala Pro Ile Tyr Val Val Ala Glu Ser
            165             170             175

Ala Ser Thr Thr Glu Trp Ala Ala Gln His Gly Leu Pro Met Ile Leu
            180             185             190

Ser Trp Ile Ile Asn Thr Asn Glu Lys Lys Ala Gln Leu Asp Leu Tyr
    195             200             205
```

-continued

```
Asn Glu Val Ala Gln Glu His Gly His Asp Val His Asn Ile Asp His
    210             215             220
```

```
Cys Leu Ser Tyr Ile Thr Ser Val Asp His Asp Ser Ile Lys Ala Lys
225             230             235             240
```

```
Glu Ile Cys Arg Gln Phe Leu Gly His Trp Tyr Asp Ser Tyr Val Asn
            245             250             255
```

```
Ala Thr Thr Ile Phe Asp Asp Ser Asp Gln Thr Lys Gly Tyr Gly Phe
            260             265             270
```

```
Asn Lys Gly Gln Trp Arg Asp Phe Val Leu Lys Gly His Lys Asn Thr
            275             280             285
```

```
Asn Arg Arg Ile Asp Tyr Ser Tyr Glu Ile Asn Pro Val Gly Thr Pro
    290             295             300
```

```
Gln Glu Cys Ile Asp Ile Ile Gln Thr Asp Ile Asp Ala Thr Gly Ile
305             310             315             320
```

```
Ser Asn Ile Cys Cys Gly Phe Glu Ala Asn Gly Thr Val Asp Glu Ile
            325             330             335
```

```
Ile Ala Ser Met Lys Leu Phe Gln Ser Asp Val Met Pro Phe Leu Lys
            340             345             350
```

```
Glu Thr Gln Arg Ser Leu Leu Phe
            355             360
```

```
<210> SEQ ID NO 46
<211> LENGTH: 360
<212> TYPE: PRT
<213> ORGANISM: Artificial Sequence
<220> FEATURE:
<223> OTHER INFORMATION: reconstructed sequence
```

```
<400> SEQUENCE: 46
```

```
Met Lys Phe Gly Asn Phe Leu Leu Thr Tyr Gln Pro Pro Gln Phe Ser
1               5               10              15
```

```
Gln Thr Glu Val Met Gln Arg Leu Val Lys Leu Gly Arg Val Ser Glu
            20              25              30
```

```
Glu Cys Gly Phe Asp Thr Val Trp Leu Leu Glu His His Phe Thr Glu
            35              40              45
```

```
Phe Gly Leu Leu Gly Asn Pro Tyr Val Ala Ala Ala His Leu Leu Gly
    50              55              60
```

```
Ala Thr Lys Lys Leu Asn Val Gly Thr Ala Ala Ile Val Leu Pro Thr
65              70              75              80
```

```
Ala His Pro Val Arg Gln Leu Glu Asp Val Asn Leu Leu Asp Gln Met
            85              90              95
```

```
Ser Lys Gly Arg Phe Arg Phe Gly Ile Cys Arg Gly Leu Tyr Asn Lys
            100             105             110
```

```
Asp Phe Arg Val Phe Gly Thr Asp Met Asp Asn Ser Arg Ala Leu Met
            115             120             125
```

```
Glu Cys Trp Tyr Gly Leu Ile Lys Asn Gly Met Thr Glu Gly Tyr Val
    130             135             140
```

```
Glu Ala Asp Asn Glu His Ile Lys Phe Tyr Lys Val Lys Val Gly Pro
145             150             155             160
```

```
Thr Ala Tyr Ser Gln Gly Gly Ala Pro Ile Tyr Val Val Ala Glu Ser
            165             170             175
```

```
Ala Ser Thr Thr Glu Trp Ala Ala Gln His Gly Leu Pro Met Ile Leu
            180             185             190
```

```
Ser Trp Ile Ile Asn Thr Asn Lys Lys Ile Ala Gln Leu Asp Leu Tyr
    195             200             205
```

-continued

```
Asn Glu Val Ala Gln Glu Tyr Gly His Asp Val His Asn Ile Asp His
    210             215             220
```

```
Cys Leu Ser Tyr Ile Thr Ser Val Asp His Asp Ser Met Lys Ala Lys
225             230             235             240
```

```
Glu Ile Cys Arg Asn Phe Leu Gly His Trp Tyr Asp Ser Tyr Val Asn
            245             250             255
```

```
Ala Thr Thr Ile Phe Asp Asp Ser Asp Gln Thr Lys Gly Tyr Asp Phe
            260             265             270
```

```
Asn Lys Gly Lys Trp Arg Asp Phe Val Leu Lys Gly His Lys Asp Thr
            275             280             285
```

```
Asn Arg Arg Ile Asp Tyr Ser Tyr Glu Ile Asn Pro Val Glu Thr Val
    290             295             300
```

```
Lys Glu Tyr Ile Asp Ile Ile Gln Lys Asp Ile Asp Ala Thr Gly Ile
305             310             315             320
```

```
Ser Asn Ile Cys Cys Gly Phe Glu Ala Asn Gly Thr Val Asp Glu Ile
            325             330             335
```

```
Ile Ala Ser Met Lys Leu Phe Gln Ser Asp Val Met Pro Phe Leu Lys
            340             345             350
```

```
Glu Lys Gln Arg Ser Leu Leu Phe
        355             360
```

```
<210> SEQ ID NO 47
<211> LENGTH: 362
<212> TYPE: PRT
<213> ORGANISM: Artificial Sequence
<220> FEATURE:
<223> OTHER INFORMATION: reconstructed sequence

<400> SEQUENCE: 47
```

```
Met Arg Phe Gly Asn Phe Leu Leu Thr Tyr Gln Pro Pro Gln Phe Ser
1               5               10              15
```

```
Gln Thr Glu Val Met Lys Arg Leu Val Lys Leu Gly Arg Val Ser Glu
            20              25              30
```

```
Glu Cys Gly Phe Asp Thr Val Trp Leu Leu Glu His His Phe Thr Glu
        35              40              45
```

```
Phe Gly Leu Leu Gly Asn Pro Tyr Val Ala Ala Ala Tyr Leu Leu Gly
    50              55              60
```

```
Ala Thr Lys Lys Leu Asn Val Gly Thr Ala Ala Ile Val Leu Pro Thr
65              70              75              80
```

```
Ala His Pro Val Arg Gln Leu Glu Asp Val Asn Leu Leu Asp Gln Met
            85              90              95
```

```
Ser Lys Gly Arg Phe Arg Phe Gly Ile Cys Arg Gly Leu Tyr Asn Lys
            100             105             110
```

```
Asp Phe Asn Val Phe Gly Val Asp Met Asn Asn Thr Arg Ala Leu Thr
            115             120             125
```

```
Glu Cys Trp Tyr Gly Leu Ile Lys Asn Gly Met Thr Glu Gly Tyr Val
    130             135             140
```

```
Glu Ala Asp Asn Glu His Ile Lys Phe His Lys Val Lys Val Asn Pro
145             150             155             160
```

```
Thr Ala Tyr Thr Gln Gly Gly Ala Pro Ile Tyr Val Val Ala Glu Ser
            165             170             175
```

```
Ala Ser Thr Thr Glu Trp Ala Ala Gln His Gly Leu Pro Met Ile Leu
            180             185             190
```

```
Ser Trp Ile Ile Asn Thr Asn Glu Lys Ile Ala Gln Ala Asp Leu Tyr
    195             200             205
```

```
Asn Glu Val Ala Gln Glu Tyr Gly His Asp Val His Asn Ile Asp His
    210             215             220
```

```
Cys Leu Ser Tyr Ile Thr Ser Val Asp His Asp Ser Ile Lys Ala Lys
225             230             235             240
```

```
Glu Ile Cys Arg Asn Phe Leu Gly His Trp Tyr Asp Ser Tyr Val Asn
            245             250             255
```

```
Ala Thr Thr Ile Phe Asp Asp Ser Asp Gln Thr Lys Gly Tyr Asp Phe
            260             265             270
```

```
Asn Lys Gly Gln Trp Arg Asp Phe Val Leu Lys Gly His Lys His Thr
            275             280             285
```

```
Asn Arg Arg Ile Asp Tyr Ser Tyr Glu Ile Asn Pro Val Gly Thr Pro
    290             295             300
```

```
Gln Glu Cys Ile Asp Ile Ile Gln Thr Asp Ile Asp Ala Thr Gly Ile
305             310             315             320
```

```
Ser Asn Ile Cys Cys Gly Phe Glu Ala Asn Gly Thr Val Asp Glu Lys
            325             330             335
```

```
Ile Ala Ser Met Lys Leu Phe Gln Ser Asp Val Met Pro Phe Leu Lys
            340             345             350
```

```
Glu Thr Gln Arg Ser Leu Leu Met Ile Ala
            355             360
```

```
<210> SEQ ID NO 48
<211> LENGTH: 360
<212> TYPE: PRT
<213> ORGANISM: Artificial Sequence
<220> FEATURE:
<223> OTHER INFORMATION: reconstructed sequence

<400> SEQUENCE: 48
```

```
Met Lys Phe Gly Asn Phe Leu Leu Thr Tyr Gln Pro Pro Gln Phe Ser
1               5               10              15
```

```
Gln Thr Glu Val Met Lys Arg Leu Val Lys Leu Gly Arg Val Ser Glu
            20              25              30
```

```
Glu Cys Gly Phe Asp Thr Val Trp Leu Leu Glu His His Phe Thr Glu
            35              40              45
```

```
Phe Gly Leu Leu Gly Asn Pro Tyr Val Ala Ala Ala Tyr Leu Leu Gly
    50              55              60
```

```
Ala Thr Lys Lys Leu Asn Val Gly Thr Ala Ala Ile Val Leu Pro Thr
65              70              75              80
```

```
Ala His Pro Val Arg Gln Leu Glu Asp Val Asn Leu Leu Asp Gln Met
            85              90              95
```

```
Ser Lys Gly Arg Phe Arg Phe Gly Ile Cys Arg Gly Leu Tyr Asn Lys
            100             105             110
```

```
Asp Phe Arg Val Phe Gly Val Asp Met Asn Asn Thr Arg Ala Leu Met
            115             120             125
```

```
Glu Cys Trp Tyr Gly Leu Ile Lys Asn Gly Met Thr Glu Gly Tyr Val
    130             135             140
```

```
Glu Ala Asp Asn Glu His Ile Lys Phe His Lys Val Lys Val Asn Pro
145             150             155             160
```

```
Thr Ala Tyr Ser Lys Gly Gly Ala Pro Ile Tyr Val Val Ala Glu Ser
            165             170             175
```

```
Ala Ser Thr Thr Glu Trp Ala Ala Gln His Gly Leu Pro Met Ile Leu
            180             185             190
```

```
Ser Trp Ile Ile Asn Thr Asn Glu Lys Lys Ala Gln Leu Glu Leu Tyr
    195             200             205
```

-continued

```
Asn Glu Val Ala Gln Glu His Gly His Asp Val His Asn Ile Asp His
    210             215                 220

Cys Leu Ser Tyr Ile Thr Ser Val Asp His Asp Ser Ile Lys Ala Lys
225                 230                 235                 240

Glu Ile Cys Arg Asn Phe Leu Gly His Trp Tyr Asp Ser Tyr Val Asn
                245                 250                 255

Ala Thr Thr Ile Phe Asp Asp Ser Asp Lys Thr Lys Gly Tyr Asp Phe
                260                 265                 270

Asn Lys Gly Gln Trp Arg Asp Phe Val Leu Lys Gly His Lys Asp Thr
                275                 280                 285

Asn Arg Arg Ile Asp Tyr Ser Tyr Glu Ile Asn Pro Val Gly Thr Pro
    290                 295                 300

Glu Glu Cys Ile Asp Ile Ile Gln Lys Asp Ile Asp Ala Thr Gly Ile
305                 310                 315                 320

Ser Asn Ile Cys Cys Gly Phe Glu Ala Asn Gly Thr Val Asp Glu Ile
                325                 330                 335

Ile Ala Ser Met Lys Leu Phe Gln Ser Asp Val Met Pro Phe Leu Lys
                340                 345                 350

Glu Lys Gln Arg Ser Leu Leu Tyr
        355                 360
```

```
<210> SEQ ID NO 49
<211> LENGTH: 360
<212> TYPE: PRT
<213> ORGANISM: Artificial Sequence
<220> FEATURE:
<223> OTHER INFORMATION: reconstructed sequence

<400> SEQUENCE: 49

Met Lys Phe Gly Asn Phe Leu Leu Thr Tyr Gln Pro Pro Gln Phe Ser
1               5                   10                  15

Gln Ser Glu Val Met Gln Arg Leu Val Lys Leu Gly Arg Val Ser Glu
                20                  25                  30

Glu Cys Gly Phe Asp Thr Val Trp Leu Leu Glu His His Phe Thr Glu
            35                  40                  45

Phe Gly Leu Leu Gly Asn Pro Tyr Val Ala Ala Ala Asn Leu Leu Gly
    50                  55                  60

Ala Thr Lys Lys Leu Asn Val Gly Thr Ala Ala Ile Val Leu Pro Thr
65                  70                  75                  80

Ala His Pro Val Arg Gln Leu Glu Asp Val Asn Leu Leu Asp Gln Met
                85                  90                  95

Ser Lys Gly Arg Phe Arg Phe Gly Ile Cys Arg Gly Leu Tyr Asn Lys
                100                 105                 110

Asp Phe Arg Val Phe Gly Thr Asp Met Asp Asn Thr Arg Ala Leu Thr
                115                 120                 125

Glu Cys Trp Tyr Gly Ile Ile Lys Asn Gly Met Thr Glu Gly Tyr Met
    130                 135                 140

Glu Ala Asp Asn Glu His Ile Lys Phe His Lys Val Lys Val Asn Pro
145                 150                 155                 160

Thr Ala Tyr Ser Gln Gly Gly Ala Pro Ile Tyr Val Val Ala Glu Ser
                165                 170                 175

Ala Ser Thr Thr Glu Trp Ala Ala Gln His Gly Leu Pro Met Ile Leu
                180                 185                 190

Ser Trp Ile Ile Asn Asn Asn Glu Lys Ile Tyr Gln Ala Glu Leu Tyr
                195                 200                 205
```

-continued

```
Asn Glu Val Ala Leu Glu Tyr Gly His Asp Ile Thr Asn Ile Asp His
    210             215             220
```

```
Cys Leu Ser Tyr Ile Thr Ser Val Asp His Asp Ser Ile Lys Ala Lys
225             230             235             240
```

```
Glu Ile Cys Arg Asp Phe Leu Gly His Trp Tyr Asp Ser Tyr Val Asn
            245             250             255
```

```
Ala Thr Thr Ile Phe Asp Asp Ser Asp Gln Thr Lys Gly Tyr Gly Phe
            260             265             270
```

```
Asn Lys Gly Gln Trp Arg Asp Phe Val Leu Lys Gly His Lys Asp Thr
            275             280             285
```

```
Asn Arg Arg Ile Asp Tyr Ser Tyr Glu Ile Asn Pro Val Gly Thr Pro
    290             295             300
```

```
Gln Glu Cys Ile Asp Ile Ile Gln Thr Asp Ile Asp Ala Thr Gly Ile
305             310             315             320
```

```
Ser Asn Ile Cys Cys Gly Phe Lys Ala Asn Gly Thr Val Asp Glu Ile
            325             330             335
```

```
Ile Ala Ser Met Lys Leu Phe Gln Ser Asp Val Met Pro Phe Leu Lys
            340             345             350
```

```
Glu Lys Gln Arg Ser Leu Leu Tyr
        355             360
```

```
<210> SEQ ID NO 50
<211> LENGTH: 360
<212> TYPE: PRT
<213> ORGANISM: Artificial Sequence
<220> FEATURE:
<223> OTHER INFORMATION: reconstructed sequence

<400> SEQUENCE: 50
```

```
Met Lys Phe Gly Asn Phe Leu Leu Thr Tyr Gln Pro Pro Gln Phe Ser
1               5               10              15
```

```
Gln Thr Glu Val Met Gln Arg Leu Val Glu Leu Gly Arg Val Ser Glu
            20              25              30
```

```
Glu Cys Gly Phe Asp Thr Val Trp Leu Leu Glu His His Phe Thr Glu
        35              40              45
```

```
Phe Gly Leu Gly Gly Asn Val Gln Val Ala Ala Ala Phe Leu Leu Gly
    50              55              60
```

```
Ala Thr Lys Lys Leu Asn Val Gly Thr Ala Ala Ile Val Leu Pro Thr
65              70              75              80
```

```
Ala His Pro Val Arg Gln Leu Glu Asp Val Asn Leu Leu Asp Gln Met
            85              90              95
```

```
Ser Lys Gly Arg Phe Arg Phe Gly Ile Cys Arg Gly Leu Tyr Asn Lys
            100             105             110
```

```
Asp Phe Arg Val Phe Gly Val Asp Met Asn Asn Ser Arg Ala Leu Met
            115             120             125
```

```
Glu Lys Trp Tyr Glu Arg Ile Lys Arg Gly Ile Thr Glu Gly Tyr Met
    130             135             140
```

```
Glu Ala Asp Asn Glu His Ile Lys Phe His Lys Val Lys Val Asn Pro
145             150             155             160
```

```
Thr Ala Tyr Ser Gln Gly Gly Ala Pro Ile Tyr Val Val Ala Thr Ser
            165             170             175
```

```
Ala Ser Thr Thr Glu Trp Ala Ala Gln His Gly Leu Pro Met Ile Leu
            180             185             190
```

```
Ser Trp Ile Ile Asn Arg Asn Glu Lys Ile Ala Gln Ile Glu Leu Tyr
    195             200             205
```

```
Asn Glu Val Ala Gln Glu Ser Gly His Asp Ile His Asn Ile Asp His
    210             215             220
```

```
Cys Leu Ser Tyr Ile Thr Ser Val Asp His Asp Ser Ile Lys Ala Lys
225             230             235             240
```

```
Glu Ile Cys Arg Asn Phe Leu Gly His Trp Tyr Asp Ser Tyr Val Asn
            245             250             255
```

```
Ala Thr Thr Ile Phe Asp Asp Ser Asp Lys Thr Lys Gly Tyr Gly Phe
            260             265             270
```

```
Asn Lys Gly Gln Trp Ala Asp Phe Val Leu Lys Gly His Lys Asn Thr
            275             280             285
```

```
Asn Arg Arg Ile Asp Tyr Ser Tyr Glu Ile Asn Pro Val Gly Thr Pro
    290             295             300
```

```
Lys Glu Cys Ile Asp Ile Ile Gln Thr Asp Ile Asp Ala Thr Gly Ile
305             310             315             320
```

```
Ser Asn Ile Cys Cys Gly Phe Glu Ala Asn Gly Thr Val Asp Glu Ile
            325             330             335
```

```
Ile Ala Ser Met Lys Leu Phe Gln Lys Asp Val Met Pro Phe Leu Lys
            340             345             350
```

```
Glu Thr Gln Arg Ser Leu Leu Phe
    355             360
```

```
<210> SEQ ID NO 51
<211> LENGTH: 360
<212> TYPE: PRT
<213> ORGANISM: Artificial Sequence
<220> FEATURE:
<223> OTHER INFORMATION: reconstructed sequence
```

```
<400> SEQUENCE: 51
```

```
Met Lys Phe Gly Asn Phe Leu Leu Thr Tyr Gln Pro Pro Gln Phe Ser
1               5               10              15
```

```
Gln Gly Glu Val Met Lys Arg Leu Val Asn Leu Gly Arg Val Ser Glu
            20              25              30
```

```
Glu Cys Gly Phe Asp Thr Val Trp Leu Leu Glu His His Phe Thr Glu
        35              40              45
```

```
Phe Gly Leu Leu Gly Asn Pro Tyr Val Ala Ala Ala Tyr Leu Leu Gly
    50              55              60
```

```
Ala Thr Lys Lys Leu Asn Val Gly Thr Ala Ala Ile Val Leu Pro Thr
65              70              75              80
```

```
Ala His Pro Val Arg Gln Leu Glu Asp Val Asn Leu Leu Asp Gln Met
            85              90              95
```

```
Ser Lys Gly Arg Phe Arg Phe Gly Ile Cys Arg Gly Leu Tyr Asn Lys
            100             105             110
```

```
Asp Phe Arg Val Phe Gly Val Asp Met Asp Asn Thr Arg Ala Leu Met
            115             120             125
```

```
Glu Cys Trp Tyr Gly Leu Ile Lys Glu Gly Met Thr Glu Gly Tyr Val
    130             135             140
```

```
Glu Ala Asp Asn Glu His Ile Lys Phe His Lys Val Lys Val Asn Pro
145             150             155             160
```

```
Thr Ala Tyr Ser Lys Gly Gly Ala Pro Val Tyr Val Val Ala Glu Ser
            165             170             175
```

```
Ala Ser Thr Thr Glu Trp Ala Ala Gln His Gly Leu Pro Met Ile Leu
            180             185             190
```

```
Ser Trp Ile Ile Asn Thr Asn Glu Lys Lys Ala Gln Leu Asp Tyr Tyr
    195             200             205
```

```
Asn Glu Val Ala Gln Glu Tyr Gly His Asp Val His Asn Ile Asp His
    210             215             220
```

```
Cys Leu Ser Tyr Ile Thr Ser Val Asp His Asp Ser Ile Lys Ala Lys
225             230             235             240
```

```
Glu Ile Cys Arg Lys Phe Leu Gly His Trp Tyr Asp Ser Tyr Val Asn
            245             250             255
```

```
Ala Thr Thr Ile Phe Asp Asp Ser Asp Gln Thr Lys Gly Tyr Asp Phe
            260             265             270
```

```
Asn Lys Gly Gln Trp Arg Asp Phe Val Leu Lys Gly His Lys Asp Thr
            275             280             285
```

```
Asn Arg Arg Ile Asp Tyr Ser Tyr Glu Ile Asn Pro Val Gly Thr Pro
    290             295             300
```

```
Glu Glu Cys Ile Asp Ile Ile Gln Thr Asp Ile Asp Ala Thr Gly Ile
305             310             315             320
```

```
Ser Asn Ile Cys Cys Gly Phe Glu Ala Asn Gly Thr Val Asp Glu Ile
            325             330             335
```

```
Ile Ala Ser Met Lys Leu Phe Gln Ser Asp Val Met Pro Phe Leu Lys
            340             345             350
```

```
Glu Lys Gln Arg Ser Leu Leu Tyr
        355             360
```

```
<210> SEQ ID NO 52
<211> LENGTH: 360
<212> TYPE: PRT
<213> ORGANISM: Artificial Sequence
<220> FEATURE:
<223> OTHER INFORMATION: reconstructed sequence

<400> SEQUENCE: 52
```

```
Met Lys Phe Gly Asn Phe Leu Leu Thr Tyr Gln Pro Pro Gln Phe Ser
1               5               10              15
```

```
Gln Thr Glu Val Met Gln Arg Leu Val Lys Leu Gly Arg Val Ser Glu
            20              25              30
```

```
Glu Cys Gly Phe Asp Thr Val Trp Leu Leu Glu His His Phe Thr Glu
        35              40              45
```

```
Phe Gly Leu Leu Gly Asn Pro Tyr Val Ala Ala Ala Tyr Leu Leu Gly
    50              55              60
```

```
Ala Thr Lys Lys Leu Asn Val Gly Thr Ala Ala Ile Val Leu Pro Thr
65              70              75              80
```

```
Ala His Pro Val Arg Gln Leu Glu Asp Val Asn Leu Leu Asp Gln Met
            85              90              95
```

```
Ser Lys Gly Arg Phe Arg Phe Gly Ile Cys Arg Gly Leu Tyr Asn Lys
            100             105             110
```

```
Asp Phe Arg Val Phe Gly Thr Asp Met Asp Asn Ser Arg Ala Leu Met
            115             120             125
```

```
Glu Cys Trp Tyr Gly Leu Ile Lys Asn Gly Met Thr Glu Gly Tyr Val
    130             135             140
```

```
Glu Ala Asp Asn Glu His Ile Lys Phe His Lys Val Lys Val Asn Pro
145             150             155             160
```

```
Thr Ala Tyr Ser Gln Gly Gly Ala Pro Val Tyr Val Val Ala Glu Ser
            165             170             175
```

```
Ala Ser Thr Thr Glu Trp Ala Ala Gln His Gly Leu Pro Met Ile Leu
            180             185             190
```

```
Ser Trp Ile Ile Asn Thr Asn Glu Lys Lys Ala Gln Leu Glu Leu Tyr
    195             200             205
```

```
Asn Glu Val Ala Gln Glu Tyr Gly His Asp Ile His Asn Ile Asp His
    210             215             220

Cys Leu Ser Tyr Ile Thr Ser Val Asp His Asp Ser Ile Lys Ala Lys
225             230             235             240

Glu Ile Cys Arg Asn Phe Leu Gly His Trp Tyr Asp Ser Tyr Val Asn
            245             250             255

Ala Thr Thr Ile Phe Asp Asp Ser Asp Gln Thr Lys Gly Tyr Asp Phe
            260             265             270

Asn Lys Gly Gln Trp Arg Asp Phe Val Leu Lys Gly His Lys Asp Thr
        275             280             285

Asn Arg Arg Ile Asp Tyr Ser Tyr Glu Ile Asn Pro Val Gly Thr Pro
    290             295             300

Gln Glu Cys Ile Asp Ile Ile Gln Thr Asp Ile Asp Ala Thr Gly Ile
305             310             315             320

Ser Asn Ile Cys Cys Gly Phe Glu Ala Asn Gly Thr Val Asp Glu Ile
            325             330             335

Ile Ala Ser Met Lys Leu Phe Gln Ser Asp Val Met Pro Phe Leu Lys
            340             345             350

Glu Lys Gln Arg Ser Leu Leu Tyr
        355             360
```

```
<210> SEQ ID NO 53
<211> LENGTH: 1172
<212> TYPE: DNA
<213> ORGANISM: Artificial Sequence
<220> FEATURE:
<223> OTHER INFORMATION: reconstructed sequence

<400> SEQUENCE: 53
caattttcgt actgaaacat cttaatcatg cacaggagac tttctaatga aatttggaaa      60 cttttttgctt acataccaac ctccccaatt ttctcaaaca gaggtaatga aacgtttggt     120
taaattaggt cgcgtgtctg aggagtgtgg ttttgatacc gtatggttac tggagcatca     180
tttcacggag tttggtttgc ttggtaaccc ttatgtcgct gctgcatatt tacttggcgc     240
gactaaaaaa ttgaatgtag gaactgccgc tattgttctt cccacagccc atccagtacg     300
ccaacttgaa gatgtgaatt tattggatca aatgtcaaaa ggacgatttc ggtttggtat     360
ttgccgaggg ctttacaaca aggactttcg cgtattcggc gttgatatga ataacacacg     420
cgccttaatg gaatgctggt acgggctgat aaagaatggc atgacagagg gatatgtgga     480
agctgataat gaacatatca agttccataa ggtaaaagta aacccaccg cgtatagcca      540 gggtggcgca ccggtttatg tggtggctga atcagcttcg acgactgagt gggctgctca     600
acatggccta ccgatgatat taagttggat tataaatact aacgaaaaga aagcacaact     660
tgagctttat aatgaagtgg ctcaagaata tgggcacgat gttcataata tcgaccattg     720
cttatcatat ataacatctg tagatcatga ctcaattaaa gcgaaagaga tttgccggaa     780
ctttctgggg cattggtatg attcttatgt gaatgctacg actatttttg atgattcaga     840
ccaaacaaaa ggttatgatt tcaataaagg gcagtggcgt gactttgtat taaaaggaca     900
taaagatact aatcgccgta ttgattacag ttacgaaatc aatcccgtgg gaacgccgaa     960
ggaatgtatt gacataattc aaaccgacat tgatgctaca ggaatatcaa atatttgttg    1020
tggatttgaa gctaatggaa cagtagacga aattattgct tccatgaagc tcttccagtc    1080
```

```
tgatgtcatg ccatttctta aagaaaaaca acgttcgcta ttatattgag gatcggttgt      1140
cgagtaagga tctccaggca tcaaataaaa cg                                     1172
```

```
<210> SEQ ID NO 54
<211> LENGTH: 1169
<212> TYPE: DNA
<213> ORGANISM: Artificial Sequence
<220> FEATURE:
<223> OTHER INFORMATION: reconstructed sequence

<400> SEQUENCE: 54
caattttcgt actgaaacat cttaatcatg cacaggagac tttctaatga aatttggaaa        60 cttttttgctt acataccaac ctccccaatt ttctcaaaca gaggtaatgc aacgtttggt      120
taacttaggt cgcgcctctg aggagtgtgg ttttgatacc gtatggttac tggagcatca      180
tttcacggag tttggtttgc ttggtaaccc ttatgtcgct gctgcatatt tacttggcgc      240
gactaaacac ttgaatgtag gaactgccgc tattgttctt cccacagccc atccagtacg      300
ccaacttgaa gatgtgaatt tattggatca aatgtcaaaa ggacgatttc ggtttggtat      360
ttgccgaggg ctttacaaca aggactttaa tgtattcggc gttgatatga ataacacacg      420
cgccttaact gaatgctggt acgggctgat aaagaatggc atgacagagg gatatatgga      480
agctgataat gaacatatca agttccataa ggtaaaagta aacccaccg cgtatagcaa       540 gggtggcgca ccggtttatg tggtggctga atcagcttcg acgactgagt gggctgctca      600
acatggccta ccgatgatat taagttggat tataaatact aacgaaaaga aagcacaaat      660
tgatctttat aatgaagtgg ctcaagaaca cgggcacgat gttcataata tcgaccattg      720
cttatcatat ataacatctg tagatcatga ctcaaagaaa gcgaaagaga tttgccggga      780
ttttctgggg cattggtatg attcttatgt gaatgctacg actattttg atgattcaga       840 ccaaacaaaa ggttatggct tcaataaagg gcagtggcat gactttgtat taaaaggaca      900
taaagatact aatcgccgtg ttgattacag ttacgaaatc aatcccgtgg aacgccgca      960 ggaatgtatt gacataaattc aaaccgacat tgatgctaca ggaatatcaa atatttgttg     1020
tggatttgaa gctaatggaa cagtagacga aattattgct tccatgaagc tcttccagtc     1080
tgatgtcatg ccatttctta aagaaaaaca acgttcgcta ttatgaggat cggttgtcga     1140
gtaaggatct ccaggcatca ataaaacg                                        1169
```

```
<210> SEQ ID NO 55
<211> LENGTH: 1169
<212> TYPE: DNA
<213> ORGANISM: Artificial Sequence
<220> FEATURE:
<223> OTHER INFORMATION: reconstructed sequence

<400> SEQUENCE: 55
caattttcgt actgaaacat cttaatcatg cacaggagac tttctaatga aatttggaaa        60 cttttttgctt acataccaac ctccccaatt ttctcaaaca gaggtaatgc aacgtttggt      120
taaattaggt cgcgtgtctg aggagtgtgg ttttgatacc gtatggttac tggagcatca      180
tttcacggag tttggtttgc ttggtaaccc ttatgtcgct gctgcatatt tacttggcgc      240
gactaaaaaa ttgaatgtag gaactgccgc tattgttctt cccacagccc atccagtacg      300
ccaacttgaa gatgtgaatt tattggatca aatgtcaaaa ggacgatttc ggtttggtat      360
ttgccgaggg ctttacaaca aggactttcg cgtattcggc gttgatatga ataacacacg      420
```

-continued

```
cgccttaatg gaatgctggt acgggctgat aaagaatggc atgacagagg gatatatgga        480
agctgataat gaacatatca agttccataa ggtaaaagta aaccccaccg cgtatacaca        540
gggtggcgca ccgatttatg tggtggctga atcagcttcg acgactgagt gggctgctca        600
atttggccta ccgatgatat taagttggat tataaatact aacgaaaaga tcgcacaact        660
tgagctttat aatgaagtgg ctcaagaata tgggcacgat gttcataata tcgaccattg        720
cttatcatat ataacatctg tagatcatga ctcaattaaa gcgaaagaga tttgccggca        780
atttctgggg cattggtatg attcttatgt gaatgctacg actatttttg atgattcaga        840
ccaaacaaaa ggttatgatt tcaataaagg gcagtggcgt gactttgtat aaaaaggaca        900
taaagatact aatcgccgta ttgattacag ttacgaaatc aatcccgtgg gaacgccgaa        960
ggaatgtatt gacataattc aaaccgacat tgatgctaca ggaatatcaa atatttgttg       1020
tggatttgaa gctaatggaa cagtagacga aattattgct tccatgaagc tcttccagtc       1080
tgatgtcatg ccatttctta aagaaaaaca acgttcgcta ttatgaggat cggttgtcga       1140
gtaaggatct ccaggcatca aataaaacg                                          1169
```

```
<210> SEQ ID NO 56
<211> LENGTH: 1169
<212> TYPE: DNA
<213> ORGANISM: Artificial Sequence
<220> FEATURE:
<223> OTHER INFORMATION: reconstructed sequence

<400> SEQUENCE: 56
```

```
caattttcgt actgaaacat cttaatcatg cacaggagac tttctaatga aatttggaaa         60 cttttttgctt acataccaac ctccccaatt ttctcaaaca gaggtaatgc aacgtttggt        120
taaattaggt cgcgtgtctg aggagtgtgg ttttgatacc gtatggttac tggagcatca        180
tttcacggag tttggtttgc ttggtaaccc ttatgtcgct gctgcatatt tacttggcgc        240
gactaaaaaa ttgaatgtag gaactgccgc tattgttctt cccacagccc atccagtacg        300
ccaacttgaa gatgtgaatt tattggatca aatgtcaaaa ggacgatttc ggtttggtat        360
ttgccgaggg ctttacaaca aggactttcg cgtattcggc gttgatatga ataacacacg        420
cgccttaatg gaatgctggt acgggctgat aaagaatggc atgacagagg gatatgtgga        480
agctgataat gaacatatca agttccataa ggtaaaagta aaccccaccg cgtatagcca        540
gggtggcgca ccggtttatg tggtggctga atcagcttcg acgactgagt gggctgctca        600
acatggccta ccgatgatat taagttggat tataaatact aacgaaaaga tcgcacaaat        660
tgagctttat aatgaagtgg ctcaagaata tgggcacgat attcataata tcgaccattg        720
cttatcatat ataacatctg tagatcatga ctcaattaaa gcgaaagaga tttgccggaa        780
ctttctgggg cattggtatg attcttatgt gaatgctacg actatttttg atgattcaga        840
caagacaaaa ggttatggct tcaataaagg gcagtggcgt gactttgtat aaaaaggaca        900
taaagatact aatcgccgta ttgattacag ttacgaaatc aatcccgtgg gaacgccgaa        960
ggaatgtatt gacataattc aaaccgacat tgatgctaca ggaatatcaa atatttgttg       1020
tggatttgaa gctaatggaa cagtagacga aattattgct tccatgaagc tcttccagtc       1080
tgatgtcatg ccatttctta aagaaacgca acgttcgcta ttatgaggat cggttgtcga       1140
gtaaggatct ccaggcatca aataaaacg                                          1169
```

```
<210> SEQ ID NO 57
<211> LENGTH: 1172
```

-continued

```
<212> TYPE: DNA
<213> ORGANISM: Artificial Sequence
<220> FEATURE:
<223> OTHER INFORMATION: reconstructed sequence

<400> SEQUENCE: 57
caattttcgt actgaaacat cttaatcatg cacaggagac tttctaatga aatttggaaa      60 cttttttgctt acataccaac ctccccaact ggaccaatcc gaggtaatgg cgcgtttggt     120
taaattaggt cgcgtgtctg aggagtgtgg ttttgatacc gtatggttac tggagcatca     180
tttcacggag tttggtttgc ttggtaaccc ttatgtcgct gctgcatatt tacttggcgc     240
gactaaaaaa ttgaatgtag gaactgccgc tattgttctt cccacagccc atccagtacg     300
ccaacttgaa gatgtgaatt tattggatca aatgtcaaaa ggacgatttc ggtttggtat     360
ttgccgaggg ctttacaaca aggactttcg cgtattcggc gttgatatga ataacagtcg     420
cgccttaatg gaatgctggt acgacctgat aaaggaaggc atgacagagg gatatgtgga     480
agctgatacg gaacatatca agttccataa ggtaaaacat ttgcccaccg cgtatagcca     540
gggtggcgca ccggtttatg tggtggctga atcagcttcg acgactgagt gggctgctca     600
acatggccta ccgatgatat taagttggat tataaaatact aacgaaaaga aagcacaact     660
tgagctttat aatgaagtgg ctcaagaata tgggcacgat attcataata tcgaccattg     720
cttatcatat ataacatctg tagatcatga ctcaattcgt gcgaaagaga aatgcgtcaa     780
ccatctgggg cattggtatg attcttatgt gaatgctacg actattttttg atgattcaga     840 ccaaacaaaa ggttatggct tcaataaagg gcagtggcgt gactttgtat taaaaggaca     900
taaagatact aatcgccgta ttgattacag ttacgaaatc aatcccgtgg gaacgccgaa     960
cgaatgtatt gacataaattc aaaccgacat tgatgctaca ggaatatcaa atatttgttg    1020
tggatttgaa gctaatggaa cagtagacga acgtattgct tccatgttgc tcttccagtc    1080
tgatgtcatg ccatttctta agaaaaaaca acgttcgcta ttatattgag gatcggttgt    1140
cgagtaagga tctccaggca tcaaataaaa cg                                   1172

<210> SEQ ID NO 58
<211> LENGTH: 1172
<212> TYPE: DNA
<213> ORGANISM: Artificial Sequence
<220> FEATURE:
<223> OTHER INFORMATION: reconstructed sequence

<400> SEQUENCE: 58
caattttcgt actgaaacat cttaatcatg cacaggagac tttctaatga aatttggaaa      60 cttttttgctt acataccaac ctccccaatt ttctcaaaca gaggtaatgc aacgtttggt     120
taaattaggt cgcgtgtctg aggagtgtgg ttttgatacc gtatggttac tggagcatca     180
tttcacggag tttggtttgc ttggtaaccc ttatgtcgct gctgcatatt tacttggcgc     240
gactaaaaaa ttgaatgtag gaactgccgc tattgttctt cccacagccc atccagtacg     300
ccaacttgaa gatgtgaatt tattggatca aatgtcaaaa ggacgatttc ggtttggtat     360
ttgccgaggg ctttacaaca aggactttcg cgtattcggc gttgatatga ataacacacg     420
cgccttaatg gaatgctggt acgggctgat aaagaatggc atgacagagg gatatgtgga     480
agctgataat gaacatatca agttccataa ggtaaaagta aaccccaccg cgtatagcca     540
gggtggcgca ccggtttatg tggtggctga atcagcttcg acgactgagt gggctgctca     600
atttggccta ccgatgatat taagttggat tataaaatact aacgaaaaga aagcacaact     660
```

```
tgagctttat aatgaagtgg ctcaagaata tgggcacgat attcataata tcgaccattg      720
cttatcatat ataacatctg tagatcatga ctcaattaaa gcgaaagaga tttgccggaa      780
ctttctgggg cattggtatg attcttatgt gaatgctacg actattttg atgattcaga       840 ccaaacaaaa ggttatggct tcaataaagg gcagtggcgt gactttgtat taaaaggaca      900
taaaaatact aatcgccgta ttgattacag ttacgaaatc aatcccgtgg gaacgccgaa      960
ggaatgtatt gacataattc aaaccgacat tgatgctaca ggaatatcaa atatttgttg     1020
tggatttgaa gctaatggaa cagtagacga aattattgct tccatgaagc tcttccagtc     1080
tgatgtcatg ccatttctta agaaaaaca acgttcgcta ttatattgag gatcggttgt      1140
cgagtaagga tctccaggca tcaaataaaa cg                                    1172
```

<210> SEQ ID NO 59
<211> LENGTH: 1169
<212> TYPE: DNA
<213> ORGANISM: Artificial Sequence
<220> FEATURE:
<223> OTHER INFORMATION: reconstructed sequence

<400> SEQUENCE: 59

```
caattttcgt actgaaacat cttaatcatg cacaggagac tttctaatga aatttggaaa       60 cttttttgctt acataccaac ctccccaatt ttctcaaaca gaggtaatga aacgtttggt      120
taaattaggt cgcgtgtctg aggagtgtgg ttttgatacc gtatggttac tggagcatca      180
tttcacggag tttggtttgc ttggtaaccc ttatgtcgct gctgcatatt tacttggcgc      240
gactaaaaaa ttgaatgtag gaactgccgc tattgttctt cccacagccc atccagtacg      300
ccaacttgaa gatgtgaatt tattggatca aatgtcaaaa ggacgatttc ggtttggtat      360
ttgccgaggg ctttacaaca aggactttcg cgtattcggc gttgatatgg ataacacacg      420
cgccttaatg gaatgctggt acgggctgat aaagaatggc atgacagagg gatatgtgga      480
agctgataat gaacatatca agttccataa ggtaaaagta aaccccaccg cgtatagcca      540
gggtggcgca ccgatttatg tggtggctga atcagcttcg acgactgagt gggctgctca      600
acatggccta ccgatgatat taagttggat tataaatact aacgaaaaga aagcacaact      660
tgagctttat aatgaagtgg ctcaagaaca cgggcacgat gttcataata tcgaccattg      720
cttatcatat ataacatctg tagatcatga ctcaattaaa gcgaaagaga tttgccggaa      780
ctttctgggg cattggtatg attcttatgt gaatgctacg actattttg atgattcaga       840 ccaaacaaaa ggttatggct tcaataaagg gcagtggcgt gactttgtat taaaaggaca      900
taaagatact aatcgccgta ttgattacag ttacgaaatc aatcccgtgg gaacgccgaa      960
ggaatgtatt gacataattc aaaccgacat tgatgctaca ggaatatcaa atatttgttg     1020
tggatttgaa gctaatggaa cagtagacga aattattgct tccatgaagc tcttccagtc     1080
tgatgtcatg ccatttctta agaaaaaca acgttcgcta ttatgaggat cggttgtcga      1140
gtaaggatct ccaggcatca aataaaacg                                        1169
```

<210> SEQ ID NO 60
<211> LENGTH: 1172
<212> TYPE: DNA
<213> ORGANISM: Artificial Sequence
<220> FEATURE:
<223> OTHER INFORMATION: reconstructed sequence -continued

<400> SEQUENCE: 60
caattttcgt actgaaacat cttaatcatg cacaggagac tttctaatga aatttggaaa      60
ctttttgctt acataccaac ctccccaatt ttctcaaaca gaggtaatgc aacgtttggt     120
taaattaggt cgcgtgtctg aggagtgtgg ttttgatacc gtatggttac tggagcatca     180
tttcacggag tttggtttgc ttggtaaccc ttatgtcgct gctgcatatt tacttggcgc     240
gactaaaaaa ttgaatgtag gaactgccgc tattgttctt cccacagccc atccagtacg     300
ccaacttgaa gatgtgaatt tattggatca aatgtcaaaa ggacgatttc ggtttggtat     360
ttgccgaggg ctttacaaca aggactttcg cgtattcggc gttgatatga ataacacacg     420
cgccttaatg gaatgctggt acgggctgat aaagaatggc atgacagagg gatatatgga     480
agctgataat gaacatatca agttccataa ggtaaaagta aaccccaccg cgtatagcca     540
gggtggcgca ccggtttatg tggtggctga atcagcttcg acgactgagt gggctgctca     600
acatggccta ccgatgatat taagttggat tataaatact aacgaaaaga aagcacaact     660
tgagctttat aatgaagtgg ctcaagaaca cgggcacgat attcataata tcgaccattg     720
cttatcatat ataacatctg tagatcatga ctcaattaaa gcgaaagaga tttgccggaa     780
ctttctgggg cattggtatg attcttatgt gaatgctacg actatttttg atgattcaga     840
ccaaacaaaa ggttatgatt tcaataaagg gcagtggcgt gactttgtat taaaaggaca     900
taaagatact aatcgccgta ttgattacag ttacgaaatc aatcccgtgg gaacgccgaa     960
ggaatgtatt gacataattc aaaccgacat tgatgctaca ggaatatcaa atatttgttg    1020
tggatttgaa gctaatggaa cagtagacga aattattgct tccatgaagc tcttccagtc    1080
tgatgtcatg ccatttctta agaaaaaaca acgttcgcta ttatattgag gatcggttgt    1140
cgagtaagga tctccaggca tcaaataaaa cg                                   1172

<210> SEQ ID NO 61
<211> LENGTH: 1172
<212> TYPE: DNA
<213> ORGANISM: Artificial Sequence
<220> FEATURE:
<223> OTHER INFORMATION: reconstructed sequence

<400> SEQUENCE: 61
caattttcgt actgaaacat cttaatcatg cacaggagac tttctaatga aatttggaaa      60
ctttttgctt acataccaac ctccccaact gccgcaaaca gaggtaatga aacgtttggt     120
taaattaggt cgcgtgtctg agggttgtgg ttttgatacc gtatggttac tggagcatca     180
tttcacggag tttggtttgc ttggtaaccc ttatgtcgct gctgcacatt tacttggcgc     240
gactaaaaaa ttgaatgtag gaactgccgc tattgttctt cccacagccc atccaattcg     300
ccaacttgaa gatgtgaatt tattggatca aatgtcaaaa ggacgatttc ggtttggtat     360
ttgccgaggg ctttacaaca aggactttcg cgtattcggc acagatatga ataacagtcg     420
cgtgttaatg gaatgctggt acgggctgat aaagaatggc atgacagagg gatatatgga     480
agctgataat gaacatatca agttccataa ggtaaaagta aaccccaccg cgtatagcag     540
aggtggcgca ccggtttatg tggtggctga atcagcttcg acgactgagt gggctgctca     600
atttggccta ccgatgatat taagttggat tataaatact aacgaaaaga aagcacaagc     660
tgagctttat aatgaagtgg ctctcgaata tgggcgtgat attcataata tcgaccattg     720
cttatcatat ataacatctg tagatcatga ctcaattaaa gcgaaagaga tttgccggaa     780

```
ctttctgggg cattggtatg attcttatgt gaatgctacg actatttttg atgattcaga      840
ccaaacaaaa ggttatgatt tcaataaagg gcagtggcgt gactttgtat taaaaggaca      900
taaagatact aatcgccgta ttgattacag ttacgaaatc aatcccgtgg gaacgccgga      960
agaatgtatt gacataattc aaaccgacat tgatgctaca ggaatatcaa atatttgttg     1020
tggatttgaa gctaatggaa cagtagacga aattattgct tccatgaagc tcttccagtc     1080
tgatgtcatg ccatttctta aagaaaaaca acgttcgcta ttatattgag gatcggttgt     1140
cgagtaagga tctccaggca tcaaataaaa cg                                    1172
```

<210> SEQ ID NO 62
<211> LENGTH: 1172
<212> TYPE: DNA
<213> ORGANISM: Artificial Sequence
<220> FEATURE:
<223> OTHER INFORMATION: reconstructed sequence

<400> SEQUENCE: 62

```
caattttcgt actgaaacat cttaatcatg cacaggagac tttctaatga aatttggaaa       60 cttttttgctt acataccaac ctccccaatt ttctcaaaca gaggtaatga aacgtttggt      120
taaattaggt cgcgtgtctg aggagtgtgg ttttgatacc gtatggttac tggagcatca      180
tttcacggag tttggtttgc ttggtaaccc ttatgtcgct gctgcatatt tacttggcgc      240
gactaaaaaa ttgaatgtag gaactgccgc tattgttctt cccacagccc atccagtacg      300
ccaacttgaa gatgtgaatt tattggatca aatgtcaaaa ggacgatttc ggtttggtat      360
ttgccgaggg ctttacaaca aggactttcg cgtattcggc gttgatatga ataacagtcg      420
cgccttaatg gaatgctggt acgggctgat aaagaatggc atgacagagg gatatgtgga      480
agctgataat gaacatatca agttccataa ggtaaaagta aacccaccg cgtatagcca       540 gggtggcgca ccgatttatg tggtggctga atcagcttcg acgactgagt gggctgctca      600
acatggccta ccgatgatat taagttggat tataaatact aacgaaaaga aagcacaact      660
tgagttttat aatgaagtgg ctcaagaata tgggcacgat attcataata tcgaccattg      720
cttatcatat ataacatctg tagatcatga ctcaattaaa gcgaaagaga tttgccggaa      780
ctttctgggg cattggtatg attcttatgt gaatgctacg actatttttg atgattcaga      840
ccaaacaaaa ggttatggct tcaataaagg gcagtggcgt gactttgtat taaaaggaca      900
taaaaatact aatcgccgta ttgattacag ttacgaaatc aatcccgtgg gaacgccgaa      960
ggaatgtatt gacataattc aaaccgacat tgatgctaca ggaatatcaa atatttgttg     1020
tggatttgaa gctaatggaa cagtagacga aattattgct tccatgaagc tcttccagtc     1080
tgatgtcatg ccatttctta aagaaaaaca acgttcgcta ttatattgag gatcggttgt     1140
cgagtaagga tctccaggca tcaaataaaa cg                                    1172
```

<210> SEQ ID NO 63
<211> LENGTH: 1172
<212> TYPE: DNA
<213> ORGANISM: Artificial Sequence
<220> FEATURE:
<223> OTHER INFORMATION: reconstructed sequence

<400> SEQUENCE: 63

```
caattttcgt actgaaacat cttaatcatg cacaggagac tttctaatga aatttggaaa       60 cttttttgctt acataccaac ctcccgaatt ttctcaaaca gaggtaatga aacgtttggt      120
taaattaggt cgcgtgtctg aggagtgtgg ttttgatgaa gtatggttac tggagcatca      180
```

```
tttcacggag tttggtttgc ttggtaaccc ttatgtcgct gctgcacatt tacttggcgc      240
gactaaaaaa ttgaatgtag gaactgccgc tattgttctt cccacagccc atccagtacg      300
ccaacttgaa gatgtgaatt tattggatca aatgtcaaaa ggacgatttc ggtttggtat      360
ttgccgaggg ctttacaaca aggactttcg cgtattcggc gttgatatga ataacagtcg      420
cgtgttaatg gaatgctggt acgggctgat gaagaatggc atgacagagg gatatatgga      480
agctgataat gaacatatca agttccataa ggtaaaagta aaccccaccg cgtatacaca      540
gggtggcgca ccgatttatg tggtggctga atcagcttcg acgactgagt gggctgctca      600
acatggccta ccgatgatat taagttggat tataaataat aacgaaaaga tctatcaagc      660
taaattttat aatgaagtgg ctcaagaatc cgggcacgat attcataata tcgaccattg      720
cttatcatat ataacatctg tagatcatga ctcaattaaa gcgaaagaga tttgccggaa      780
ctttctgggg cattggtatg attcttatgt gaatgctacg actatttttg atgattcaga      840
caagacaaaa ggttatgatt tcaataaagg gcagtggcgt gactttgtat taaaaggaca      900
taaagatact aatcgccgta ttgattacag ttacgaaatc aatcccgtgg gaacgccgaa      960
ggaatgtatt gacataattc aaaccgacat tgatgctaca ggaatatcaa taaactgttg     1020
tggatttgaa gctaatggaa cagtagacga aattattgct tccatgaagc tcttccagtc     1080
tgatgtcatg ccatttctta agaaaaaaca acgttcgcta ttatattgag gatcggttgt     1140
cgagtaagga tctccaggca tcaaataaaa cg                                    1172
```

```
<210> SEQ ID NO 64
<211> LENGTH: 1172
<212> TYPE: DNA
<213> ORGANISM: Artificial Sequence
<220> FEATURE:
<223> OTHER INFORMATION: reconstructed sequence

<400> SEQUENCE: 64
```

```
caattttcgt actgaaacat cttaatcatg cacaggagac tttctaatga aatttggaaa       60 cttttttgctt acataccaac ctccccaatt ttctcaaaca gaggtaatga aacgtttggt      120
taaattaggt cgcgtgtctg aggagtgtgg ttttgatacc gtatggttac tggagcatca      180
tttcacggag tttggtttgc ttggtaaccc ttatgtcgct gctgcatatt tacttggcgc      240
gactaaaaaa ttgaatgtag gaactgccgc tattgttctt cccacagccc atccagtacg      300
ccaacttgaa gatgtgaatt tattggatca aatgtcaaaa ggacgatttc ggtttggtat      360
ttgccgaggg ctttacaaca aggactttcg cgtattcggc gttgatatga ataacacacg      420
cgccttaatg gaatgctggt acgggctgat aaagaatggc atgacagagg gatatatgga      480
agctgataat gaacatatca agttccataa ggtaaaagta aaccccaccg cgtatagcaa      540
gggtggcgca ccgatttatg tggtggctga atcagcttcg acgactgagt gggctgctca      600
atttggccta ccgatgatat taagttggat tataaatact aacgaaaaga agcacaact      660 tgagctttat aatgaagtgg ctcgtgaata tgggcacgat attcataata tcgaccattg      720
cttatcatat ataacatctg tagatcatga ctcaattaaa gcgaaagaga tttgccggca      780
atttctgggg cattggtatg attcttatgt gaatgctacg actatttttg atgattcaga      840
ccaaacaaaa ggttatggcc acaataaagg gcagtggcgt gactttgtat taaaaggaca      900
taaagatact aatcgccgta ttgattacag ttacgaaatc aatccccttg gaacgccgaa      960
ggaatgtatt gacataattc aaaccgacat tgatgctaca ggaatatcaa atatttgttg     1020
```

```
tggatttgaa gctaatggaa cagtagacga aattattgct tccatgaagc tcttccagtc      1080
tgatgtcatg ccatttctta aagaaacgca acgttcgcta ttatattgag gatcggttgt      1140
cgagtaagga tctccaggca tcaaataaaa cg                                    1172
```

```
<210> SEQ ID NO 65
<211> LENGTH: 1172
<212> TYPE: DNA
<213> ORGANISM: Artificial Sequence
<220> FEATURE:
<223> OTHER INFORMATION: reconstructed sequence

<400> SEQUENCE: 65
caattttcgt actgaaacat cttaatcatg cacaggagac tttctaatga aatttggaaa        60
ctttttgctt acataccaac ctccccaatt tccgcaaaca gaggtaatgc aacgtttggt       120
taaattaggt cgcgtgtctg aggagtgtgg ttttgatacc gtatggttac tggagcatca      180
tttcacggag tttggtttgc ttggtaaccc ttatgtcgct gctgcatatt tacttggcgc      240
gactaaaaaa ttgaatgtag gaactgccgt cattgttctt cccacagccc atccagtacg      300
ccaacttgaa gatgtgaatt tattggatca aatgtcaaaa ggacgatttc ggtttggtat      360
ttgccgaggg ctttacaaca aggactttcg cgtattcggc gttgatatga ataacacacg      420
cgccttaatg gaatgctggt acgggctgat aaagcgtggc atgacagagg atatgtggga      480
agctgataat gaacatatca agttccataa ggtaaaagta aacccaccg cgtatagcca       540 gggtggcgca ccgatttatg tggtggctga atcagcttcg acgactgagt gggctgctca      600
acatggccta ccgatgatat taagttggat tataaatact aacgaaaaga aagcacaact      660
tgagctttat aatgaagtgg ctcaagaaca cgggcacgat attcataata tcgaccattg      720
cttatcatat ataacatctg tagatcatga ctcaattaaa gcgaaagaga tttgccggca      780
atttctgggg cattggtatg attcttatgt gaatgctacg actattttg atgattcaga       840 ccaaacaaaa ggttatggct tcaataaagg gcagtggcgt gactttgtat taaaaggaca      900
taaagatact aatcgccgta ttgattacag ttacgaaatc aatcccgtgg aacgccgaa       960 ggaatgtatt gacataattc aaaccgacat tgatgctaca ggaatatcaa atatttgttg     1020
tggatttgaa gctaatggaa cagtaaatga aattattgct tccatgaagc tcttccagtc     1080
tgatgtcatg ccatttctta aagaaaaaca acgttcgcta ttatattgag gatcggttgt     1140
cgagtaagga tctccaggca tcaaataaaa cg                                   1172
```

```
<210> SEQ ID NO 66
<211> LENGTH: 1172
<212> TYPE: DNA
<213> ORGANISM: Artificial Sequence
<220> FEATURE:
<223> OTHER INFORMATION: reconstructed sequence

<400> SEQUENCE: 66
caattttcgt actgaaacat cttaatcatg cacaggagac tttctaatga aatttggaaa        60
ctttttgctt acataccaac ctccccaatt ttctcaaaca gaggtaatga aacgtttggt       120
taaattaggt cgcgtgtctg aggagtgtgg ttttgatacc gtatggttac tggagcatca      180
tttcacggag tttggtttgc ttggtaaccc ttatgtcgct gctgcatatt tacttggcgc      240
gactaaaaaa ttgaatgtag gaactgccgc tattgttctt cccacagccc atccagtacg      300
ccaacttgaa gatgtgaatt tattggatca aatgtcaaaa ggacgatttc ggtttggtat      360
ttgccgaggg ctttacaaca aggactttcg cgtattcggc gttgatatga ataacacacg      420
```

```
cgccttaatg gaatgctggt acgggctgat aaagaatggc atgacagagg gatatatgga        480
agctgataat gaacatatca agttccataa ggtaaaagta aaccccaccg cgtatagcca        540
gggtggcgca ccgatttatg tggtggctga atcagcttcg acgactgagt gggctgctca        600
atttggccta ccgatgatat taagttggat tataaaatact aacgaaaaga aagcacaact       660
tgagctttat aatgaagtgg ctcaagaata tgggcacgat attcataata tcgaccattg        720
cttatcatat ataacatctg tagatcatga ctcaattaaa gcgaaagaga tttgccggaa        780
ctttctgggg cattggtatg attcttatgt gaatgctacg actatttttg atgattcaga        840
ccaaacaaaa ggttatgatt tcaataaagg gcagtggcgt gactttgtat taaaaggaca        900
taaagatact aatcgccgta ttgattacag ttacgaaatc aatcccgtgg aacgccgca         960 ggaatgtatt gacataattc aaaccgacat tgatgctaca ggaatatcaa atatttgttg       1020
tggatttgaa gctaatggaa cagtagacga aattattgct tccatgaagc tcttccagtc      1080
tgatgtcatg ccatttctta aagaaaaaca acgttcgcta ttatattgag gatcggttgt      1140
cgagtaagga tctccaggca tcaaataaaa cg                                     1172
```

<210> SEQ ID NO 67
<211> LENGTH: 1172
<212> TYPE: DNA
<213> ORGANISM: Artificial Sequence
<220> FEATURE:
<223> OTHER INFORMATION: reconstructed sequence

<400> SEQUENCE: 67

```
caattttcgt actgaaacat cttaatcatg cacaggagac tttctaatga aatttggaaa         60 cttttttgctt acataccaac ctcccccaatt ttctcaaaca gaggtaatga aacgtttggt       120
taaattaggt cgcgtgtctg aggagtgtgg ttttgatacc gtatggttac tggagcatca        180
tttcacggag tttggtttgc ttggtaaccc ttatgtcgct gctgcaaatt tacttggcgc        240
gactaaaaaa ttgaatgtag gaactgccgc tattgttctt cccacagccc atccagtacg        300
ccaacttgaa gatgtgaatt tattggatca aatgtcaaaa ggacgatttc ggtttggtat        360
ttgccgaggg ctttacaaca aggactttcg cgtattcggc tatgatatgg ataacacacg        420
cgccttaatg gaatgctggt acgggctgat aaagaatggc atgacagagg gatatatgga        480
agctgataat gaacatatca agttccccaa ggtacatgta aaccccaccg cgtatacaca        540
gggtggcgca ccgatttatg tggtggctga atcagcttcg acgactgagt gggctgctca        600
atttggccta ccgatgatat taagttggat tgtgaataaa aacgaaaaga tcgcacaact        660
tgatctttat aatgaagtgg ctcaagaaca cgggcacgat gttcataata tcgaccattg        720
cttatcatat ataacatctg tagatcatga ctcagttaaa gcgaaagagg tctgcgaaaa       780
ctttctgggg cattggtatg attcttatgt gaatgctacg actatttttg atgattcaga        840
ccaaacaaaa ggttatggct tcaataaagg gcagtggcgt gactttgtat taaaaggaca        900
taaagatact aatcgccgta ttgattacag ttacgaaatc aatcccgtgg aacgccgaa         960 ggaatgtatt gacataattc aaaccgacat tgatgctaca ggaatatcaa atatttgttg       1020
tggatttgaa gctaatggaa cagtagacga aattattgct tccatgaagc tcttccagtc      1080
tgatgtcatg ccatttctta aagaaaaaca acgttcgcta ttaatgtgag gatcggttgt      1140
cgagtaagga tctccaggca tcaaataaaa cg                                     1172
```

<210> SEQ ID NO 68

129

130

-continued

```
<211> LENGTH: 1172
<212> TYPE: DNA
<213> ORGANISM: Artificial Sequence
<220> FEATURE:
<223> OTHER INFORMATION: reconstructed sequence

<400> SEQUENCE: 68
caattttcgt actgaaacat cttaatcatg cacaggagac tttctaatga aatttggaaa      60 cttttttgctt acataccaac ctccccaatt ttctcaaaca gaggtaatga aacgtttggt     120
taaattaggt cgcgtgtctg aggagtgtgg ttttgatacc gtatggttac tggagcatca     180
tttcacggag tttggtttgc ttggtaaccc ttatgtcgct gctgcaaatt tacttggcgc     240
gactaaaaaa ttgaatgtag gaactgccgc tattgttctt cccacagccc atccagtacg     300
ccaacttgaa gatgtgaatt tattggatca aatgtcaaaa ggacgatttc ggtttggtat     360
ttgccgaggg ctttacaaca aggactttcg cgtattcggc gttgatatga ataacacacg     420
cgccttaatg gaatgctggt acgggctgat aaagaatggc atgacagagg gatatgtgga     480
agctgataat gaacatatca agttccataa ggtaaaactg aaccccaccg cgtatagcag     540
aggtggcgca ccgatttatg tggtggctga atcagcttcg acgactgagt gggctgctca     600
acatggccta ccgatgatat taagttggat tataaatact aacgaaaaga aagcacaact     660
tgatctttat aatgaagtgg ctcaagaaca cgggcacgat gttcataata tcgaccattg     720
cttatcatat ataacatctg tagatcatga ctcaattaaa gcgaaagaga tttgccggca     780
atttctgggg cattggtatg attcttatgt gaatgctacg actatttttg atgattcaga     840
ccaaacaaaa ggttatggct tcaataaagg gcagtggcgt gactttgtat taaaaggaca     900
taaaaatact aatcgccgta ttgattacag ttacgaaatc aatcccgtgg gaacgccgca     960
ggaatgtatt gacataattc aaaccgacat tgatgctaca ggaatatcaa atatttgttg    1020
tggatttgaa gctaatggaa cagtagacga aattattgct tccatgaagc tcttccagtc    1080
tgatgtcatg ccatttctta aagaaacgca acgttcgcta ttattctgag gatcggttgt    1140
cgagtaagga tctccaggca tcaaataaaa cg                                  1172

<210> SEQ ID NO 69
<211> LENGTH: 1172
<212> TYPE: DNA
<213> ORGANISM: Artificial Sequence
<220> FEATURE:
<223> OTHER INFORMATION: reconstructed sequence

<400> SEQUENCE: 69
caattttcgt actgaaacat cttaatcatg cacaggagac tttctaatga aatttggaaa      60 cttttttgctt acataccaac ctccccaatt ttctcaaaca gaggtaatgc aacgtttggt     120
taaattaggt cgcgtgtctg aggagtgtgg ttttgatacc gtatggttac tggagcatca     180
tttcacggag tttggtttgc ttggtaaccc ttatgtcgct gctgcacatt tacttggcgc     240
gactaaaaaa ttgaatgtag gaactgccgc tattgttctt cccacagccc atccagtacg     300
ccaacttgaa gatgtgaatt tattggatca aatgtcaaaa ggacgatttc ggtttggtat     360
ttgccgaggg ctttacaaca aggactttcg cgtattcggc acagatatgg ataacagtcg     420
cgccttaatg gaatgctggt acgggctgat aaagaatggc atgacagagg gatatgtgga     480
agctgataat gaacatatca agttctataa ggtaaaagta gggcccaccg cgtatagcca     540
gggtggcgca ccgatttatg tggtggctga atcagcttcg acgactgagt gggctgctca     600
acatggccta ccgatgatat taagttggat tataaatact aacaaaaaga tcgcacaact     660
```

```
tgatctttat aatgaagtgg ctcaagaata tgggcacgat gttcataata tcgaccattg      720
cttatcatat ataacatctg tagatcatga ctcaatgaaa gcgaaagaga tttgccggaa      780
ctttctgggg cattggtatg attcttatgt gaatgctacg actatttttg atgattcaga      840
ccaaacaaaa ggttatgatt tcaataaagg gaagtggcgt gactttgtat taaaaggaca      900
taaagatact aatcgccgta ttgattacag ttacgaaatc aatcccgtgg aaacggtaaa      960
ggaatacatt gacataattc aaaaagacat tgatgctaca ggaatatcaa atatttgttg     1020
tggatttgaa gctaatggaa cagtagacga aattattgct tccatgaagc tcttccagtc     1080
tgatgtcatg ccatttctta agaaaaaca acgttcgcta ttattctgag gatcggttgt      1140
cgagtaagga tctccaggca tcaaataaaa cg                                    1172
```

<210> SEQ ID NO 70
<211> LENGTH: 1178
<212> TYPE: DNA
<213> ORGANISM: Artificial Sequence
<220> FEATURE:
<223> OTHER INFORMATION: reconstructed sequence

<400> SEQUENCE: 70

```
caattttcgt actgaaacat cttaatcatg cacaggagac tttctaatgc gctttggaaa       60 cttttttgctt acataccaac ctccccaatt ttctcaaaca gaggtaatga aacgtttggt      120
taaattaggt cgcgtgtctg aggagtgtgg ttttgatacc gtatggttac tggagcatca      180
tttcacggag tttggtttgc ttggtaaccc ttatgtcgct gctgcatatt tacttggcgc      240
gactaaaaaa ttgaatgtag gaactgccgc tattgttctt cccacagccc atccagtacg      300
ccaacttgaa gatgtgaatt tattggatca aatgtcaaaa ggacgatttc ggtttggtat      360
ttgccgaggg ctttacaaca aggactttaa tgtattcggc gttgatatga ataacacacg      420
cgccttaact gaatgctggt acgggctgat aaagaatggc atgacagagg gatatgtgga      480
agctgataat gaacatatca agttccataa ggtaaaagta aaccccaccg cgtatacaca      540
gggtggcgca ccgatttatg tggtggctga atcagcttcg acgactgagt gggctgctca      600
acatggccta ccgatgatat taagttggat tataaatact aacgaaaaga tcgcacaagc      660
tgatctttat aatgaagtgg ctcaagaata tgggcacgat gttcataata tcgaccattg      720
cttatcatat ataacatctg tagatcatga ctcaattaaa gcgaaagaga tttgccggaa      780
ctttctgggg cattggtatg attcttatgt gaatgctacg actatttttg atgattcaga      840
ccaaacaaaa ggttatgatt tcaataaagg gcagtggcgt gactttgtat taaaaggaca      900
taaacacact aatcgccgta ttgattacag ttacgaaatc aatcccgtgg aacgccgca       960 ggaatgtatt gacataattc aaaccgacat tgatgctaca ggaatatcaa atatttgttg     1020
tggatttgaa gctaatggaa cagtagacga aaaaattgct tccatgaagc tcttccagtc     1080
tgatgtcatg ccatttctta agaaacgca acgttcgcta ttaatgatcg cgtgaggatc      1140
ggttgtcgag taaggatctc caggcatcaa ataaaacg                             1178
```

<210> SEQ ID NO 71
<211> LENGTH: 1172
<212> TYPE: DNA
<213> ORGANISM: Artificial Sequence
<220> FEATURE:
<223> OTHER INFORMATION: reconstructed sequence -continued

```
<400> SEQUENCE: 71
caattttcgt actgaaacat cttaatcatg cacaggagac tttctaatga aatttggaaa      60 cttttttgctt acataccaac ctccccaatt ttctcaaaca gaggtaatga aacgtttggt     120
taaattaggt cgcgtgtctg aggagtgtgg ttttgatacc gtatggttac tggagcatca     180
tttcacggag tttggtttgc ttggtaaccc ttatgtcgct gctgcatatt tacttggcgc     240
gactaaaaaa ttgaatgtag gaactgccgc tattgttctt cccacagccc atccagtacg     300
ccaacttgaa gatgtgaatt tattggatca aatgtcaaaa ggacgatttc ggtttggtat     360
ttgccgaggg ctttacaaca aggactttcg cgtattcggc gttgatatga ataacacacg     420
cgccttaatg gaatgctggt acgggctgat aaagaatggc atgacagagg gatatgtgga     480
agctgataat gaacatatca agttccataa ggtaaaagta aaccccaccg cgtatagcaa     540
gggtggcgca ccgatttatg tggtggctga atcagcttcg acgactgagt gggctgctca     600
acatggccta ccgatgatat taagttggat tataaatact aacgaaaaga aagcacaact     660
tgagctttat aatgaagtgg ctcaagaaca cgggcacgat gttcataata tcgaccattg     720
cttatcatat ataacatctg tagatcatga ctcaattaaa gcgaaagaga tttgccggaa     780
ctttctgggg cattggtatg attcttatgt gaatgctacg actatttttg atgattcaga     840
caagacaaaa ggttatgatt tcaataaagg gcagtggcgt gactttgtat taaaaggaca     900
taaagatact aatcgccgta ttgattacag ttacgaaatc aatcccgtgg gaacgccgga     960
agaatgtatt gacataaattc aaaaagacat tgatgctaca ggaatatcaa atatttgttg    1020
tggatttgaa gctaatggaa cagtagacga aattattgct tccatgaagc tcttccagtc    1080
tgatgtcatg ccatttctta agaaaaaaca acgttcgcta ttatattgag gatcggttgt    1140
cgagtaagga tctccaggca tcaaataaaa cg                                   1172

<210> SEQ ID NO 72
<211> LENGTH: 1172
<212> TYPE: DNA
<213> ORGANISM: Artificial Sequence
<220> FEATURE:
<223> OTHER INFORMATION: reconstructed sequence

<400> SEQUENCE: 72
caattttcgt actgaaacat cttaatcatg cacaggagac tttctaatga aatttggaaa      60 cttttttgctt acataccaac ctccccaatt ttctcaatcc gaggtaatgc aacgtttggt     120
taaattaggt cgcgtgtctg aggagtgtgg ttttgatacc gtatggttac tggagcatca     180
tttcacggag tttggtttgc ttggtaaccc ttatgtcgct gctgcaaatt tacttggcgc     240
gactaaaaaa ttgaatgtag gaactgccgc tattgttctt cccacagccc atccagtacg     300
ccaacttgaa gatgtgaatt tattggatca aatgtcaaaa ggacgatttc ggtttggtat     360
ttgccgaggg ctttacaaca aggactttcg cgtattcggc acagatatgg ataacacacg     420
cgccttaact gaatgctggt acgggattat aaagaatggc atgacagagg gatatatgga     480
agctgataat gaacatatca agttccataa ggtaaaagta aaccccaccg cgtatagcca     540
gggtggcgca ccgatttatg tggtggctga atcagcttcg acgactgagt gggctgctca     600
acatggccta ccgatgatat taagttggat tataaataat aacgaaaaga tctatcaagc     660
tgagctttat aatgaagtgg ctctcgaata tgggcacgat attacgaata tcgaccattg     720
cttatcatat ataacatctg tagatcatga ctcaattaaa gcgaaagaga tttgccggga     780
```

-continued

```
ttttctgggg cattggtatg attcttatgt gaatgctacg actattttg atgattcaga        840 ccaaacaaaa ggttatggct tcaataaagg gcagtggcgt gactttgtat taaaaggaca        900
taaagatact aatcgccgta ttgattacag ttacgaaatc aatcccgtgg gaacgccgca        960
ggaatgtatt gacataattc aaaccgacat tgatgctaca ggaatatcaa atatttgttg       1020
tggatttaag gctaatggaa cagtagacga aattattgct tccatgaagc tcttccagtc       1080
tgatgtcatg ccatttctta agaaaaaaca acgttcgcta ttatattgag gatcggttgt       1140
cgagtaagga tctccaggca tcaaataaaa cg                                     1172
```

```
<210> SEQ ID NO 73
<211> LENGTH: 1172
<212> TYPE: DNA
<213> ORGANISM: Artificial Sequence
<220> FEATURE:
<223> OTHER INFORMATION: reconstructed sequence

<400> SEQUENCE: 73
```

```
caattttcgt actgaaacat cttaatcatg cacaggagac tttctaatga aatttggaaa         60 cttttttgctt acataccaac ctccccaatt ttctcaaaca gaggtaatgc aacgtttggt        120
tgaattaggt cgcgtgtctg aggagtgtgg ttttgatacc gtatggttac tggagcatca        180
tttcacggag tttggtttgg gtggtaacgt acaggtcgct gctgcatttt tacttggcgc        240
gactaaaaaa ttgaatgtag gaactgccgc tattgttctt cccacagccc atccagtacg        300
ccaacttgaa gatgtgaatt tattggatca aatgtcaaaa ggacgatttc ggtttggtat        360
ttgccgaggg ctttacaaca aggactttcg cgtattcggc gttgatatga ataacagtcg        420
cgccttaatg gaaaagtggt acgagcgtat aaagcgtggc attacagagg gatatatgga        480
agctgataat gaacatatca agttccataa ggtaaaagta aaccccaccg cgtatagcca        540
gggtggcgca ccgatttatg tggtggctac ttcagcttcg acgactgagt gggctgctca        600
acatggccta ccgatgatat taagttggat tataaatcgc aacgaaaaga tcgcacaaat        660
tgagctttat aatgaagtgg ctcaagaatc cgggcacgat attcataata tcgaccattg        720
cttatcatat ataacatctg tagatcatga ctcaattaaa gcgaaagaga tttgccggaa        780
ctttctgggg cattggtatg attcttatgt gaatgctacg actattttg atgattcaga        840 caagacaaaa ggttatggct tcaataaagg gcagtgggct gactttgtat taaaaggaca        900
taaaaatact aatcgccgta ttgattacag ttacgaaatc aatcccgtgg gaacgccgaa        960
ggaatgtatt gacataattc aaaccgacat tgatgctaca ggaatatcaa atatttgttg       1020
tggatttgaa gctaatggaa cagtagacga aattattgct tccatgaagc tcttccagaa       1080
agatgtcatg ccatttctta agaaacgca acgttcgcta ttattctgag gatcggttgt       1140
cgagtaagga tctccaggca tcaaataaaa cg                                     1172
```

```
<210> SEQ ID NO 74
<211> LENGTH: 1172
<212> TYPE: DNA
<213> ORGANISM: Artificial Sequence
<220> FEATURE:
<223> OTHER INFORMATION: reconstructed sequence

<400> SEQUENCE: 74
```

```
caattttcgt actgaaacat cttaatcatg cacaggagac tttctaatga aatttggaaa         60 cttttttgctt acataccaac ctccccaatt ttctcaaggt gaggtaatga aacgtttggt        120
taacttaggt cgcgtgtctg aggagtgtgg ttttgatacc gtatggttac tggagcatca        180
```

```
tttcacggag tttggtttgc ttggtaaccc ttatgtcgct gctgcatatt tacttggcgc      240
gactaaaaaa ttgaatgtag gaactgccgc tattgttctt cccacagccc atccagtacg      300
ccaacttgaa gatgtgaatt tattggatca aatgtcaaaa ggacgatttc ggtttggtat      360
ttgccgaggg ctttacaaca aggactttcg cgtattcggc gttgatatgg ataacacacg      420
cgccttaatg gaatgctggt acgggctgat aaaggaaggc atgacagagg gatatgtgga      480
agctgataat gaacatatca agttccataa ggtaaaagta aaccccaccg cgtatagcaa      540
gggtggcgca ccggtttatg tggtggctga atcagcttcg acgactgagt gggctgctca      600
acatggccta ccgatgatat taagttggat tataaatact aacgaaaaga aagcacaact      660
tgattactat aatgaagtgg ctcaagaata tgggcacgat gttcataata tcgaccattg      720
cttatcatat ataacatctg tagatcatga ctcaattaaa gcgaaagaga tttgccggaa      780
atttctgggg cattggtatg attcttatgt gaatgctacg actatttttg atgattcaga      840
ccaaacaaaa ggttatgatt tcaataaagg gcagtggcgt gactttgtat taaaaggaca      900
taaagatact aatcgccgta ttgattacag ttacgaaatc aatcccgtgg gaacgccgga      960
agaatgtatt gacataattc aaaccgacat tgatgctaca ggaatatcaa atatttgttg     1020
tggatttgaa gctaatggaa cagtagacga aattattgct tccatgaagc tcttccagtc     1080
tgatgtcatg ccatttctta agaaaaaaca acgttcgcta ttatattgag gatcggttgt     1140
cgagtaagga tctccaggca tcaaataaaa cg                                    1172
```

```
<210> SEQ ID NO 75
<211> LENGTH: 1172
<212> TYPE: DNA
<213> ORGANISM: Artificial Sequence
<220> FEATURE:
<223> OTHER INFORMATION: reconstructed sequence

<400> SEQUENCE: 75
```

```
caattttcgt actgaaacat cttaatcatg cacaggagac tttctaatga aatttggaaa       60 cttttttgctt acataccaac ctcccccaatt ttctcaaaca gaggtaatgc aacgtttggt     120
taaattaggt cgcgtgtctg aggagtgtgg ttttgatacc gtatggttac tggagcatca      180
tttcacggag tttggtttgc ttggtaaccc ttatgtcgct gctgcatatt tacttggcgc      240
gactaaaaaa ttgaatgtag gaactgccgc tattgttctt cccacagccc atccagtacg      300
ccaacttgaa gatgtgaatt tattggatca aatgtcaaaa ggacgatttc ggtttggtat      360
ttgccgaggg ctttacaaca aggactttcg cgtattcggc acagatatgg ataacagtcg      420
cgccttaatg gaatgctggt acgggctgat aaagaatggc atgacagagg gatatgtgga      480
agctgataat gaacatatca agttccataa ggtaaaagta aaccccaccg cgtatagcca      540
gggtggcgca ccggtttatg tggtggctga atcagcttcg acgactgagt gggctgctca      600
acatggccta ccgatgatat taagttggat tataaatact aacgaaaaga aagcacaact      660
tgagctttat aatgaagtgg ctcaagaata tgggcacgat attcataata tcgaccattg      720
cttatcatat ataacatctg tagatcatga ctcaattaaa gcgaaagaga tttgccggaa      780
ctttctgggg cattggtatg attcttatgt gaatgctacg actatttttg atgattcaga      840
ccaaacaaaa ggttatgatt tcaataaagg gcagtggcgt gactttgtat taaaaggaca      900
taaagatact aatcgccgta ttgattacag ttacgaaatc aatcccgtgg gaacgccgca      960
ggaatgtatt gacataattc aaaccgacat tgatgctaca ggaatatcaa atatttgttg     1020
```

```
tggatttgaa gctaatggaa cagtagacga aattattgct tccatgaagc tcttccagtc      1080
tgatgtcatg ccatttctta aagaaaaaca acgttcgcta ttatattgag gatcggttgt      1140
cgagtaagga tctccaggca tcaaataaaa cg                                    1172

<210> SEQ ID NO 76
<211> LENGTH: 3276
<212> TYPE: DNA
<213> ORGANISM: Artificial Sequence
<220> FEATURE:
<223> OTHER INFORMATION: Plasmid

<400> SEQUENCE: 76
tcagataaaa tatttctaga tttcagtgca atttatctct tcaaatgtag cacctgaagt        60
cagccccata cgatataagt tgttactagt gcttggattc tcaccaataa aaaacgcccg       120
gcggcaaccg agcgttctga acaaatccag atggagttct gaggtcatta ctggatctat       180
caacaggagt ccaagcgagc tcgatatcaa attacgcccc gccctgccac tcatcgcagt       240
actgttgtaa ttcattaagc attctgccga catggaagcc atcacagacg gcatgatgaa       300
cctgaatcgc cagcggcatc agcaccttgt cgccttgcgt ataatatttg cccatggtga       360
aaacgggggc gaagaagttg tccatattgg ccacgtttaa atcaaaactg gtgaaactca       420
cccagggatt ggctgagacg aaaaacatat tctcaataaa ccctttaggg aaataggcca       480
ggttttcacc gtaacacgcc acatcttgcg aatatatgtg tagaaactgc cggaaatcgt       540
cgtggtattc actccagagc gatgaaaacg tttcagtttg ctcatggaaa acggtgtaac       600
aagggtgaac actatcccat atcaccagct caccgtcttt cattgccata cggaattccg       660
gatgagcatt catcaggcgg gcaagaatgt gaataaaggc cggataaaac ttgtgcttat       720
ttttctttac ggtctttaaa aaggccgtaa tatccagctg aacggtctgg ttataggtac       780
attgagcaac tgactgaaat gcctcaaaat gttctttacg atgccattgg gatatatcaa       840
cggtggtata tccagtgatt tttttctcca ttttagcttc cttagctcct gaaaatctcg       900
ataactcaaa aaatacgccc ggtagtgatc ttatttcatt atggtgaaag ttggaacctc       960
ttacgtgccg atcaacgtct cattttcgcc agatatcgac gtcgacgtcg aattcaaaag      1020
atcttaagta agtaagagta tacgtatatc ggctaataac gtattaaggc gcttcggcgc      1080
ctttttttat gggggtattt tcatcccaat ccacacgtcc aacgcacagc aaacaccacg      1140
tcgaccctat cagctgcgtg cttttctatga gtcgttgctg cataacttga caattaatca      1200
tccggctcgt ataatgtgtg gagggcccaa gttcacttaa aaaggagatc aacaatgaaa      1260
gcaattttcg tactgaaaca tcttaatcat gcacaggaga ctttctaatg aaatttggaa      1320 acttttttgct tacataccaa cctccccaat tttctcaaac agaggtaatg aaacgtttgg      1380
ttaaattagg tcgcatctct gaggagtgtg gttttgatac cgtatggtta ctggagcatc      1440
atttcacgga gtttggtttg cttggtaacc cttatgtcgc tgctgcatat ttacttggcg      1500
cgactaaaaa attgaatgta ggaactgccg ctattgttct tcccacagcc catccagtac      1560
gccaacttga agatgtgaat ttattggatc aaatgtcaaa aggacgattt cggtttggta      1620
tttgccgagg gctttacaac aaggactttc gcgtattcgg cacagatatg aataacagtc      1680
gcgccttagc ggaatgctgg tacgggctga taaagaatgg catgacagag ggatatatgg      1740
aagctgataa tgaacatatc aagttccata aggtaaaagt aaaccccgcg gcgtatagca      1800
gaggtggcgc accggtttat gtggtggctg aatcagcttc gacgactgag tgggctgctc      1860
aatttggcct accgatgata ttaagttgga ttataaatac taacgaaaag aaagcacaac      1920
```

```
ttgagcttta taatgaagtg gctcaagaat atgggcacga tatttcataat atcgaccatt      1980 gcttatcata tataacatct gtagatcatg actcaattaa agcgaaagag atttgccgga      2040
aatttctggg gcattggtat gattcttatg tgaatgctac gactattttt gatgattcag      2100
accaaacaag aggttatgat ttcaataaag ggcagtggcg tgactttgta ttaaaaggac      2160
ataaagatac taatcgccgt attgattaca gttacgaaat caatcccgtg ggaacgccgc      2220
aggaatgtat tgacataatt caaaaagaca ttgatgctac aggaatatca aatatttgtt      2280
gtggatttga agctaatgga acagtagacg aaattattgc ttccatgaag ctcttccagt      2340
ctgatgtcat gccatttctt aaagaaaaac aacgttcgct attatattag ggatcggttg      2400
tcgagtaagg atctccaggc atcaaataaa acgaaaggct cagtcgaaag actgggcctt      2460 tcgtttttatc tgttgtttgt cggtgaacgc tctctactag agtcacactg gctcaccttc      2520
gggtgggcct ttctgcgttt ataggatcct aactcgagcc tagggatata ttccgcttcc      2580
tcgctcactg actcgctacg ctcggtcgtt cgactgcggc gagcggaaat ggcttacgaa      2640
cggggcggag atttcctgga agatgccagg aagatactta acagggaagt gagagggccg      2700
cggcaaagcc gtttttccat aggctccgcc ccctgacaa gcatcacgaa atctgacgct      2760
caaatcagtg gtggcgaaac ccgacaggac tataaagata ccaggcgttt cccctggcg      2820 gctccctcgt gcgctctcct gttcctgcct ttcggtttac cggtgtcatt ccgctgttat      2880
ggccgcgttt gtctcattcc acgcctgaca ctcagttccg ggtaggcagt tcgctccaag      2940
ctggactgta tgcacgaacc ccccgttcag tccgaccgct gcgccttatc cggtaactat      3000
cgtcttgagt ccaacccgga aagacatgca aaagcaccac tggcagcagc cactggtaat      3060
tgatttagag gagttagtct tgaagtcatg cgccggttaa ggctaaactg aaaggacaag      3120
ttttggtgac tgcgctcctc caagccagtt acctcggttc aaagagttgg tagctcagag      3180
aaccttcgaa aaaccgccct gcaaggcggt tttttcgttt tcagagcaag agattacgcg      3240
cagaccaaaa cgatctcaag aagatcatct tattaa                                3276
```

```
<210> SEQ ID NO 77
<211> LENGTH: 11609
<212> TYPE: DNA
<213> ORGANISM: Artificial Sequence
<220> FEATURE:
<223> OTHER INFORMATION: Plasmid

<400> SEQUENCE: 77
tcatttcgaa ccccagagtc ccgctcagaa gaactcgtca agaaggcgat agaaggcgat        60
gcgctgcgaa tcgggagcgg cgataccgta agcacgagg aagcggtcag cccattcgcc       120
gccaagctct tcagcaatat cacgggtagc caacgctatg tcctgatagc ggtccgccac       180
acccagccgg ccacagtcga tgaatccaga aaagcggcca ttttccacca tgatattcgg       240
caagcaggca tcgccatggg tcacgacgag atcctcgccg tcgggcatgc gcgccttgag       300
cctggcgaac agttcggctg gcgcgagccc ctgatgctct tcgtccagat catcctgatc       360
gacaagaccg gcttccatcc gagtacgtgc tcgctcgatg cgatgtttcg cttggtggtc       420
gaatgggcag gtagccggat caagcgtatg cagccgccgc attgcatcag ccatgatgga       480
tactttctcg gcaggagcaa ggtgagatga caggagatcc tgccccggca cttcgcccaa       540
tagcagccag tccttcccg cttcagtgac aacgtcgagc acagctgcgc aaggaacgcc       600
cgtcgtggcc agccacgata ccgcgcctgc ctcgtcctgc agttcattca gggcaccgga       660
```

-continued

```
caggtcggtc ttgacaaaaa gaaccgggcg cccctgcgct gacagccgga acacggcggc      720
atcagagcag ccgattgtct gttgtgccca gtcatagccg aatagcctct ccacccaagc      780
ggccggagaa cctgcgtgca atccatcttg ttcaatcatg cgaaacgatc ctcatcctgt      840
ctcttgatca gatcttgatc ccctgcgcca tcagatcctt ggcggcaaga aagccatcca      900
gtttactttg cagggcttcc caaccttacc agagggcgcc ccagccgtgg caattccggt      960
tcgctgctag acaacatcag caaggagaaa ggggctaccg cgcaaccagc agcccctttta     1020 taaaggcgct tcagtagtca gaccagcatc agtcctgaaa aggcgggcct gcgcccgcct     1080
ccaggttgct acttaccgga ttcgtaagcc atgaaagccg ccacctccct gtgtccgtct     1140
ctgtaacgaa tctcgcacag cgattttcgt gtcagataag tgaatatcaa cagtgtgaga     1200
cacacgatca acacacacca gacaagggaa cttcgtggta gtttcatggc cttcttctcc     1260
ttgcgcaaag cgcggtaaga ggctatcctg atgtggacta gacataggga tgcctcgtgg     1320
tggttaatga aaattaactt actacggggc tatcttcttt ctgccacaca acacggcaac     1380
aaaccacctt cacgtcatga ggcagaaagc ctcaagcgcc gggcacatca tagcccatat     1440
acctgcacgc tgaccacact cactttccct gaaaataatc cgctcattca gaccgttcac     1500
gggaaatccg tgtgattgtt gccgcatcac gctgcctccc ggagtttgtc tcgagcactt     1560
ttgttacccg ccaaacaaaa cccaaaaaca acccataccc aacccaataa aacaccaaaa     1620
caagacaaat aatcattgat tgatggttga aatggggtaa acttgacaaa caaacccact     1680
taaaacccaa aacatacccca aacacacacc aaaaaaacac cataaggagt tttataaatg     1740
ttggtattca ttgatgacgg ttcaacaaac atcaaactac agtggcagga aagcgacgga     1800
acaattaaac agcacattag cccgaacagc ttcaaacgcg agtgggcagt ctcttttggt     1860
gataaaaagg tctttaacta cacactgaac ggcgaacagt attcatttga tccaatcagc     1920
ccggatgctg tagtcacaac caatatcgca tggcaataca gcgacgttaa tgtcgttgca     1980
gtgcatcacg cctactgac cagtggtctg ccggtaagcg aagtggatat tgtttgcaca     2040
cttcctctga cagagtatta cgacagaaat aaccaaccca atacggaaaa tattgagcgt     2100
aagaaagcaa acttccggaa aaaaattaca ttaaatggcg gggatacatt cacaataaaa     2160
gatgtaaaag tcatgcctga atctataccg gcaggttatg aagttctaca agaactggat     2220
gagttagatt ctttattaat tatagatctc gggggcacca cattagatat ttctcaggta     2280
atggggaaat tatcggggat cagtaaaata tacggagact catctcttgg tgtctctctg     2340
gttacatctg cagtaaaaga tgccctttct cttgcgagaa caaaaggaag tagctatctt     2400
gctgacgata taatcattca cagaaaagat aataactatc tgaagcaacg aattaatgat     2460
gagaacaaaa tatcaatagt caccgaagca atgaatgaag cacttcgtaa acttgagcaa     2520
cgtgtattaa atacgctcaa tgaattttct ggttatactc atgttatggt tataggcggt     2580
ggcgcagaat aatatgcgca tgcagtaaaa aaacacacac agattcgtga tgaacgtttt     2640
ttcaaaacca ataactctca atatgattta gttaacggta tgtatctcat aggtaattaa     2700
tgatggacaa gcgcagaacc attgccttca aactaaatcc agatgtaaat caaacagata     2760
aaattgtttg tgatacactg gacagtatcc cgcaaggggga acgaagccgc cttaaccggg     2820
ccgcactgac ggcaggtctg gccttataca gacaagatcc ccggacccct ttccttttat     2880
gtgagctgct gacgaaagaa accacatttt cagatatcgt gaatatattg agatcgctat     2940
ttccaaaaga gatggccgat tttaattctt caatagtcac tcaatcctct tcacaacaag     3000
agcaaaaaag tgatgaagag accaaaaaaa atgcgatgaa gctaataaat taattcaatt     3060
```

```
attattgagt tccctttatc cactatcagg ctggataaag ggaactcaat caagttattt      3120
tcttaccagt cattacataa tcgttattat gaaataatcg tttgcactgt ctctgttatt      3180
caggcaattt caataaaggc acttgctcac gctctgtcat tttctgaaac tcttcatgct      3240
ggaattgata aaacagaatt tgcctggcgg cagtagcgcg gtggtcccac ctgaccccat      3300
gccgaactca gaagtgaaac gccgtagcgc cgatggtagt gtggggtctc cccatgcgag      3360
agtagggaac tgccaggcat caaataaaac gaaaggctca gtcgaaagac tgggcctttc      3420
gttttatctg ttgtttgtcg gtgaacgctc tcctgagtag gacaaatccg ccgggagcgg      3480
atttgaacgt tgcgaagcaa cggcccggag ggtggcgggc aggacgcccg ccataaactg      3540
ccaggcatca aattaagcag aaggccatcc tgacggatgg cctttttgcg tttctacaaa      3600
ctcgaattca taagaatgcg gccgctgtgg tagcacagaa taatgaaaag tgtgtaaaga      3660
agggtaaaaa aaaccgaatg cgaggcatcc ggttgaaata ggggtaaaca gacattcaga      3720
aatgaatgac ggtaataaat aaagttaatg atgatagcgg gagttattct agttgcgagt      3780
gaaggttttg ttttgacatt cagtgctgtc aaatacttaa gaataagtta ttgattttaa      3840
ccttgaatta ttattgcttg atgttaggtg cttatttcgc cattccgcaa taatcttaaa      3900
aagttccctt gcatttacat tttgaaacat ctatagcgat aaatgaaaca tcttaaaagt      3960
tttagtatca tattcgtgtt ggattattct gcattttggg ggagaatgga cttgccgact      4020
gattaatgag ggttaatcag tatgcagtgg cataaaaaag caaataaagg catataacag      4080
atcgatctta aacatccaca ggaggatggg atccaaaata aggaggaaaa aaaaatgact      4140
agtatgacta aaaaaatttc attcattatt aacggccagg ttgaaatctt tcccgaaggt      4200
gatgatttag tgcaatccat taattttggt gataatagtg tttacctgcc aatattgaat      4260
gactctcatg taaaaaacat tattgattgt aatggaaata acgaattacg gttgcataac      4320
attgtcaatt ttctctatac ggtagggcaa agatggaaaa atgaagaata ctcaagacgc      4380
aggacataca ttcgtgactt aaaaaaatat atgggatatt cagaagaaat ggctaagcta      4440
gaggccaatt ggatatctat gattttatgt tctaaaggcg gcctttatga tgttgtagaa      4500
aatgaacttg gttctcgcca tatcatggat gaatggctac ctcaggatga aagttatgtt      4560
cgggcttttc cgaaaggtaa atctgtacat ctgttggcag gtaatgttcc attatctggg      4620
atcatgtcta tattacgcgc aattttaact aagaatcagt gtattataaa aacatcgtca      4680
accgatcctt ttaccgctaa tgcattagcg ttaagtttta ttgatgtaga ccctaatcat      4740
ccgataacgc gctctttatc tgttatatat tggccccacc aaggtgatac atcactcgca      4800
aaagaaatta tgcaacatgc ggatgttatt gtcgcttggg gagggccaga tgcgattaat      4860
tgggcggtag agcatcgcgcc atcttatgct gatgtgatta aatttggttc taaaaagagt      4920
ctttgcatta tcgataatcc tgttgatttg acgtccgcag cgacaggtgc ggctcatgat      4980
gtttgttttt acgatcagcg agcttgtttt tctgcccaaa acatatatta catgggaaat      5040
cattatgagg aatttaagtt agcgttgata gaaaaactta atctatatgc gcatatatta      5100
ccgaatgcca aaaagatttt tgatgaaaag gcggcctatt ctttagttca aaaagaaagc      5160
ttgtttgctg gattaaaagt agaggtggat attcatcaac gttggatgat tattgagtca      5220
aatgcaggtg tggaatttaa tcaaccactt ggcagatgtg tgtaccttca tcacgtcgat      5280
aatattgagc aaatattgcc ttatgttcaa aaaaataaga cgcaaaccat atctattttt      5340
ccttgggagt catcatttaa atatcgagat gcgttagcat taaaaggtgc ggaaaggatt      5400
```

-continued

```
gtagaagcag gaatgaataa catatttcga gttggtggat ctcatgacgg aatgagaccg      5460
ttgcaacgat tagtgacata tatttctcat gaaaggccat ctaactatac ggctaaggat      5520
gttgcggttg aaatagaaca gactcgattc ctggaagaag ataagttcct tgtatttgtc      5580
ccataatagg taaaaagtat ggaaaatgaa tcaaaatata aaaccatcga ccacgttatt      5640
tgtgttgaag gaaataaaaa aattcatgtt tgggaaacgc tgccagaaga aaacagccca      5700
aagagaaaga atgccattat tattgcgtct ggttttgccc gcaggatgga tcattttgct      5760
ggtctggcgg aatatttatc gcggaatgga tttcatgtga tccgctatga ttcgcttcac      5820
cacgttggat tgagttcagg gacaattgat gaatttacaa tgtctatagg aaagcagagc      5880
ttgttagcag tggttgattg gttaactaca cgaaaaataa ataacttcgg tatgttggct      5940
tcaagcttat ctgcgcggat agcttatgca agcctatctg aaatcaatgc ttcgtttttta     6000 atcaccgcag tcggtgttgt taacttaaga tattctcttg aaagagcttt agggtttgat      6060
tatctcagtc tacccattaa tgaattgccg aataatctag attttgaagg ccataaattg      6120
ggtgctgaag tctttgcgag agattgtctt gattttggtt gggaagattt agcttctaca      6180
attaataaca tgatgtatct tgatataccg tttattgctt ttactgcaaa taacgataat      6240
tgggtcaagc aagatgaagt tatcacattg ttatcaaata ttcgtagtaa tcgatgcaag      6300
atatattctt tgttaggaag ttcgcatgac ttgagtgaaa atttagtggt cctgcgcaat      6360
ttttatcaat cggttacgaa agccgctatc gcgatggata atgatcatct ggatattgat      6420
gttgatatta ctgaaccgtc atttgaacat ttaactattg cgacagtcaa tgaacgccga      6480
atgagaattg agattgaaaa tcaagcaatt tctctgtctt aaaatctatt gagatattct      6540
atcactcaaa tagcaatata aggactctct atgaaatttg gaaactttag tactcaacgt      6600
tcgctattat attagctaag gagaaagaaa tgaaatttgg attgttcttc cttaacttca      6660
tcaattcaac aactgttcaa gaacaaagta tagttcgcat gcaggaaata acggagtatg      6720
ttgataagtt gaattttgaa cagatttttag tgtatgaaaa tcatttttca gataatggtg      6780
ttgtcggcgc tcctctgact gtttctggtt ttctgctcgg tttaacagag aaaattaaaa      6840
ttggttcatt aaatcacatc attacaactc atcatcctgt ccgcatagcg gaggaagctt      6900
gcttattgga tcagttaagt gaagggagat ttatttttagg gtttagtgat tgcgaaaaaa     6960
aagatgaaat gcatttttttt aatcgcccgg ttgaatatca acagcaacta tttgaagagt      7020
gttatgaaat cattaacgat gctttaacaa caggctattg taatccagat aacgattttt      7080
atagcttccc taaaatatct gtaaatcccc atgcttatac gccaggcgga cctcggaaat      7140
atgtaacagc aaccagtcat catattgttg agtgggcggc caaaaaaggt attcctctca      7200
tctttaagtg ggatgattct aatgatgtta gatatgaata tgctgaaaga tataaagccg      7260
ttgcggataa atatgacgtt gacctatcag agatagacca tcagttaatg atattagtta      7320
actataacga agatagtaat aaagctaaac aagagacgcg tgcatttatt agtgattatg      7380
ttcttgaaat gcaccctaat gaaaatttcg aaaataaact tgaagaaata attgcagaaa      7440
acgctgtcgg aaattatacg gagtgtataa ctgcggctaa gttggcaatt gaaaagtgtg      7500
gtgcgaaaag tgtattgctg tcctttgaac caatgaatga tttgatgagc caaaaaaatg      7560
taatcaatat tgttgatgat aatattaaga agtaccacat ggaatatacc taatagattt      7620
cgagttgcag cgaggcggca agtgaacgaa tccccaggag catagataac tatgtgactg      7680
gggtgagtga aagcagccaa caaagcagca gcttgaaaga tgaagggtat aaaagagtat      7740
gacagcagtg ctgccatact ttctaatatt atcttgagga gtaaaacagg tatgacttca      7800
```

-continued

```
tatgttgata aacaagaaat tacagcaagc tcagaaattg atgatttgat tttttcgagc      7860
gatccattag tgtggtctta cgacgagcag gaaaaaatca gaaagaaact tgtgcttgat      7920
gcatttcgta atcattataa acattgtcga gaatatcgtc actactgtca ggcacacaaa      7980
gtagatgaca atattacgga aattgatgac atacctgtat tcccaacatc ggtttttaag      8040
tttactcgct tattaacttc tcaggaaaac gagattgaaa gttggtttac cagtagcggc      8100
acgaatggtt taaaaagtca ggtggcgcgt gacagattaa gtattgagag actcttaggc      8160
tctgtgagtt atggcatgaa atatgttggt agttggtttg atcatcaaat agaattagtc      8220
aatttgggac cagatagatt taatgctcat aatatttggt ttaaatatgt tatgagtttg      8280
gtggaattgt tatatcctac gacatttacc gtaacagaag aacgaataga ttttgttaaa      8340
acattgaata gtcttgaacg aataaaaaat caagggaaag atctttgtct tattggttcg      8400
ccatacttta tttatttact ctgccattat atgaaagata aaaaaatctc attttctgga      8460
gataaaagcc tttatatcat aaccggaggc ggctggaaaa gttacgaaaa agaatctctg      8520
aaacgtgatg atttcaatca tcttttattt gatactttca atctcagtga tattagtcag      8580
atccgagata tatttaatca agttgaactc aacacttgtt tctttgagga tgaaatgcag      8640
cgtaaacatg ttccgccgtg ggtatatgcg cgagcgcttg atcctgaaac gttgaaacct      8700
gtacctgatg gaacgccggg gttgatgagt tatatggatg cgtcagcaac cagttatcca      8760
gcatttattg ttaccgatga tgtcgggata attagcagag aatatggtaa gtatcccggc      8820
gtgctcgttg aaattttacg tcgcgtcaat acgaggacgc agaaagggtg tgctttaagc      8880
ttaaccgaag cgtttgatag ttgatgacct gcaggcatgc aagcttgcgg ccgcgggccc      8940
catggatcga tagctggtcg acacaatctg ccctttcgaa agatcccaac gaaaagcgtg      9000
accacatggt ccttcttgag tttgtaactg ctgctgggat tacacatggc atggatgagc      9060
tctacaaata atgagctagc tgaaaaccta gcccgcctaa tgagcgggct ttttttttctc      9120 ggcctaggtt tcacctgttc tattaggtgt tacatgctgt tcatctgtta cattgtcgat      9180
ctgttcatgg tgaacagctt taaatgcacc aaaaactcgt aaaagctctg atgtatctat      9240
cttttttaca ccgttttcat ctgtgcatat ggacagtttt ccctttgata tctaacggtg      9300
aacagttgtt ctacttttgt ttgttagtct tgatgcttca ctgatagata caagagccat      9360
aagaacctca gatccttccg tatttagcca gtatgttctc tagtgtggtt cgttgttttt      9420
gcgtgagcca tgagaacgaa ccattgagat catgcttact ttgcatgtca ctcaaaaatt      9480
ttgcctcaaa actggtgagc tgaatttttg cagttaaagc atcgtgtagt gttttttctta      9540 gtccgttacg taggtaggaa tctgatgtaa tggttgttgg tattttgtca ccattcattt      9600
ttatctggtt gttctcaagt tcggttacga gatccatttg tctatctagt tcaacttgga      9660
aaatcaacgt atcagtcggg cggcctcgct tatcaaccac caatttcata ttgctgtaag      9720
tgtttaaatc tttacttatt ggtttcaaaa cccattggtt aagcctttta aactcatggt      9780
agttattttc aagcattaac atgaacttaa attcatcaag gctaatctct atatttgcct      9840
tgtgagtttt cttttgtgtt agttctttta ataaccactc ataaatcctc atagagtatt      9900
tgttttcaaa agacttaaca tgttccagat tatattttat gaattttttt aactggaaaa      9960
gataaggcaa tatctcttca ctaaaaacta attctaattt ttcgcttgag aacttggcat     10020
agtttgtcca ctggaaaatc tcaaagcctt taaccaaagg attcctgatt ccacagttc      10080 tcgtcatcag ctctctggtt gctttagcta atacaccata agcattttcc ctactgatgt     10140
```

-continued

```
tcatcatctg agcgtattgg ttataagtga acgataccgt ccgttctttc cttgtagggt   10200
tttcaatcgt ggggttgagt agtgccacac agcataaaat tagcttggtt tcatgctccg   10260
ttaagtcata gcgactaatc gctagttcat ttgctttgaa aacaactaat tcagacatac   10320
atctcaattg gtctaggtga tttttaatcac tataccaatt gagatgggct agtcaatgat   10380
aattactagt cctttttcctt tgagttgtgg gtatctgtaa attctgctag acctttgctg   10440
gaaaacttgt aaattctgct agaccctctg taaattccgc tagacctttg tgtgtttttt   10500
ttgtttatat tcaagtggtt ataatttata gaataaagaa agaataaaaa aagataaaaa   10560
gaatagatcc cagccctgtg tataactcac tactttagtc agttccgcag tattacaaaa   10620
ggatgtcgca aacgctgttt gctcctctac aaaacagacc ttaaaaccct aaaggcttaa   10680
gtagcaccct cgcaagctcg ggcaaatcgc tgaatattcc ttttgtctcc gaccatcagg   10740
cacctgagtc gctgtctttt tcgtgacatt cagttcgctg cgctcacggc tctggcagtg   10800
aatgggggta aatggcacta caggcgcctt ttatggattc atgcaaggaa actacccata   10860
atacaagaaa agcccgtcac gggcttctca gggcgtttta tggcgggtct gctatgtggt   10920
gctatctgac tttttgctgt tcagcagttc ctgccctctg attttccagt ctgaccactt   10980
cggattatcc cgtgacaggt cattcagact ggctaatgca cccagtaagg cagcggtatc   11040
atcaacaggc ttacccgtct tactgtcaac cggatctaaa acactaggcc caagagtttg   11100
tagaaacgca aaaaggccat ccgtcaggat ggccttctgc ttaatttgat gcctggcagt   11160
ttatggcggg cgtcctgccc gccaccctcc gggccgttgc ttcgcaacgt tcaaatccgc   11220
tcccggcgga tttgtcctac tcaggagagc gttcaccgac aaacaacaga taaaacgaaa   11280
ggcccagtct ttcgactgag cctttcgttt tatttgatgc ctggcagttc cctactctcg   11340 catgggggaga ccccacacta ccatcggcgc tacggcgttt cacttctgag ttcggcatgg   11400
ggtcaggtgg gaccaccgcg ctactgccgc caggcaaatt ctgtttttatc agaccgcttc   11460 tgcgttctga tttaatctgt atcaggctga aaatcttctc tcatccgcca aaacagccaa   11520
gctggatcta aaacactagc ccaaccttttc atagaaggcg gcggtggaat cgaaatctcg   11580
tgatggcagg ttgggcgtcg cttggtcgg                                     11609
```